(12) United States Patent
Rikihisa et al.

(10) Patent No.: US 11,492,391 B1
(45) Date of Patent: Nov. 8, 2022

(54) INTRACELLULAR NANOBODY TARGETING T4SS EFFECTOR INHIBITS EHRLICHIA INFECTION

(71) Applicant: Ohio State Innovation Foundation, Columbus, OH (US)

(72) Inventors: Yasuko Rikihisa, Columbus, OH (US); Wenqing Zhang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 17/654,708

(22) Filed: Mar. 14, 2022

Related U.S. Application Data

(60) Provisional application No. 63/168,652, filed on Mar. 31, 2021.

(51) Int. Cl.
| | |
|---|---|
| *C07K 16/12* | (2006.01) |
| *A61K 47/68* | (2017.01) |
| *A61P 31/04* | (2006.01) |
| *A61K 39/00* | (2006.01) |

(52) U.S. Cl.
CPC ...... *C07K 16/1246* (2013.01); *A61K 47/6811* (2017.08); *A61K 47/6843* (2017.08); *A61P 31/04* (2018.01); *A61K 2039/505* (2013.01); *C07K 2317/565* (2013.01); *C07K 2317/569* (2013.01); *C07K 2317/76* (2013.01)

(58) Field of Classification Search
None
See application file for complete search history.

(56) References Cited

U.S. PATENT DOCUMENTS 8,409,817 B2 * 4/2013 O'Connor, Jr. .... C07K 16/1246
435/7.1

OTHER PUBLICATIONS

Vincke, Cecile, et al. "General strategy to humanize a camelid single-domain antibody and identification of a universal humanized nanobody scaffold." Journal of Biological Chemistry 284.5 (2009): 3273-3284. (Year: 2009).*

Kipriyanov, Sergey M., and Fabrice Le Gall. "Generation and production of engineered antibodies." Molecular biotechnology 26.1 (2004): 39-60. (Year: 2004).*

* cited by examiner

*Primary Examiner* — Michael Szperka
*Assistant Examiner* — Lia E Taylor
(74) *Attorney, Agent, or Firm* — Thomas | Horstemeyer, LLP

(57) ABSTRACT

Infection with obligatory intracellular bacteria is difficult to treat as intracellular targets and delivery methods of therapeutics are not well-known. *Ehrlichia* translocated factor-1 (Etf-1), a type IV secretion system (T4SS) effector, is a primary virulence factor for an obligatory intracellular bacterium, *Ehrlichia chaffeensis*. Disclosed herein are Etf-1-specific nanobodies (Nbs) that block Etf-1 functions and *Ehrlichia* infection. Also disclosed is a method for treating human monocytic ehrlichiosis (HME) in a subject with the disclosed nanobodies.

7 Claims, 28 Drawing Sheets

Specification includes a Sequence Listing.

| | CDR3 | CDR3 length (aa) | |
|---|---|---|---|
| N115 | EDTVVYYCAADFKDYY-----DLAPRGFDYWGQGTQVTVSS | 17 | SEQ ID NO:1 |
| N51 | EDTAVYYCAADRYYYCSDSGPGGPIYEYDFRGQGTQVTVSS | 22 | SEQ ID NO:2 |
| N113 | EDTAVYYCAAPFRL-G---RRTWSPDDFDSWGQGTQVTVSS | 19 | SEQ ID NO:3 |
| D16 | EDTAVYYCAVLRDGAS----DHRRQSDYSIWGQGTQVTVSS | 18 | SEQ ID NO:4 |
| D30 | EDTAVYYCALLRDGAS----DHRRQSDYSIKGQGTQVTVSS | 18 | SEQ ID NO:5 |
| D53 | EDTAVYHCAALRDGAS----DHTRESDYNIWGQGTQVTVSS | 18 | SEQ ID NO:6 |
| N111 | EDTAVYYCNARGSSW---------QEEYWGQGTQVTVSS- | 11 | SEQ ID NO:7 |
| N55 | EDTAVYYCAAREFGYTG---GVSRFIDDYDYWGQGTQVTVSS | 20 | SEQ ID NO:8 |
| D4 | EDTAVYYCAAREFGYTG---GVSQFISDYDYWGQGTQVTVSS | 20 | SEQ ID NO:9 |
| N23 | EDTAVYYCAAREFGYTA---GISRFISDYDYWGQGTQVTVSS | 20 | SEQ ID NO:10 |
| N59 | EDTAVYYCAAQEFGYTA---GVSRFISDYDYWGQGTQVTVSS | 20 | SEQ ID NO:11 |
| D25 | EDTAVYYCAAQEFGYTG---GVSRFISDYDYWGQGTQVTVSS | 20 | SEQ ID NO:12 |
| D64 | EDTAVYYCAAREFGYTG---GISRAISDYDYWGQGTQVTVSS | 20 | SEQ ID NO:13 |
| N38 | EDTAVYYCAAREFGYTG---GISQFISDYDYWGQGTQVTVSS | 20 | SEQ ID NO:14 |
| N71 | EDTAVYYCAAQEFGYTG---GISRAISDYDYWGQGTQVTVSS | 20 | SEQ ID NO:15 |
| D7 | EDTAVYYCAAQEFGYTG---GISRFISDYDYWGQGTQVTVSS | 20 | SEQ ID NO:16 |
| D51 | EDTAVYYCAGQEFGYTG---GISRFISDYDYWGQGTQVTVSS | 20 | SEQ ID NO:17 |
| D12 | EDTAVYYCAAQEFGYTG---GISRFISDYDYWGQGTQVTVSS | 20 | SEQ ID NO:18 |
| N26 | EDTAVYYCAAQEFGYTG---GISRFISDYDYWGQGTQVTVSS | 20 | SEQ ID NO:19 |
| D3 | EDTSVYYCAAST----P---PIRTIPNTYDYWGQGTQVTVSS | 20 | SEQ ID NO:20 |
| D32 | EDTSVYYCAVKT----N---GNLYYASVDYWGQGTQVTVSS | 16 | SEQ ID NO:21 |
| D1 | EDTSVYYCAART----N---GNLYYASAYEYWGQGTQVTVSS | 16 | SEQ ID NO:22 |
| D29 | EDTSVYYCAART----N---GNLYYASVDYWGQGTQVTVSS | 16 | SEQ ID NO:23 |
| D15 | EDTSVYYCAART----N---GNLYYASAYDYWGQGTQVTVSS | 16 | SEQ ID NO:24 |

FIG. 1B

| Etf-1: | 1  67              14  23 25 | 132  158 | 307  327 | |
|---|---|---|---|---|
| 1-380 | MLTFLKKGANVVIKAAITPTTSKLP | Coil1 | Coil2 | SEQ ID NO:25 |
| 1-306 | MLTFLKKGANVVIKAAITPTTSKLP | | | SEQ ID NO:25 |
| ΔCoil1 | MLTFLKKGANVVIKAAITPTTSKLP | | | SEQ ID NO:25 |
| K6,7A | MLTFLAAGANVVIKAAITPTTSKLP | | | SEQ ID NO:26 |
| 21-380 | TSKLP | | | SEQ ID NO:27 |
| 21-380/K23A | TSALP | | | SEQ ID NO:28 |
| 22-380 | SKLP | | | SEQ ID NO:29 |
| 23-380 | KLP | | | |
| 25-380 | P | | | |

FIG. 3A

INTRACELLULAR NANOBODY TARGETING T4SS EFFECTOR INHIBITS EHRLICHIA INFECTION

CROSS-REFERENCE TO RELATED APPLICATIONS

This application claims benefit of U.S. Provisional Application No. 63/168,652, filed Mar. 31, 2021, which is hereby incorporated herein by reference in its entirety.

STATEMENT REGARDING FEDERALLY SPONSORED RESEARCH OR DEVELOPMENT

This invention was made with Government Support under Grant No. A1146736 awarded by the National Institutes of Health. The Government has certain rights in the invention.

SEQUENCE LISTING

This application contains a sequence listing filed in electronic form as an ASCII.txt file entitled "321501-1900 Sequence Listing_ST25" created on Mar. 14, 2022 and having 35,432 bytes. The content of the sequence listing is incorporated herein in its entirety.

BACKGROUND

Human monocytic ehrlichiosis (HME), one of the most prevalent, life-threatening, and emerging tick-borne diseases in the US is caused by infection with *Ehrlichia chaffeensis*, an obligatory intracellular bacterium in the order Rickettsiales. *E. chaffeensis* replicates within human monocytes-macrophages and causes severe flu-like symptoms accompanied by hematologic abnormalities and hepatitis. Currently the only HME therapy is the broad-spectrum antibiotic doxycycline, which is effective only if initiated early because delayed initiation, e.g., because of misdiagnosis can lead to severe complications or death. Also, doxycycline is contraindicated for pregnant women and children or those with drug allergies. The presence of underlying illness or injury, immunosuppression, and/or co-infection with other tick-borne pathogens can similarly lead to severe complications or death. No vaccine exists for HME. Tick-borne diseases have risen dramatically in the past 20 years and continue to rise, underscoring the importance of developing new therapeutic approaches and preventive measures.

SUMMARY

Disease-relevant targets of infection by obligatory intracellular pathogens are beyond the reach of conventional antibodies. The neutralizing targets of intracellular pathogens in host cells are mostly unknown. The present study attempted to overcome these limitations with a combination of nanobodies (Nbs), transfection, and a novel cell-permeable peptide delivery method to inhibit infection and determine inhibitory mechanisms. *Ehrlichia chaffeensis* uses the type IV secretion system to deliver bacterial effector Etf-1 to establish intracellular infection. As disclosed herein, a Nb can specifically block Etf-1 functions and thereby block *E. chaffeensis* infection in cell culture and in a mouse model, suggesting that this approach can be developed as a therapeutic intervention for human monocytic ehrlichiosis and other diseases caused by intracellular infections.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B show phylogenetic analysis and CDR3 alignment of anti-Etf-1 Nbs. FIG. 1A shows phylogenetic analysis of 24 distinct anti-Etf-1 Nbs based on their CDR3 amino acid sequences. Redundancy and family classification are shown on the right. FIG. 1B shows amino acid sequence alignment of anti-Etf-1 Nbs. The number of amino acids in each CDR3 is shown on the right.

FIGS. 2A to 2C show RF/6A cells were transfected with plasmids expressing Etf-1-GFP (FIG. 2A) or co-transfected with Etf-1-GFP and HA-tagged D7 (FIG. 2B) or D3 (FIG. 2C). At 2 dpt, cells were fixed, and mitochondria were labeled with mouse anti-cytochrome c (CytoC). Etf-1-GFP was labeled with rabbit anti-Etf-1. DAPI/DIC, the image stained with DAPI was merged with the differential interference contrast (DIC) image. N, nucleus. Each boxed area in the merged image was enlarged 3× on the right. White arrows: colocalization, Open arrow: lack of colocalization. Scale bar, 10 μm. FIG. 2D show quantification of effects of Nbs on Etf-1-GFP localization with mitochondria. Data were obtained by counting ~100 RF/6A cells from three independent experiments showing expression of Etf-1-GFP and D7-HA or D3-HA and represented as the mean±standard deviation (n=3). *$P<0.05$ by one-way ANOVA.

FIGS. 3A and 3B show K23 within the N-terminal 24 aa of Etf-1 is critical for mitochondrial targeting. FIG. 3A shows domains and mutations of Etf-1 plasmid constructs showing truncations, internal deletions, and point mutations of Etf-1. The N-terminal 25 amino acids are indicated, with K (lysine) residues shown in red and point mutations of K to alanine (A) in aqua. ΔCoil1, internal deletions of the first coiled-coil domain (amino adds 132-158); K6,7A, double mutations of K at residues 6 and 7 to A of full length Etf-1; 21-380/K23A, deletion of the N-terminal 20 aa with point mutation of K at residue 23 to A. Box, putative T4SS secretion motif. Protein lengths are not drawn to scale. FIG. 3B shows percentage of cells with Etf-1-GFP localized to mitochondria. RF/6A cells were transfected with plasmids expressing full-length (1-380 aa) or mutant Etf-1-GFP, and mitochondria were labeled with anti-cytochrome cat 2 dpt. Etf-1-GFP localization with mitochondria in ~100 cells each from three independent experiments was scored. Data are represented as the mean±standard deviation (n=3). *$P<0.05$ by one-way ANOVA.

FIG. 4A shows purified full-length (FL) and various N-terminal truncations of rEtf-1 (ΔN25, residues 26-380; ΔN50, residues 51-380; ΔN79, residues 80-380; and ΔN112, residues 113-380) were subjected to SDS-PAGE, and proteins were stained by Coomassie blue. BSA was used as a negative control, and D3 and D7 were also stained to verify their purity. MW, molecular weight marker. FIG. 4B shows far-western blotting. Proteins separated by SDS-PAGE as in FIG. 4A were transferred onto PVDF membranes. Proteins were denatured, renatured, and incubated with purified D7-HA or D3-HA. The binding of D7 or D3 to Etf-1 was detected with anti-HA. Molecular weight is indicated in kilodaltons (kDa).

FIG. 5A shows recombinant Etf-1, D3/D7, or Etf-1-D7/D3 complexes separated by size exclusion chromatography. Fractions (numbered and shown in red in the lower panels) corresponding to the elution peaks indicated by the absorbance at 280 nm were collected, and proteins in each fraction were subjected to SDS-PAGE and Coomassie blue staining (upper panels). Boxes show the eluted stable Etf-1 and Nb complex. MW, molecular weight (indicated in kDa). FIG. 5B shows binding affinity of D7 and D3 to Etf-1 was determined by OpenSPR. A series of five dilutions of Nbs was used to test their binding against biotinylated Etf-1 immobilized on a sensor chip. Lines are signals detected by OpenSPR, thin black lines are fitted models generated by the TraceDrawer software.

FIG. 6A are images showing the localization of Etf-1 and Nbs, and nuclear morphology was stained by DAPI (arrows, apoptotic nuclei; open arrows, non-apoptotic nuclei). Merged, the fluorescent image of DAPI channel merged with the DIC image. FIG. 6B show quantification of apoptosis (nuclear fragmentation) in 100 cells expressing transfected genes from three independent experiments. Data are represented as the mean±standard deviation (n=3). *P<0.05, by one-way ANOVA.

FIGS. 7B and 7C show quantification of relative band densities of MnSOD (FIG. 7B) and Etf-1 (FIG. 7C) normalized against ACTB. FIG. 7D show ROS production at 2 dpt was analyzed by the fluorescent indicator $H_2DCFDA$. Null, buffer control without $H_2DCFDA$. FIGS. 7B-7D show data presented as the mean±standard deviation from three independent experiments with triplicates per sample. *P<0.05, by one-way ANOVA.

FIGS. 8B, 8D, and 8E show quantification of relative densities of MnSOD (FIG. 8B), P28/OMP-1F (FIG. 8D), and Etf-1 (FIG. 8E) normalized against ACTB. FIG. 8C shows ROS production at 2 dpi was analyzed by the fluorescent indicator $H_2DCFDA$. Null, buffer control without $H_2DCFDA$. FIG. 8B to 8E are data presented as the mean±standard deviation from three independent experiments with triplicates per sample. *P<0.05, by one-way ANOVA.

FIG. 9A shows SDS-PAGE and Coomassie blue staining show that D7 and D3 were purified with >95% purity and that ~40% of Nbs were specifically conjugated with CPP12, as indicated by the band labeled with an asterisk. FIG. 9B shows RF/6A cells transfected with GFP or Etf-1-GFP, and treated with HA-labeled CPP-D7 or CPP-D3 for 12 h at 12 hpt. Cells were treated with 100 µM etoposide at 24 hpt for an additional 41 h and then were double labeled with mouse anti-cytochrome c (CytoC) and rabbit anti-Etf-1 or with mouse anti-GFP and rabbit anti-HA. N, nucleus by DAPI staining (solid arrows, apoptotic nuclei; open arrows, non-apoptotic nuclei). Scale bar, 10 µm. FIG. 9C shows quantification of the percentage of apoptotic cells (i.e., those showing nuclear fragmentation) among cells expressing Etf-1-GFP in the absence and presence of intracellularly delivered CPP-Nbs; 100 cells were analyzed for each condition in three independent experiments. FIG. 9D shows THP-1 cells infected with host cell-free E. chaffeensis for 2 h and then were incubated with 10 µM of CPP-D7 or CPP-D3 for 2 d. DNA was extracted from samples and qPCR was performed to amplify E. chaffeensis 16S rRNA gene normalized against with human actin gene (ACTB). FIGS. 9C and 9D show data represented as the mean±standard deviation (n=3); *P<0.05, by one-way ANOVA.

FIG. 11A shows the recombinant full-length Etf-1 protein (rEtf-1, 380 aa) was purified by gel filtration. The indicated peak fractions (fractions 9 and 10) were analyzed by SDS-PAGE and Coomassie blue staining. FIG. 11B shows Etf-1-specific antibody response of pre- and post-immune serum was analyzed by ELISA, and BSA was used as a negative control. Sera samples were prepared as four-fold serial dilutions. FIG. 11C shows Western blot analysis of the llama pre- and post-immune sera against recombinant and native Etf-1. Ech, cell lysate of E. chaffeensis-infected THP-1 cells at 3 dpi; THP-1, uninfected THP-1 cell lysate. Asterisk, recombinant and native Etf-1. Llama sera were pre-adsorbed using uninfected THP-1 cell lysates to reduce non-specific interacting bands.

FIG. 12A is an agarose gel electrophoresis of total RNA purified from PBLs of the Etf-1 protein-immunized llama. M, molecular weight marker (GeneRuler 1 kb Plus DNA Ladder). FIG. 12B is an agarose gel electrophoresis of the variable domains of all immunoglobulin heavy chains (VHs and VHHs) amplified from cDNA (VH+VHH, left) and Nb-encoding genes re-amplified from the gel-purified VH+VHH PCR products (VHH, right). FIG. 12C shows library size determination by serial dilutions shown as colonies on LB-agar plates (290 clones at $10^{-6}$ dilution). FIG. 12D shows colony PCR for assessing the percentage of clones in the library with the proper insert. Twenty-four isolated colonies were randomly picked from the transformants, and DNA was extracted from each. The amplicon size for clones with a Nb gene insert is ~700 bp. Transformants without a Nb gene insert have a smaller amplicon size (~350 bp).

FIG. 14A shows RF/6A cells transfected with plasmids expressing Etf-1-GFP (full-length, 1-380 aa), Etf-1(21-380/K23A)-GFP, or Etf-1(25-380)-GFP. At 28 h pt, cells were treated with 100 μm etoposide for 41 h. Cells were fixed by 4% PFA, and the host cell nuclei were stained with DAPI. Immunofluorscence labeling of RF/6A cells. DIC, differential interference contrast; arrows; apoptotic nuclei; open arrow; normal nuclei. Scale bar, 10 μm. FIG. 14B shows quantification of apoptosis (nuclear fragmentation) in 100 cells expressing transfected gene. Data are represented as the mean±standard deviation (n=3). * P<0.05 by one-way ANOVA.

FIG. 15A shows flow cytometry histograms showing intracellular levels of CPP-Nbs and of Nbs alone. There was a substantial increase in the fluorescence of cells incubated with CPP-Nb as compared with that of cells incubated with Nb or PBS with/without secondary antibody labeling. FIG. 15B shows cytotoxicity of CPP-Nbs, and PBS was measured using the MTT assay. Values are represented as the mean±standard deviation (n=3).

DETAILED DESCRIPTION

Figure 1A:
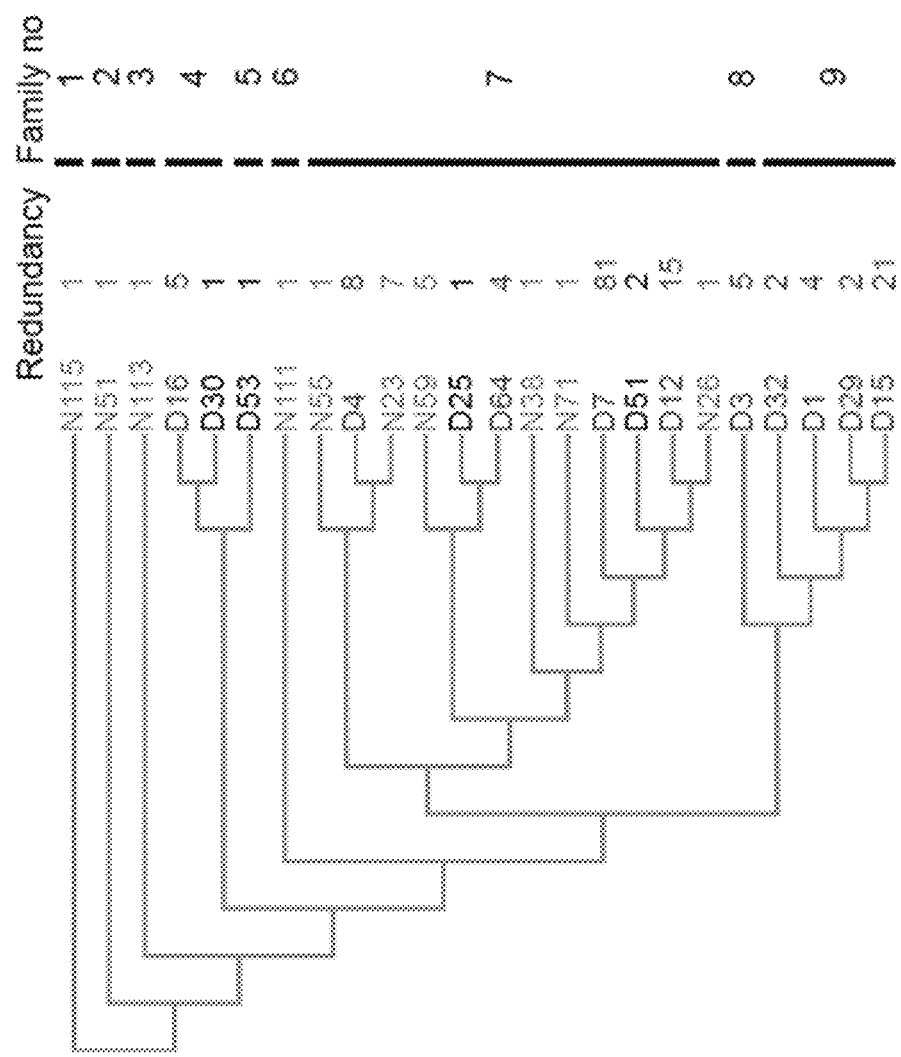
Figure 2A:
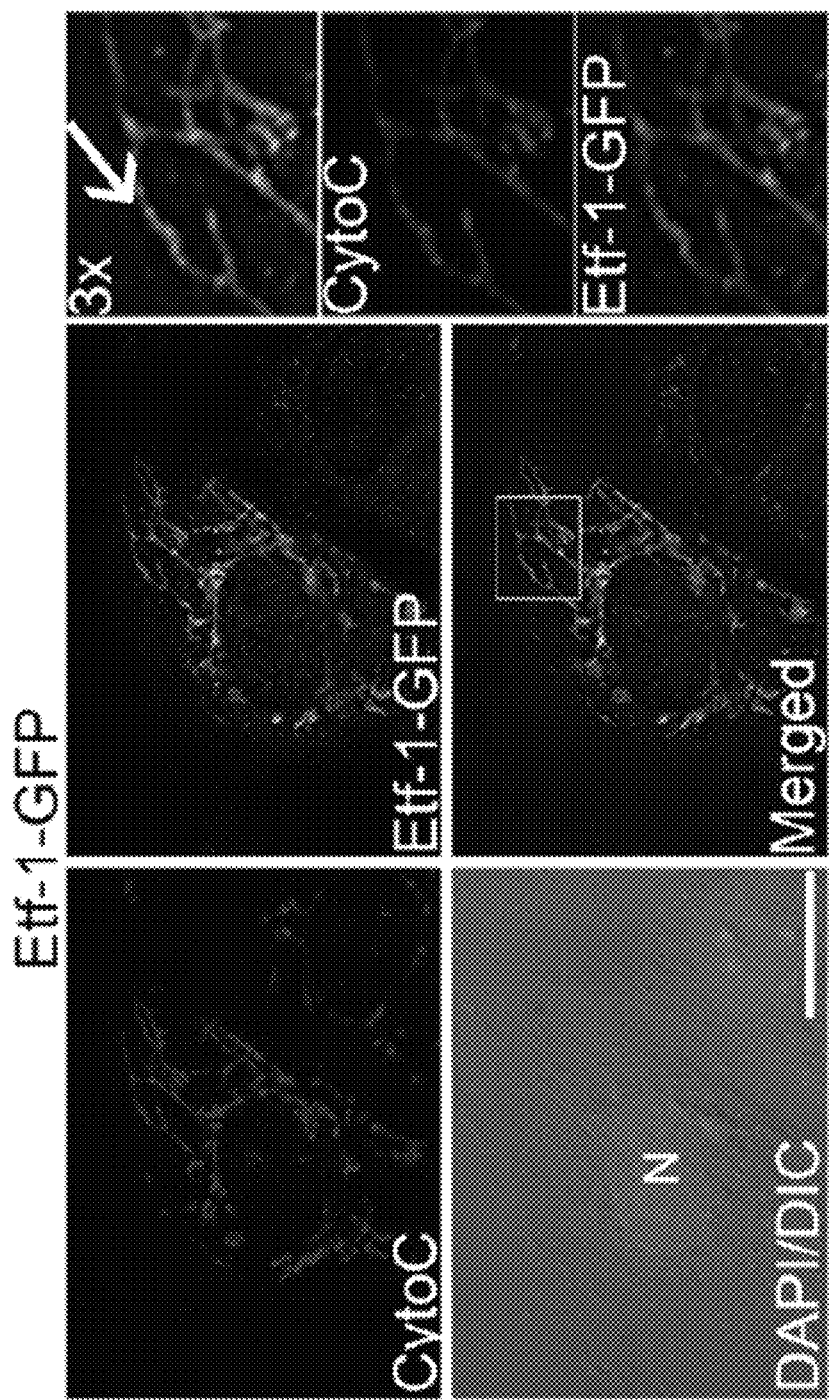
FIGS. 2A to 2D show NbD7, but not D3, blocks localization of Etf-1-GFP to mitochondria.
Figure 2B:
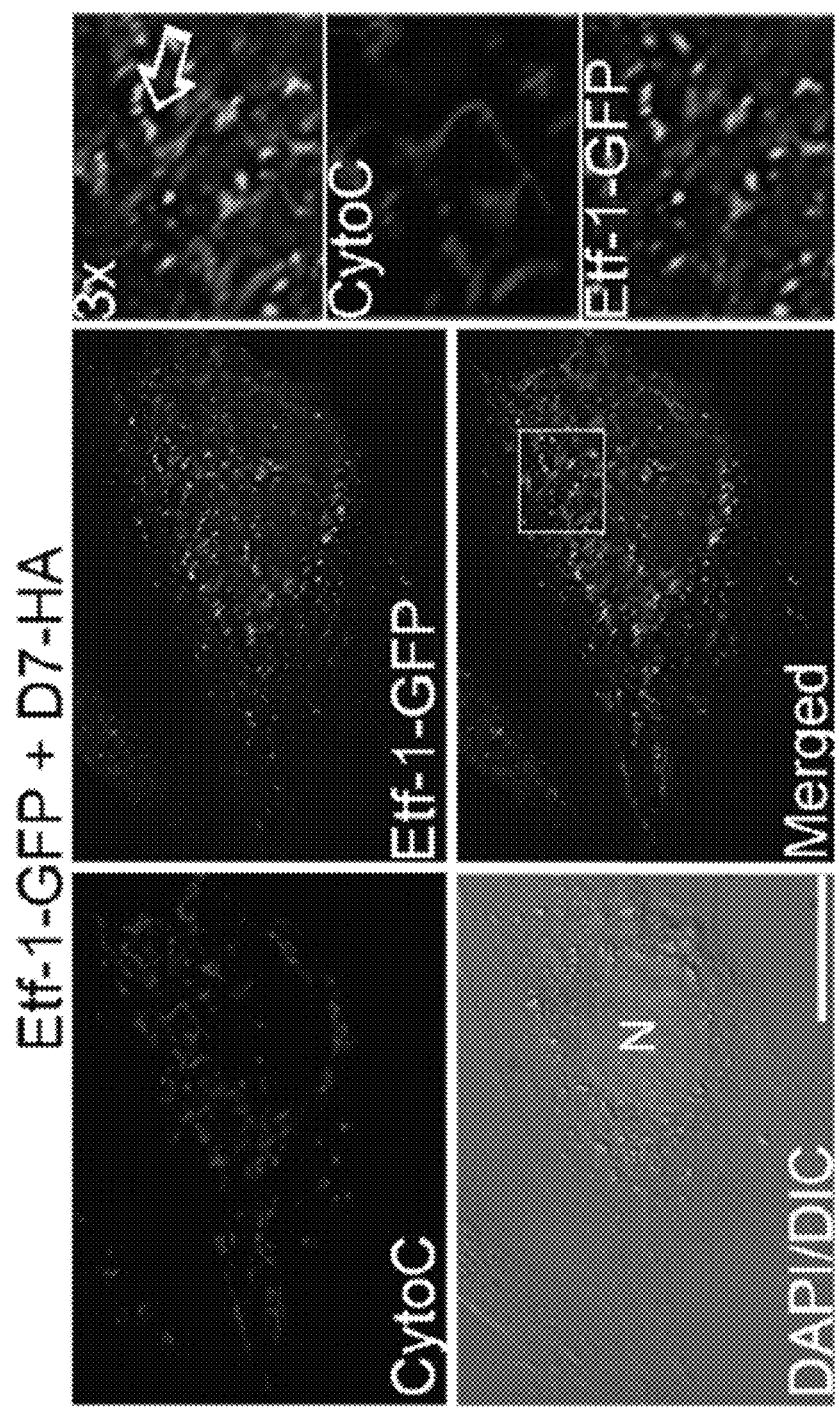
Figure 2C:
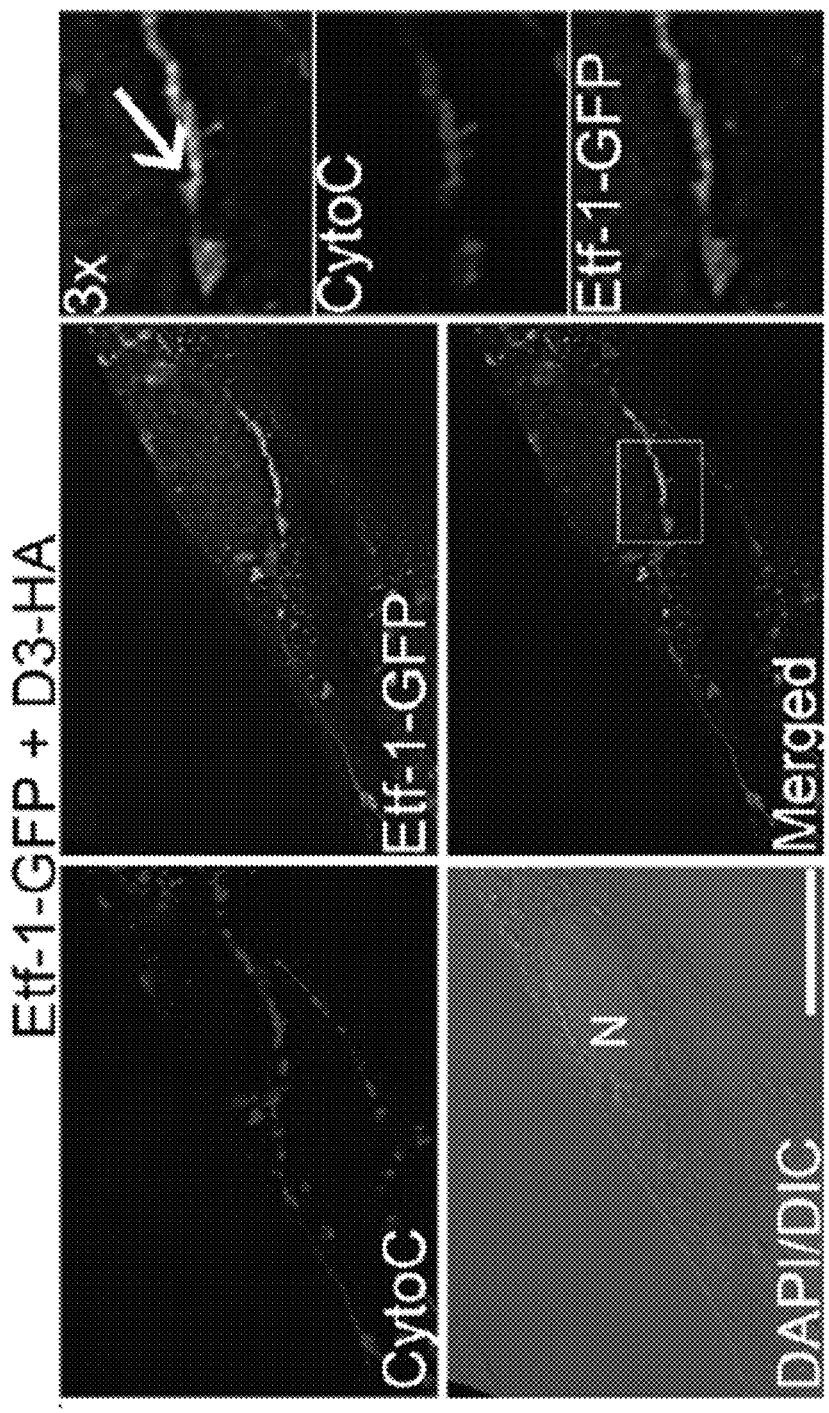
Figure 2D:
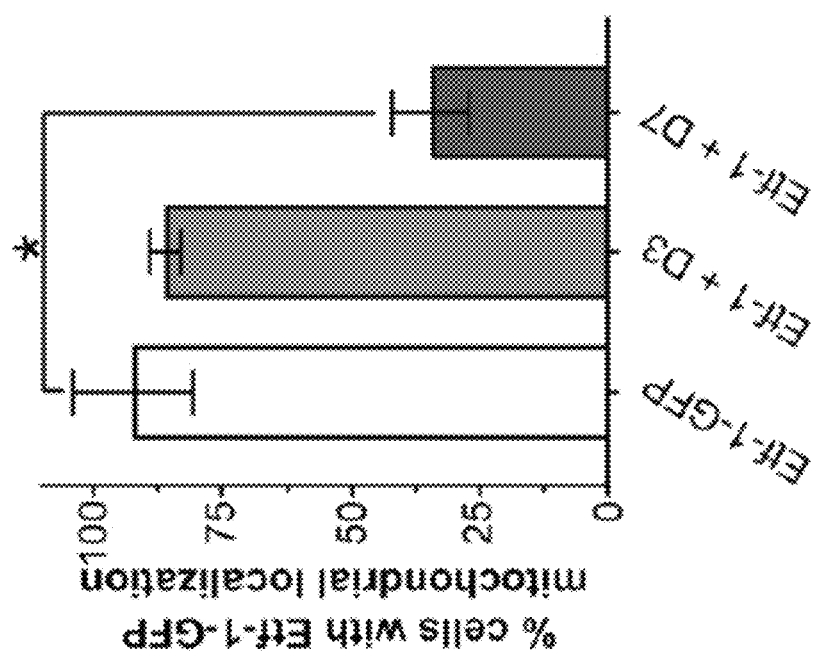

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

As used herein, the terms "single domain antibody (VHH)" and "nanobodies" have the same meaning referring to a variable region of a heavy chain of an antibody, and construct a single domain antibody (VHH) consisting of only one heavy chain variable region. It is the smallest antigen-binding fragment with complete function. The nanobody may be produced by any means. For instance, the nanobody may be enzymatically or chemically produced by fragmentation of an intact antibody, it may be recombinantly produced from a gene encoding the partial antibody sequence, or it may be wholly or partially synthetically produced.

The term "antigen binding site" refers to a region of an antibody that specifically binds an epitope on an antigen.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "specifically binds", as used herein refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "cell penetrating peptide", "cell penetrating protein", "CPP" and the like, as used herein, refer to a peptide or protein having an ability to pass through cellular membranes. In various embodiments, a CPP is conjugated to a nanobody disclosed herein to facilitate transport of the nanobody across the membrane. In some embodiments, a CPP is capable of being internalized into a cell and passing cellular membranes (including, inter alia, the outer "limiting" cell membrane (also commonly referred to as "plasma membrane"), endosomal membranes, and membranes of the endoplasmatic reticulum). In some embodiments, any possible mechanism of internalization is envisaged including both energy-dependent (i.e. active) transport mechanisms (e.g., endocytosis) and energy-independent (i.e. passive) transport mechanism (e.g., diffusion).

Nanobodies

Disclosed are compositions and methods for treating human monocytic ehrlichiosis (HME). In particular, nanobodies are disclosed that are able to inhibit *Ehrlichia* infection by inhibiting three activities of Etf-1 and *E. chaffeensis*: upregulation of mitochondrial manganese superoxide dismutase, reduction of intracellular reactive oxygen species, and inhibition of cellular apoptosis.

In some embodiments, the Etf-1-specific nanobody can comprise a variable domain having CDR1, CDR2 and CDR3 sequences. For example, in some embodiments, the CDR1 sequence comprises the amino acid sequence GGTLSSYT (SEQ ID NO:30); CDR2 sequence of the variable domain comprises the amino acid sequence VARVNGRI (SEQ ID NO:31); and the CDR3 sequence of the variable domain comprises the amino acid sequence AAQEFGYTGGISRAISDYDY (SEQ ID NO:32). In some embodiments, the nanobody has one or more conservative substitutions in SEQ ID NOs:30, 31, and/or 32. In some embodiments, the disclosed nanobody has the amino acid sequence: QVQLQESGGGLVQAGGSLRLSCTASGGTLSSYTMGWFRQAPGKERDFVATVARVNG RIYYADSVKGRFIISRDNAKNTVYLQMDSLKPEDTAVYYCAAQEFGYTGGISRAISDYDY WGQGTQVTVSS (SEQ ID NO:33), or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:33.

In the present invention, "a conservative substitution" refers to 1, 2, 3, 4, 5, or 6 amino acids substituted by amino acids having analogical or similar properties, compared to the amino acid sequence of the nanobody of the present invention. These conservative substitutions can, for example, be produced according to the amino acid substitutions in Table 1.

TABLE 1

Conservative Substitutions

| Original residue | substitution | substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Also disclosed herein is a fusion protein comprising the disclosed nanobodies or fragments thereof. In addition to almost full-length polypeptides, the present invention also includes fragments of the nanobodies of the invention. Typically, the fragment has at least about 50 contiguous amino acids of the disclosed nanobody, preferably at least about 50 contiguous amino acids, more preferably at least about 80 contiguous amino acids, and most preferably at least about 100 contiguous amino acids.

In some embodiments, the nanobody disclosed herein is conjugated to a cell penetrating peptide (CPP). Non-limiting examples of CPPs include the HIV-1 TAT translocation domain (Green; M. and Loewenstein, P. M. (1988) Cell 55, 1179-1188) and the homeodomain of the Antennapedia protein from *Drosophila* (Joliot; A. et al. (1991) Proc. Natl. Acad. Sci. USA 88, 1864-1868); a sequence of 16 amino acids called penetratin or pAntp of the Antennapedia protein (Derossi, D. et al. (1994) J. Biol. Chem. 269, 10444-10450); a basic sequence of the HIV-1 Tat protein (Vives, E. et al. (1997) J. Biol. Chem. 272, 16010-16017); and a synthetic peptide developed is the amphipathic model peptide MAP (Oehlke, J. et al. (1998) Biochim. Biophys. Acta 1414, 127-139). Additional non-limiting examples of CPPs are described in U.S. Pat. Nos. 9,303,076; and 9,302,014. Examples of linear CPPs are provided in Table 2.

TABLE 2

Linear CPPs

| | | |
|---|---|---|
| cpp1 | IRRGISRK | SEQ ID NO:61 |
| cpp2 | KRKRAV | SEQ ID NO:62 |
| cpp3 | PKPKRQTKR | SEQ ID NO:63 |
| cpp4 | RRRRHCNR | SEQ ID NO:64 |
| cpp5 | I PDPTGQS | SEQ ID NO:65 |
| cpp6 | IKREREND | SEQ ID NO:66 |
| cpp7 | KKLQEQEKQQKVEFRKR | SEQ ID NO:67 |
| cpp8 | GPNKKKRKL | SEQ ID NO:68 |
| cpp9 | RRRRASAPISQWSSSRRSR | SEQ ID NO:69 |
| cpp10 | KLALKLALKALKAALKLA | SEQ ID NO:70 |
| cpp11 | FLPLIGRVLSGIL | SEQ ID NO:71 |
| cpp12 | CVQWSLLRGYQPCCVQWSLLR GYQPC | SEQ ID NO:72 |
| cpp13 | RKKRKGSGSRKKRKGSGSRKK RKGSGSRKKRK | SEQ ID NO:73 |
| cpp14 | CVQWSLLRGYQPCGSGSCVQW SLLRGYQPC | SEQ ID NO:74 |
| cpp15 | KKRRRGSGSKKRRRGSGSKKR RRGSGSKKRRR | SEQ ID NO:75 |
| cpp16 | RKKRRGSGSRKKRRGSGSRKK RRGSGSRKKRR | SEQ ID NO:76 |
| cpp17 | RQIKIWFQNRRMKWKKC | SEQ ID NO:77 |
| [GRKRKRS]4 | GRKRKRSGRKRKRSGRKRKRS GRKRKRS | SEQ ID NO:78 |
| [PRKKRGR]4 | PRKKRGRPRKKRGRPRKKRGR PRKKRGR | SEQ ID NO:79 |
| CPP Motif 1 | CVQWSLLRGYQPC | SEQ ID NO:80 |
| CPP Motif 2 | XKXRX-GSGS, where X is R or K | SEQ ID NO:81 |
| 6xHis | HHHHHH | SEQ ID NO:82 |
| HIV-TAT | RKKRRQRRR | SEQ ID NO:83 |
| HIV-REV | RQARRNRRRRWR | SEQ ID NO:84 |
| NLS | PKKKRKV | SEQ ID NO:85 |
| dodecahistidine | HHHHHHHHHHHH | SEQ ID NO:86 |

In some embodiments, the CPP is a cyclic CPP. Examples of cyclic CPPs are described in US/20210070806, which is incorporated by references in its entirety for the teaching of these CPPs. In some embodiments, the cyclic CPP includes the amino acid sequence FϕR$_4$, where ϕ is L-2-naphthylalanine (SEQ ID NO:36). For example, in some embodiments, the CPP is CPP9, cyclo(fϕPRrRrQ) (SEQ ID NO:35) or CPP12, cyclo(FfϕRrRrQ) (SEQ ID NO:34), where ϕ is L-2-naphthylalanine, f is D-phenylalanine, and r is D-arginine. Additional examples of cyclic CPPs are provided in Table 3.

TABLE 3 cyclic CPPs

| CPP1 | cyclo(FΦRRRRQ) | SEQ ID NO:37 |
|---|---|---|
| CPP9 | cyclo(fΦRrRrQ) | SEQ ID NO:35 |
| CPP12 | cyclo(FfΦRrRrQ) | SEQ ID NO:34 |
| CPP1-1 | cyclo(FtBuRRRRQ) | SEQ ID NO:38 |
| CPP1-2 | cyclo(DapHexanRRRRQ) | SEQ ID NO:39 |
| CPP1-3 | cyclo(DapOctanRRRRQ) | SEQ ID NO:40 |
| CPP1-4 | cyclo(DapDecaRRRRQ) | SEQ ID NO:41 |
| CPP1-5 | cyclo(Dap1-PyrenRRRRQ) | SEQ ID NO:42 |
| CPP1-6 | cyclo(Dap3,3-diphenyRRRRQ) | SEQ ID NO:43 |
| CPP1-7 | cyclo(DapFmocRRRRQ) | SEQ ID NO:44 |
| CPP1-8 | cyclo(Dap1-PyrenebRRRRQ) | SEQ ID NO:45 |
| CPP1-10 | cyclo(DapDecaRrRrQ) | SEQ ID NO:46 |
| CPP1-11 | cyclo(DapDecarRrRQ) | SEQ ID NO:47 |
| CPP1-12 | cyclo(DapDecaARRRQ) | SEQ ID NO:48 |
| CPP1-13 | cyclo(DapDecaRRRAQ) | SEQ ID NO:49 |
| CPP1-14 | cyclo(DapDecaRRRRQ) | SEQ ID NO:50 |
| CPP1-15 | cyclo(LysDecaRRRRQ) | SEQ ID NO:51 |
| CPP1-16 | cyclo(DapDecaRRRQ) | SEQ ID NO:52 |
| CPP1-17 | cyclo(OrnDecaRRRRQ) | SEQ ID NO:53 |
| CPP1-18 | cyclo(LysDecaRrRrQ) | SEQ ID NO:54 |
| CPP1-19 | cyclo(LysDecarRrRQ) | SEQ ID NO:55 |
| CPP1-20 | cyclo(AspDecyRRRRQ) | SEQ ID NO:56 |
| CPP1-22 | cyclo(AspDecyRrRrQ) | SEQ ID NO:57 |
| CPP1-23 | cyclo(GluDecyRrRrQ) | SEQ ID NO:58 |
| CPP1-24 | cyclo(AspDecyrRrRQ) | SEQ ID NO:59 |
| CPP1-25 | cyclo(GluDecyrRrRQ) | SEQ ID NO:60 |

Φ, 2-naphthylalanine
tBu = tert-butanoyl,
hexan = hexanoyl,
octan = octanoyl,
deca = decanoyl,
1-pyren = pyrenol,
3,3-diphenyl = 3,3-diphenoyl,
Fmoc = fluorenylmethyloxycarbonoyl,
1-pyreneb = 1-pyrenylbutanoyl,
decy = decynoyl In some embodiments, the nanobody may be subjected to an alteration to render it less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining). Bispecific antibodies which have been altered will therefore remain administrable for a longer period of time with reduced or no immune response-related side effects than corresponding bispecific antibodies which have not undergone any such alteration(s). One of ordinary skill in the art will understand how to determine whether, and to what degree a nanobody must be altered in order to prevent it from eliciting an unwanted host immune response.

Also disclosed herein is a polynucleotide molecule encoding the above nanobody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Pharmaceutical Composition

Also disclosed is a pharmaceutical composition comprising a disclosed nanobody in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutically acceptable carriers include any and all suitable solvents, dispersion media, coatings, antibacterial and antifungal agents, isotonicity agents, antioxidants and absorption delaying agents, and the like that are physiologically compatible with a bispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical nanobody may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical nanobody may also comprise isotonicity agents, such as sugars, polyalcohols, such as mannitol, sorbitol, glycerol or sodium chloride in the compositions.

The pharmaceutical nanobody may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The bispecific antibodies may be prepared with carriers that will protect the bispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Also disclosed is the use of a disclosed nanobody for use as a medicament for the treatment of human monocytic ehrlichiosis (HME).

Methods of Treatment

Also disclosed is a method for treating human monocytic ehrlichiosis (HME) in a subject by administering to the subject a therapeutically effective amount of the disclosed pharmaceutical composition. HME is a rare infectious disease belonging to a group of diseases known as the Human Ehrlichioses. These diseases are caused by bacteria belonging to the "*Ehrlichia*" family. The onset of symptoms usually occurs about three weeks after an individual has been bitten by a tick carrying the bacterium *Ehrlichia chaffeensis*.

The symptoms of HME may include a sudden high fever, headache, muscle aches (myalgia), chills, and a general feeling of weakness and fatigue (malaise) within a few weeks after initial infection. In addition, in many cases, laboratory findings may indicate an abnormally low number of circulating blood platelets (thrombocytopenia), a decrease in white blood cells (leukopenia), and an abnormal increase in the level of certain liver enzymes (hepatic transaminases). In some individuals, symptoms may progress to include nausea, vomiting, diarrhea, weight loss, and/or confusion. If HME is left untreated, life-threatening symptoms, such as kidney failure and respiratory insufficiency, may develop in some cases. Human Monocytic Ehrlichiosis is caused by the bacteria *Ehrlichia chaffeensis* (or *E. chaffeensis*). *E. chaffeensis* is carried and transmitted by certain ticks (vectors), such as the Lone Star tick (*Amblyomma americanum*) and the American dog tick (*Dermacentor variabilis*).

HME may be diagnosed based upon a thorough clinical evaluation, characteristic findings, and specialized laboratory tests. Blood tests may reveal findings often associated with the Human Ehrlichioses such as abnormally low levels of blood platelets (thrombocytopenia), low levels of certain white blood cells (leukopenia), and/or elevated levels of certain liver enzymes (such as aspartate aminotransferase [AST] and alanine aminotransferase [ALT]). In some cases, laboratory tests may reveal abnormalities of the cerebrospinal fluid. In addition, chest X-rays may reveal abnormalities in the lungs (e.g., pulmonary infiltrates, increased fluid in the lungs).

Examination of blood smears under a microscope that uses an electron beam (electron microscopy) may reveal clusters of bacteria in membrane-bound cavities (vacuoles) within certain cells (e.g., monocytes); however, such clusters may not be apparent early in the course of infection. In some cases, additional specialized laboratory tests may then be conducted to help determine and/or to confirm a diagnosis of a specific bacterial infection.

Specialized laboratory tests may include Indirect Immunofluorescence Assays (IFA) conducted on the fluid portion of an affected individual's blood (serum). Antibodies, which are proteins manufactured by certain white blood cells, help the body fight toxins and invading microorganisms. In Indirect Immunofluorescence Assays, human antibodies are marked with special fluorescent dyes and a microscope with ultraviolet light is used, enabling researchers to observe antibody response to certain microorganisms.

IFA testing has been used in confirming a diagnosis of all known types of Human Ehrlichial infection. However, in Human Monocytic Ehrlichiosis (HME), the bacterium responsible for the infection (*Ehrlichia chaffeensis*) was not characterized and identified (isolated) until 1991. Therefore, for many years, HME infection was diagnosed by observing the antibody response in a patient's blood serum to the bacterium responsible for Canine Ehrlichiosis, *Ehrlichia canis*, a bacterium that is very genetically similar to *E. chaffeensis*. Since *E. chaffeensis* was isolated in 1991, cases of HME have been confirmed by IFA testing that measures antibody response either to *E. chaffeensis* itself or the closely-related *E. canis*.

Measurable diagnostic rises in antibody response to the *Ehrlichia* bacteria may not occur until approximately three weeks after the onset of Human Monocytic Ehrlichiosis. As a result, initial IFA blood serum results may be negative in some cases. Therefore, more sensitive testing techniques that can help establish early diagnosis may be used in some cases.

Polymerase Chain Reaction (PCR) conducted on certain bacterial DNA sequences obtained from patients' blood samples may confirm Human Ehrlichial infection due to a particular strain of *Ehrlichia*. PCR has been used to establish an early diagnosis of Human Ehrlichial infection in some cases of HME.

If HME is suspected, treatment should not be delayed until diagnosis has been confirmed by IFA testing, since a positive antibody response may not occur until several weeks after initial infection. Therapy should begin as soon as possible after the onset of symptoms.

In some embodiments, the method further involves administering to the subject standard doses of tetracycline antibiotics. Alternatively, doxycycline therapy may be administered. In severe cases of HME infection, hospitalization may be required. Other treatment is symptomatic and supportive.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for the disease. Thus, the method can further comprise identifying a subject at risk for the disease prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the nanobody is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The disclosed nanobodies may also be administered in combination therapy, i.e., combined with other therapeutic agents relevant for the disease or condition to be treated. Accordingly, in one embodiment, the antibody-containing medicament is for combination with one or more further therapeutic agent.

A number of embodiments of the invention have been described. Nevertheless, it will be understood that various modifications may be made without departing from the spirit and scope of the invention. Accordingly, other embodiments are within the scope of the following claims.

EXAMPLES

Example 1: An Intracellular Nanobody Targeting T4SS Effector Inhibits *Ehrlichia* Infection Introduction Human monocytic ehrlichiosis (HME), one of the most prevalent, life-threatening, and emerging tick-borne diseases in the US is caused by infection with *Ehrlichia chaffeensis*, an obligatory intracellular bacterium in the order Rickettsiales. *E. chaffeensis* replicates within human monocytes-macrophages and causes severe flu-like symptoms accompanied by hematologic abnormalities and hepatitis. Currently the only HME therapy is the broad-spectrum antibiotic doxycycline, which is effective only if initiated early because delayed initiation, e.g., because of misdiagnosis can lead to severe complications or death. Also, doxycycline is contraindicated for pregnant women and children or those with drug allergies. The presence of underlying illness or injury, immunosuppression, and/or co-infection with other tick-borne pathogens can similarly lead to severe complications or death. No vaccine exists for HME. Tick-borne diseases have risen dramatically in the past 20 years and continue to rise, underscoring the importance of developing new therapeutic approaches and preventive measures.

The type IV secretion system (T4SS) is conserved among all rickettsial organisms. The recent elucidation of critical roles of T4SS for *E. chaffeensis* and *Anaplasma phagocytophilum* infection may provide potential targets for new approaches against rickettsial diseases. For example, the T4SS effectors Ehrlichial translocated factors 1 and 2 (Etf-1 and Etf-2) are critical *E. chaffeensis* proteins secreted via T4SS into the host cell cytoplasm, as knockdown of Etf-1 or Etf-2 by transfection of *E. chaffeensis* with specific antisense peptide nucleic acids significantly inhibits *E. chaffeensis* infection. Secreted Etf-1 localizes to mitochondria and blocks mitochondria-mediated host cell apoptosis to keep the infected host cell alive for bacterial intracellular replication. A subpopulation of Etf-1 molecules that are not localized to mitochondria interacts with Beclin 1 (ATG6) and active Rab5 (Rab5-GTP), and induces Rab5-regulated autophagy for *E. chaffeensis* to acquire catabolites as nutrients. Etf-2 directly binds Rab5-GTP on *Ehrlichia*-containing inclusion membranes and blocks Rab5 GTPase activating protein (RabGAP-5) engagement with Rab5-GTP to prevent *Ehrlichia*-containing inclusions from maturing into late endosomes and fusing with lysosomes.

Camelidae produce two types of antibodies: conventional antibodies and heavy-chain-only antibodies. The variable domain of the heavy chain of heavy-chain-only antibodies (VHHs) of camelids are the smallest (11-15 kDa) antigen-binding fragment relative to conventional antibodies. VHHs are soluble and display long surface loops, which are often larger than those of conventional murine and human antibodies. The VHHs can be cloned into bacterial or mammalian expression plasmids to produce a nanobody (Nb), a monomeric variable antibody. VHHs cloned into mammalian expression vectors can produce intracellular Nbs within mammalian cells that are superior to conventional antibodies for modulating intracellular functions because they can operate in the reducing intracellular environment, are proteolytically stable, can target subcellular sites, can penetrate cavities in target antigens, and can bind efficiently to antigens such as enzyme catalytic sites. Although the therapeutic potential of Nbs has been investigated for several infectious diseases, the use of Nbs as a therapeutic agent against intracellular bacteria such as *E. chaffeensis* has not been reported. In the present study, an intracellular Nb approach was developed to block T4SS effectors within mammalian cells, thereby inhibiting intracellular pathogen infection.

Progress in developing effective therapy and investigative approach for obligatory intracellular pathogens has been hindered by many factors, not the least of which is the lack of safe and efficient intracellular delivery methods of macromolecules. Although cyclic peptides are generally unable to cross the cell membrane, some naturally occurring cyclic peptides (e.g., cyclosporine A) possess the unusual ability of crossing the cell membrane by passive diffusion and are orally bioavailable. Cyclized Arg-rich cell-permeable peptides (CPPs)—such as cFϕPR4, where ϕ is L-2-naphthylalanine—or newer and more effective CPPs (SEQ ID NO:36), such as CPP9 and CPP12, that include D-arginine and/or D-phenylalanine provide rapid and efficient cytosolic delivery of their linked cargo proteins into >95% of cells. They are not cytotoxic at effective concentrations and have oral and intravenous bioavailability based on preliminary pharmacokinetics in mice. The cyclic CPPs (and the CPP-cargo conjugates) bind directly to plasma membrane phospholipids and enter cells by endocytosis. They then efficiently escape from the early endosome into the cytosol unlike Tat, which escapes only from late endosomes.

In the present study, anti-Etf-1 Nbs were developed. A Nb was obtained that blocks Etf-1 functions and demonstrated its effectiveness in combination with a cyclic CPP for inhibition of *E. chaffeensis* infection in cell culture and in a mouse model. These findings represent a significant advance in developing therapeutic and investigative strategy of obligatory intracellular pathogens.

Results

Generation and characterization of anti-Eff-1 Nbs. To generate Etf-1-specific Nbs, a llama was immunized with soluble full-length recombinant Etf-1 protein (rEtf-1) immediately after purification by fast protein liquid chromatography (FPLC) (FIG. 11A). A strong antisera titer of $4\times10^{11}$ against rEtf-1 was detected by enzyme-linked immunosorbent assay (ELISA) after the third immunization (FIG. 11B). The serum from the immunized llama recognized both rEtf-1 and native Etf-1 from *E. chaffeensis*-infected THP-1 cells as demonstrated by Western blotting (FIG. 11C). For Nb library construction, cDNA was synthesized from total RNA extracted from peripheral blood leukocytes isolated from the llama after the third rEtf-1 immunization (FIG. 12A) and was used as a template for amplification of the Nb-encoding VHH regions by two-step PCR (FIG. 12B) as described previously with slight modification. A phagemid Nb library comprising $2.32\times10^{10}$ individual transformants was generated (FIG. 12C), of which 83% had the proper insert (FIG. 12D). The native Etf-1 protein synthesized by *E. chaffeensis* is assumed to be linearized when it passes through the two membranes of *E. chaffeensis* and one membrane of the *E. chaffeensis*-containing inclusion via the T4SS transmembrane channel, since the diameter of the inner channel is only 10 Å at the cytoplasm side. After the native Etf-1 protein is secreted into the cytoplasm of the host cell, it will be refolded back into its tertiary structure, as demonstrated in the type III secretion system. Thus, phages encoding anti-Etf-1 Nbs were enriched for by panning using non-denatured (folded) and denatured (linearized) rEtf-1 as antigen. After panning, 368 individual Nbs expressed by TG1—an amber codon suppression (supE) strain of *Escherichia coli*—were screened by ELISA. A total of 172 rEtf-1-binding phagemid clones (107 and 65 positive clones against non-denatured and denatured Etf-1, respectively) was obtained and used for DNA sequencing of the VHHs.

Complementarity-determining region 3 (CDR3), which is the most variable region within VHHs, was used for phylogenetic analysis. Alignment of the deduced CDR3 amino acid sequences of the 172 clones revealed clones encoding 24 Nbs with distinct CDR3 sequences (FIG. 1A, 1B). Ten Nbs bound to both denatured and non-denatured rEtf-1, 10 Nbs bound only to non-denatured rEtf-1, and four Nbs bound only to denatured rEtf-1 (FIG. 1A). Nbs with a high similarity in their CDR3 sequences (identical length and >80% amino acid sequence identity) are derived from the same B-cell clonal lineage and can be grouped into a single family. Based on this, 24 Nbs were grouped into nine different families (FIG. 1A).

NbD7 blocks mitochondrial localization of Etf-1. To determine whether anti-Etf-1 Nbs can block the mitochondrial localization of Etf-1, 24 Nbs were recloned into the mammalian expression vector pEGFP-C1 by replacing EGFP with a C-terminal hemagglutinin (HA) tag for intracellular Nb expression. Rhesus monkey RF/6A endothelial cells, which are thinly spread adherent cells and are thus suitable for cellular localization studies, were co-transfected with each Nb and Etf-1-GFP. Ectopically expressed Etf-1-GFP in RF/6A cells localizes to the mitochondria, which are visible as filamentous structures and colocalize with cytochrome c, a marker of mitochondria (FIG. 2A). Among 24 Nbs, only NbD7 (referred to hereafter as D7) unequivocally blocked Etf-1-GFP localization to mitochondria (FIGS. 2B and 2D), and NbD3 (referred to hereafter as D3) unequivocally did not block Etf-1-GFP localization to mitochondria (FIGS. 2C and D). Therefore, D7 and D3 were selected for detailed studies of intracellular Nb activities and mechanisms.

The N-terminal 24 aa of Etf-1 are critical for mitochondrial localization. Most eukaryotic mitochondria-targeting proteins are synthesized as precursor proteins in the cytosol and then are directed into mitochondria by one or more signal sequences. The position of the signal sequence in each precursor protein determines its destination in mitochondria. An N-terminal pre-sequence is required for many proteins entering the matrix and is rapidly removed by a signal peptidase in the mitochondrial matrix after import. In contrast, an internal signal sequence that is present on all proteins that target the mitochondrial outer membrane and several sequences that target the inner membrane or intermembrane space are required for their import and proper localization; these sequences are not removed. As D7 blocked Etf-1-GFP localization to mitochondria, the mitochondria localization signal sequence of Etf-1 was first examined.

Figure 3B:
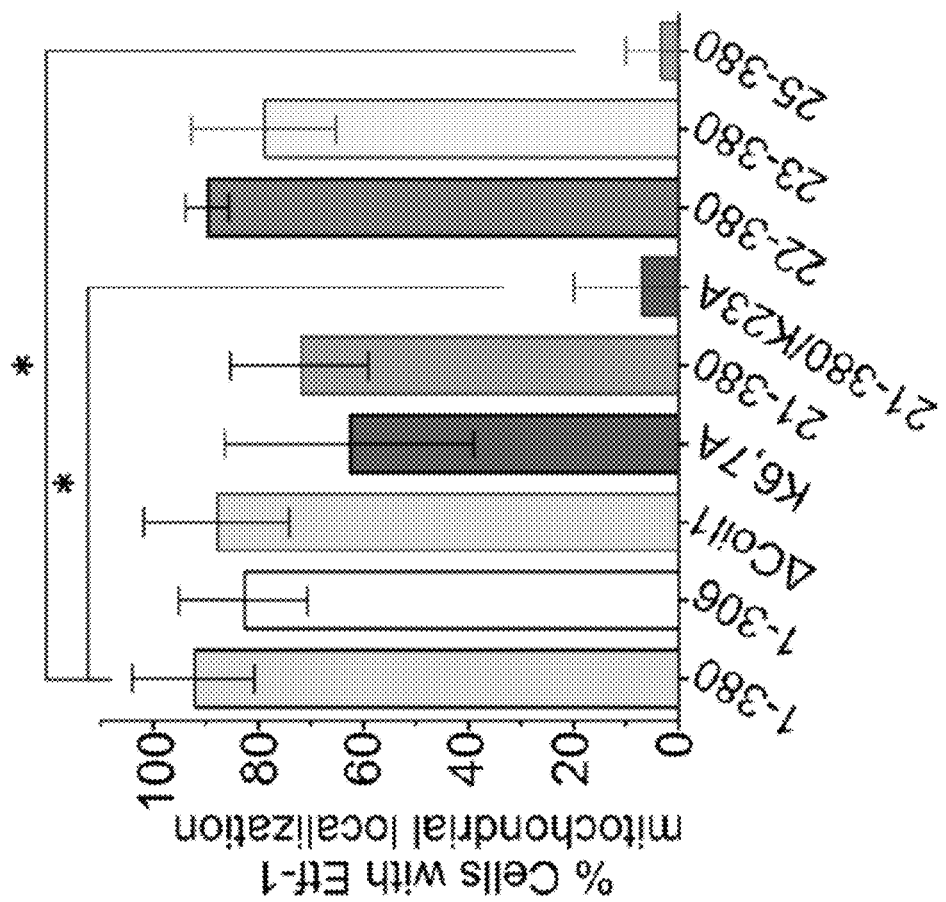
Figure 13:
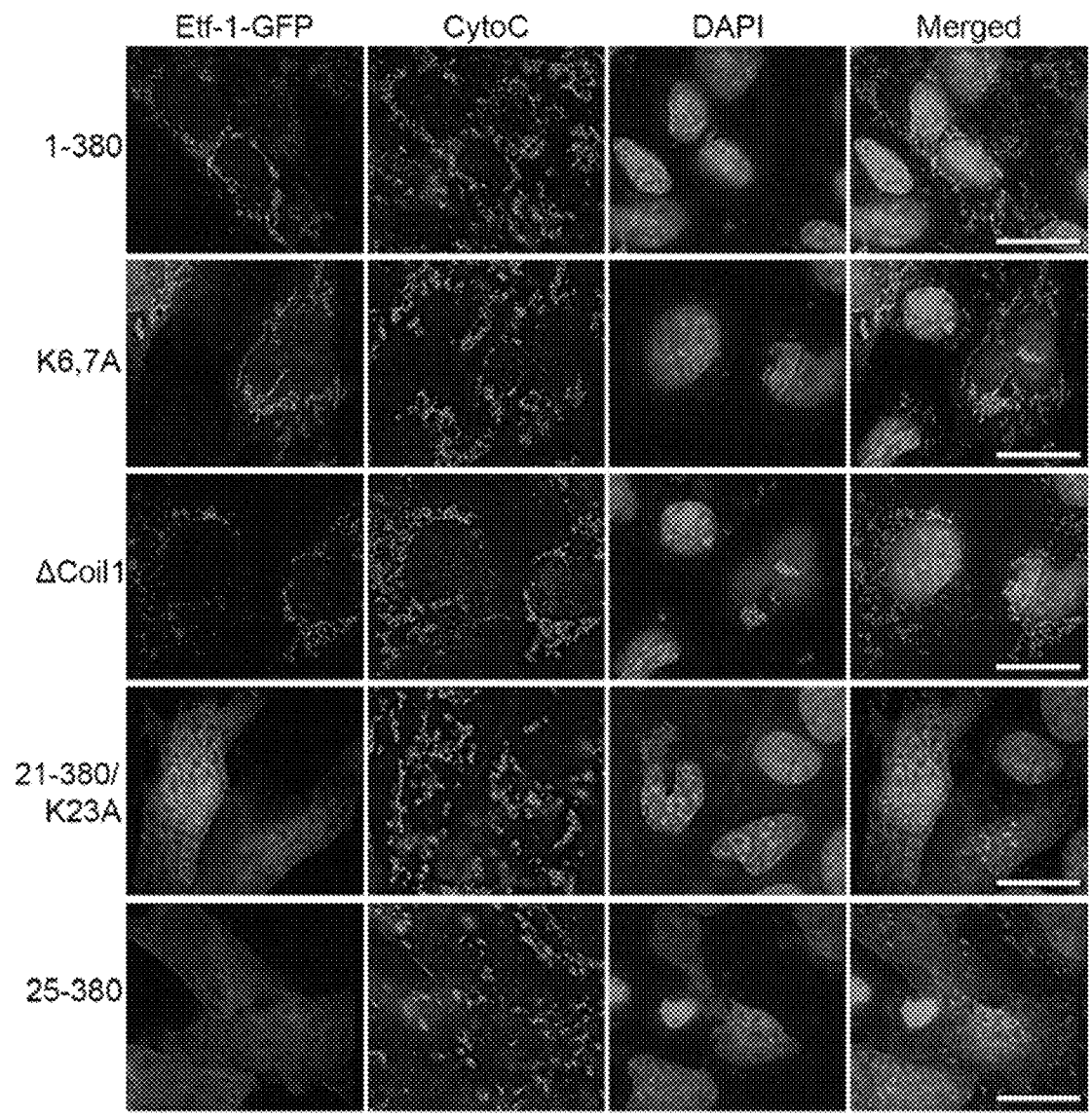
FIG. 13 shows K23 within the N-terminal 24 aa of Etf-1 is critical for mitochondrial targeting. Immunofluoresence labeling of RF/6A cells transfected with transfected with truncated, internal deletion, or point mutations of Etf-1-GFP (as described in FIG. 3). Cells were labeled with mouse monocloncal anti-cytochrome c (CytoC). Representative images show the presence (full-length, 1-380 aa; K6,7A; and ΔCoil1) and absence (21-380/K23A and 25-380 aa) of Etf-1 colocalization with mitochondria. Colocalization was quantified and is presented in FIG. 3. Scale bars: 15 μm.

To determine whether the N-terminus of Etf-1 is essential for mitochondrial localization, sequential truncation of the N-terminal 20 to 24 aa of Etf-1, in conjunction with internal deletions or point mutations, was carried out (FIG. 3A), and the resulting constructs were ectopically expressed in RF/6A cells to examine their mitochondrial localization by double immunofluorescence labeling. Etf-1-GFP (full-length Etf-1, 1-380 aa) was used as a positive control. C-terminal deletion (1-306 aa) or deletion of the first coiled-coil domain motif (ΔCoil1) of Etf-1 did not affect the mitochondrial localization as compared with Etf-1 (FIGS. 3B and 13). Etf-1 with the deletion of the N-terminal 24 aa (Δ1-24, 25-380 aa) resulted in the complete loss of mitochondrial localization (FIG. 3B and FIG. 13), whereas Etf-1 Δ1-20 (21-380 aa), Δ1-21 (22-380 aa), and Δ1-22 (23-380 aa) were targeted to mitochondria (FIG. 3B), indicating that the N-terminal amino acids 23 and 24 of Etf-1 are critical for Etf-1 targeting to mitochondria. N-terminal basic amino acids are known to be critical for mitochondrial targeting of proteins. As four lysine (K) residues are present at the N terminus of Etf-1, it was determined whether these lysine residues are critical for mitochondrial localization of Etf-1. Lysines at positions 6,7, and 23 of Etf-1 were individually point-mutated to alanine (A) and cloned into plasmid pGFP-N1 (FIG. 3A). The K6A, K7A double mutant of Etf-1 was constructed based on full-length Etf-1, whereas the K23A mutant was based on Etf-1 Δ1-20 (residues 21-380) (FIG. 3A). Ectopic expression of the K/A mutants of Etf-1 in RF/6A cells showed that the mitochondrial localization of Etf-1 was only slightly reduced by the K6A/K7A double-mutant but was completely abolished by Etf-1 Δ1-20 K23A (FIGS. 3B and 13). These results indicated that the N-terminal 24 aa of Etf-1, especially the positively charged residue K23, plays a critical role in mitochondrial targeting of Etf-1, as both deletion and mutation of this residue significantly decreased the percentage of cells with Etf-1 that was targeted to mitochondria (FIGS. 3B and 13).

Figures 4A, 4B:
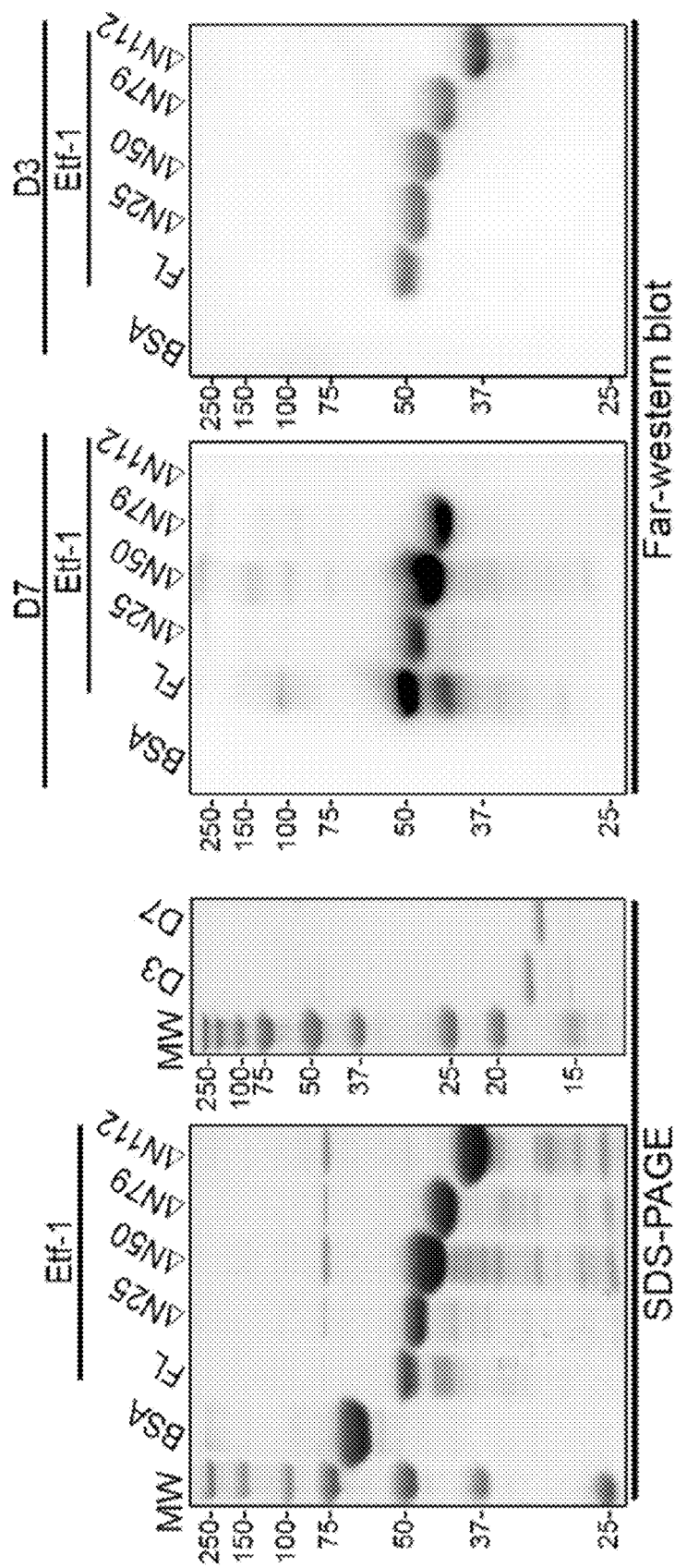
FIGS. 4A and 4B show D7 and D3 bind different regions of Etf-1.

Characterization of D7 and D3 binding to Etf-1. Using recombinant D7 and D3 and progressively truncated rEtf-1, Nb binding epitopes were determined by far-western blot analysis (FIGS. 4A and 4B). D7 bound to full-length and Etf-1 ΔN25, ΔN50. and ΔN79 (residues 26-380, 51-380, and 80-380, respectively) but not to Etf-1 Δ112 (residues 113-380) of Etf-1 protein (FIG. 4B). D3 bound to full-length and all four N-terminal-truncated Etf-1 proteins (FIG. 4B), indicating that the binding epitope of Etf-1 resides between residues 81 to 112 for D7 and between residues 113 to 380 for D3. Thus, inhibition of Etf-1 localization to mitochondria by D7 was not due to masking or blockade of the N-terminal Etf-1 mitochondria localization signal.

Figure 5A:
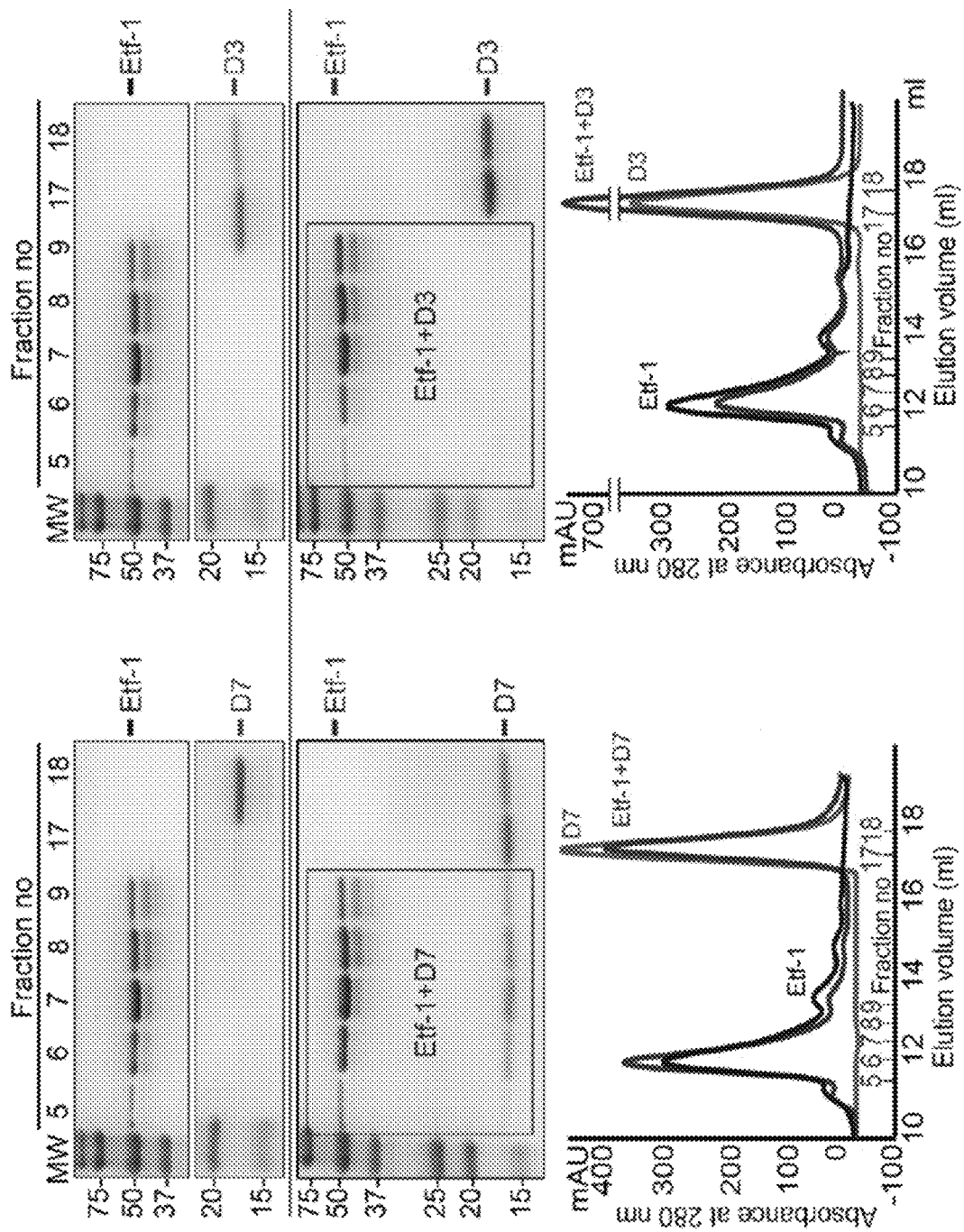
FIGS. 5A and 5B show D7 forms a more stable complex with Etf-1 than does NbD3.
Figure 5B:
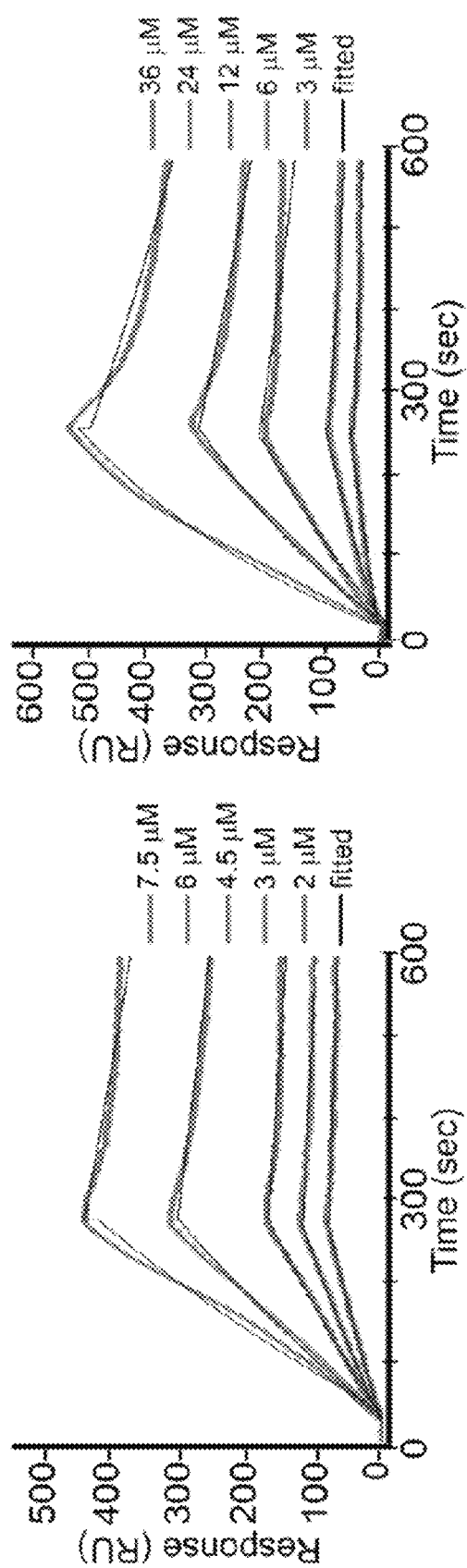

Next, size exclusion chromatography was used to determine the stability of the rEtf-1 and D7 complex. The analysis showed that D7 formed a more stable complex with rEtf-1 in solution, as indicated by the co-migration of the two proteins, than did D3 (FIG. 5A). By using Open Surface Plasmon Resonance (OpenSPR), it was determined that the dissociation constant of rEtf-1 and D7 was 3.15±0.07 µM, whereas that of rEtf-1 and D3 was 11.60±0.87 µM (FIG. 5B), consistent with the analytical size exclusion chromatography result. Thus, the stability of D7 binding to rEtf-1 likely results in steric misfolding or steric hindrance of Etf-1 that reduces its localization to mitochondria. In contrast, binding of D3 to Etf-1 is so unstable that it did not alter Etf-1 functions.

Figure 14B:
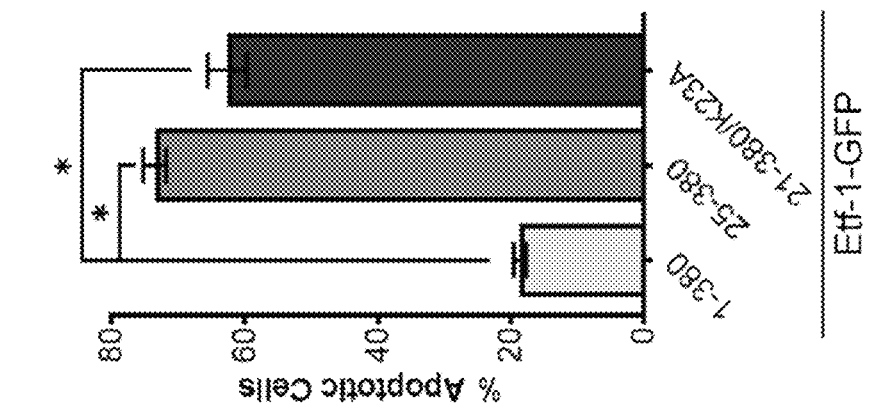
FIGS. 14A and 14B show K23 within the N-terminal 24 aa of Etf-1 is critical for inhibition of etoposide-induced apoptosis.
Figure 14A:
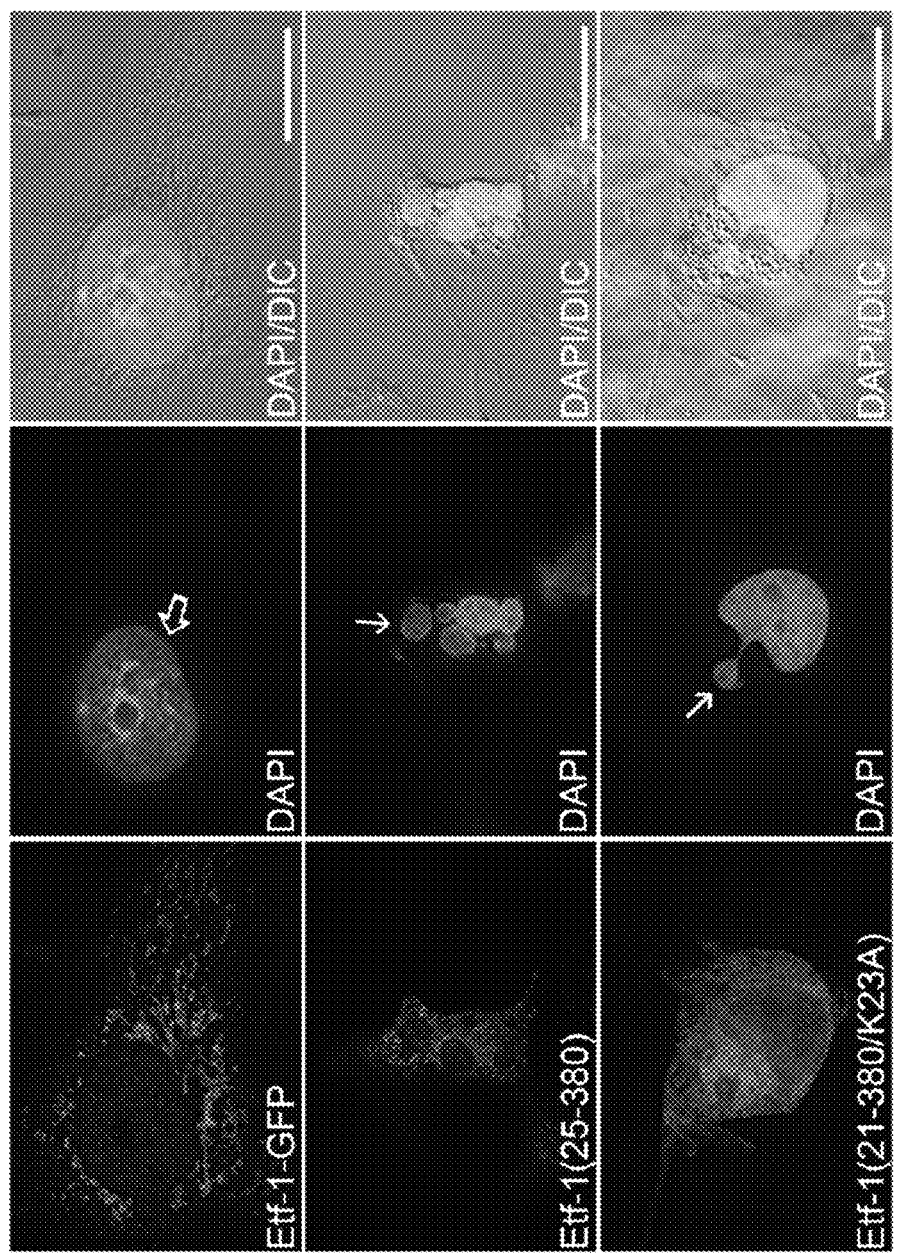

D7 abrogates Etf-1 inhibition of host cell apoptosis induced by etoposide. Etoposide, a topoisomerase II inhibitor, can induce DNA double-strand breaks that lead to the activation of caspase 2 and subsequent induction of Bax translocation to mitochondria and cytochrome c release, which results in apoptosis. Ectopically expressed Etf-1 localizes to mitochondria and inhibits mitochondria-mediated cellular apoptosis induced by etoposide, including Bax translocation to mitochondria, cytochrome c release, loss of mitochondrial membrane potential, nuclear fragmentation, as well as human Bax-induced yeast apoptosis. Since Etf-1 (25-380) truncation and Etf-1(21-380/K23A) mutant completely abolished their mitochondrial localization, it was examined whether these two Etf-1 mutants affect mitochondria-mediated cellular apoptosis induced by etoposide. The results showed that both Etf-1(25-380) and Etf-1(21-380/ K23A) mutants could not inhibit etoposide-induced apoptosis (FIG. 14), indicating that the mitochondrial localization of Etf-1 is essential for its inhibition of mitochondria-mediated cellular apoptosis.

Figures 6A, 6B:
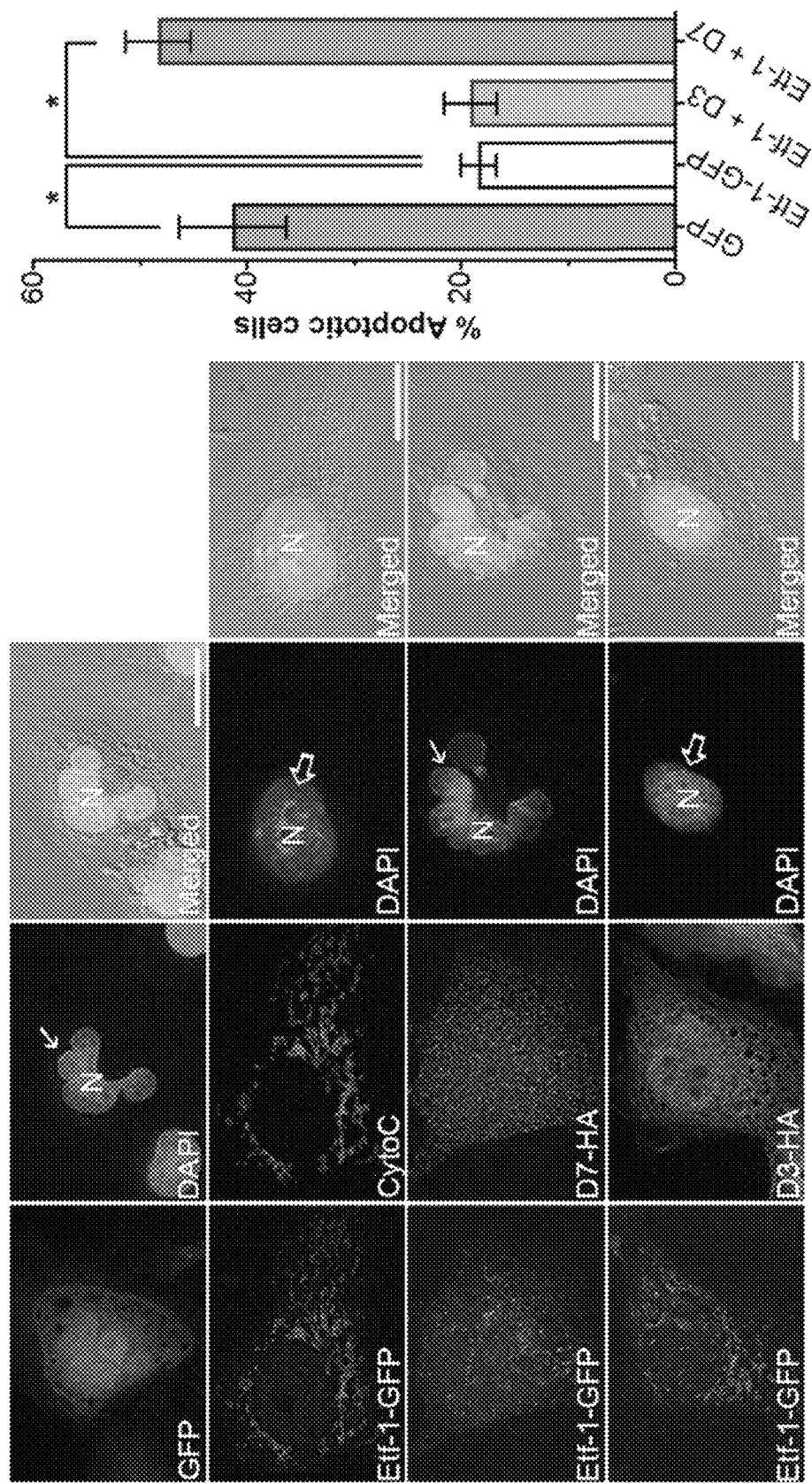
FIGS. 6A and 6B show D7 abrogates Etf-1 inhibition of etoposide-induced apoptosis. RF/6A cells were transfected with GFP or Etf-1-GFP, or co-transfected with Etf-1-GFP and D7 or D3, followed by treatment with 100 µM etoposide at 24 hpt for 41 h. Cells were labeled with mouse monoclonal anti-cytochrome c (CytoC) and rabbit polyclonal anti-Etf-1, or mouse monoclonal anti-GFP and rabbit monoclonal anti-HA.

Because D7 blocked Etf-1 targeting to mitochondria (FIG. 2), whether D7 abrogates Etf-1-mediated inhibition of apoptosis was examined. RF/6A cells co-transfected with Nb and Etf-1-GFP or GFP (as a negative control) were treated with 100 µM etoposide at 24 h post-transfection (hpt), and apoptotic cells were scored based on characteristic condensed or fragmented nuclei at 41 h (65 hpt) after etoposide treatment (FIGS. 6A and 6B). D7-HA transfection abrogated apoptosis inhibition induced by Etf-1-GFP, resulting in a level similar to that of GFP-transfected control cells (FIGS. 6A and 6B), whereas D3-HA transfection did not alter apoptosis inhibition induced by Etf-1-GFP (FIGS. 6A and B).

Figure 7A:
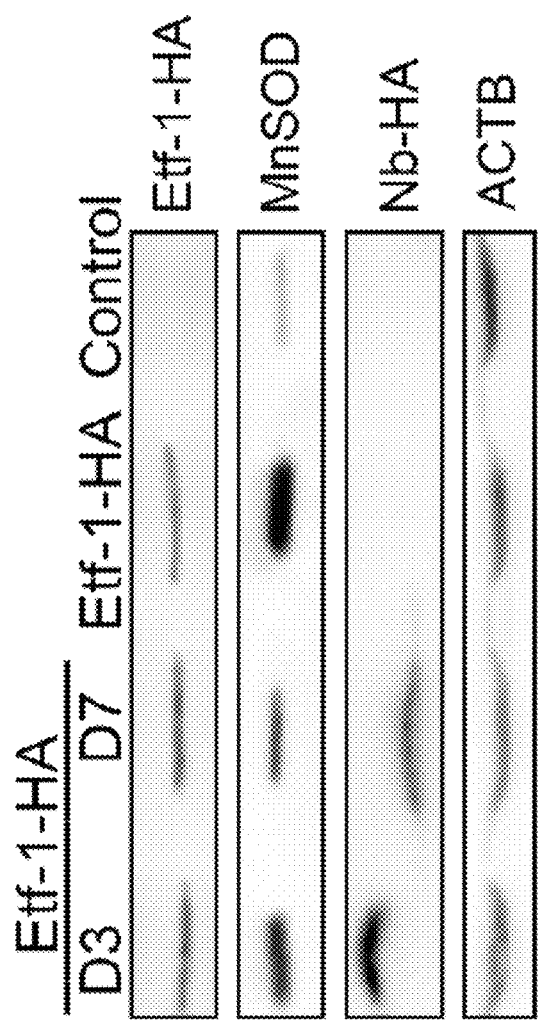
FIGS. 7A to 7D show D7, but not D3, abrogates the increase in MnSOD and attenuation of intracellular ROS generation by Etf-1. HEK293 cells were transfected with Etf-1-HA, or co-transfected with Etf-1-HA and D7 or D3. Control, untransfected cells. (A) At 2 dpt, cell lysates were subjected to western blotting using antibodies against HA, MnSOD, and human β-actin (ACTB).
Figure 7D:
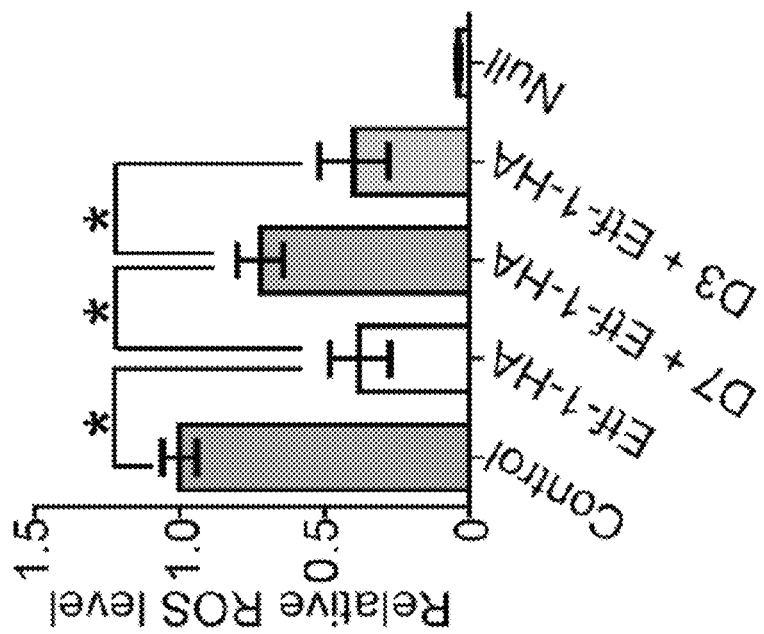
Figure 7C:
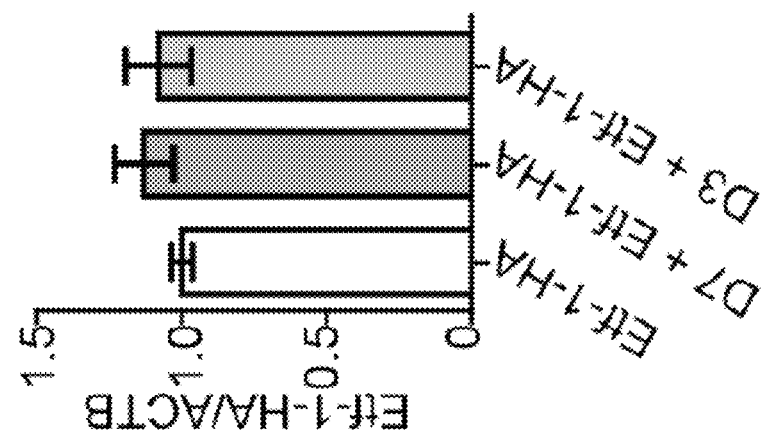
Figure 7B:
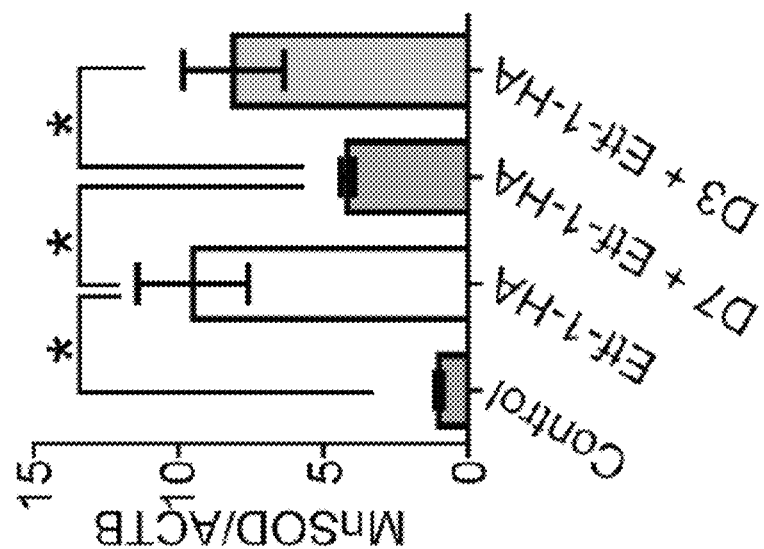

D7 abrogates the Etf-1-induced increase in Mn-superoxide dismutase (MnSOD) and decrease in cellular reactive oxygen species (ROS). During aerobic respiration to produce ATP from oxygen in mitochondria, toxic ROS are produced as 1-3% of electrons leak from the electron transport chain and interact with oxygen directly to yield superoxide. This leads to DNA damage and is a critical factor for inducing host cell apoptosis. To prevent oxidative damage to mitochondria and the cell, MnSOD and the glutathione/glutathione peroxidase-1 system in the mitochondrial matrix act cooperatively to reduce the levels of ROS produced during aerobic metabolism. A previous study showed that ectopically expressed Etf-1-GFP upregulates mitochondrial MnSOD at the protein level, but not at the mRNA level, and reduces intracellular ROS levels, consequently inhibiting cellular apoptosis induced by etoposide. Based on western blotting, D7, but not D3, lowered the level of MnSOD in cells transfected with Etf-1-HA (FIG. 7A-7C). By using 2',7'-dichlorodihydrofluorescein diacetate ($H_2$DCFDA), which can be oxidized by ROS to yield DCF, a fluorescent compound detectable by fluorescence spectrophotometry, whether D7 affects intracellular ROS levels was measured. ROS levels in *E. chaffeensis*-infected or Etf-1-transfected cells are lower than those in uninfected or untransfected cells, respectively, suggesting that Etf-1 in mitochondria reduces the ROS level in the host cells. D7, but not D3, abrogated ROS reduction induced by Etf-1-HA transfection (FIG. 7D). Thus, these results are in agreement with a previous prediction that not simply the intracellular presence of Etf-1 but specifically its mitochondrial localization is required for MnSOD upregulation and cellular ROS reduction.

Figure 8B:
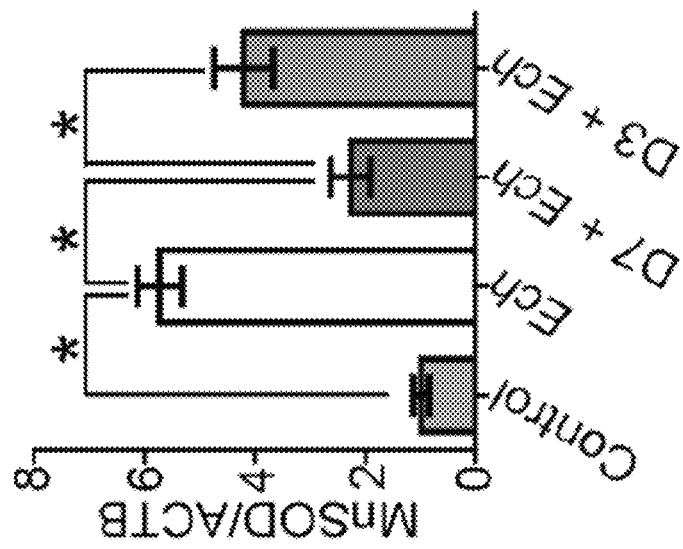
FIGS. 8A to 8E show D7, but not D3, abrogates E. chaffeensis-induced increase in MnSOD and reduction in ROS and inhibits infection. FIG. A) HEK293 cells were transfected with HA-tagged Nbs and infected with E. chaffeensis (Ech) at 1 dpt. Native E. chaffeensis Etf-1, E. chaffeensis outer membrane proteins P28/OMP-1F, Nbs, MnSOD, and human β-actin (ACTB) were detected at 2 dpi by western blotting using their respective antibodies.
Figure 8A:
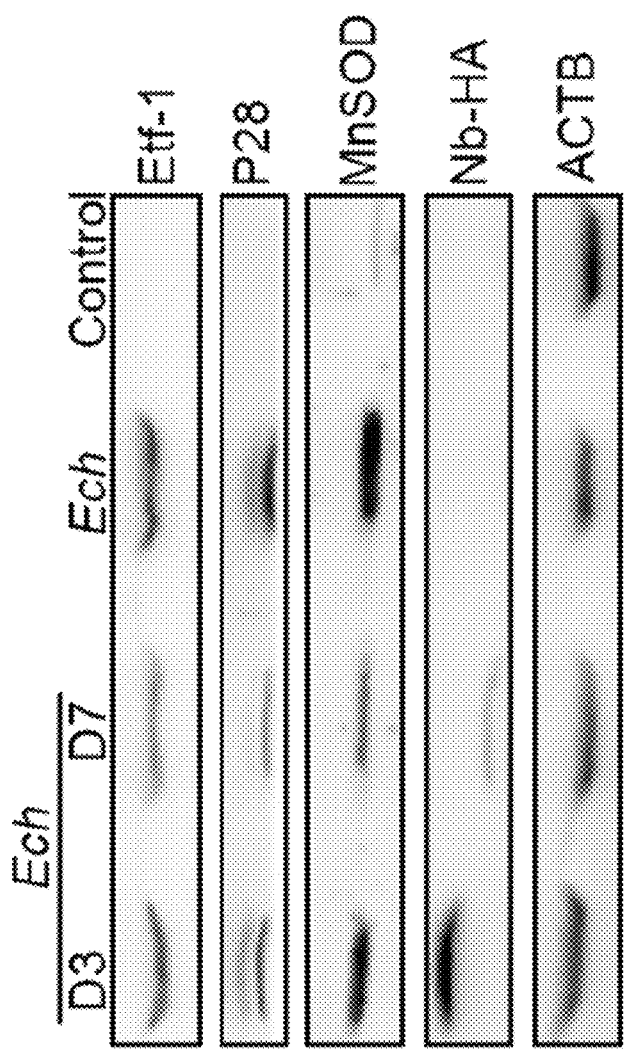
Figures 8C, 8D, 8E:
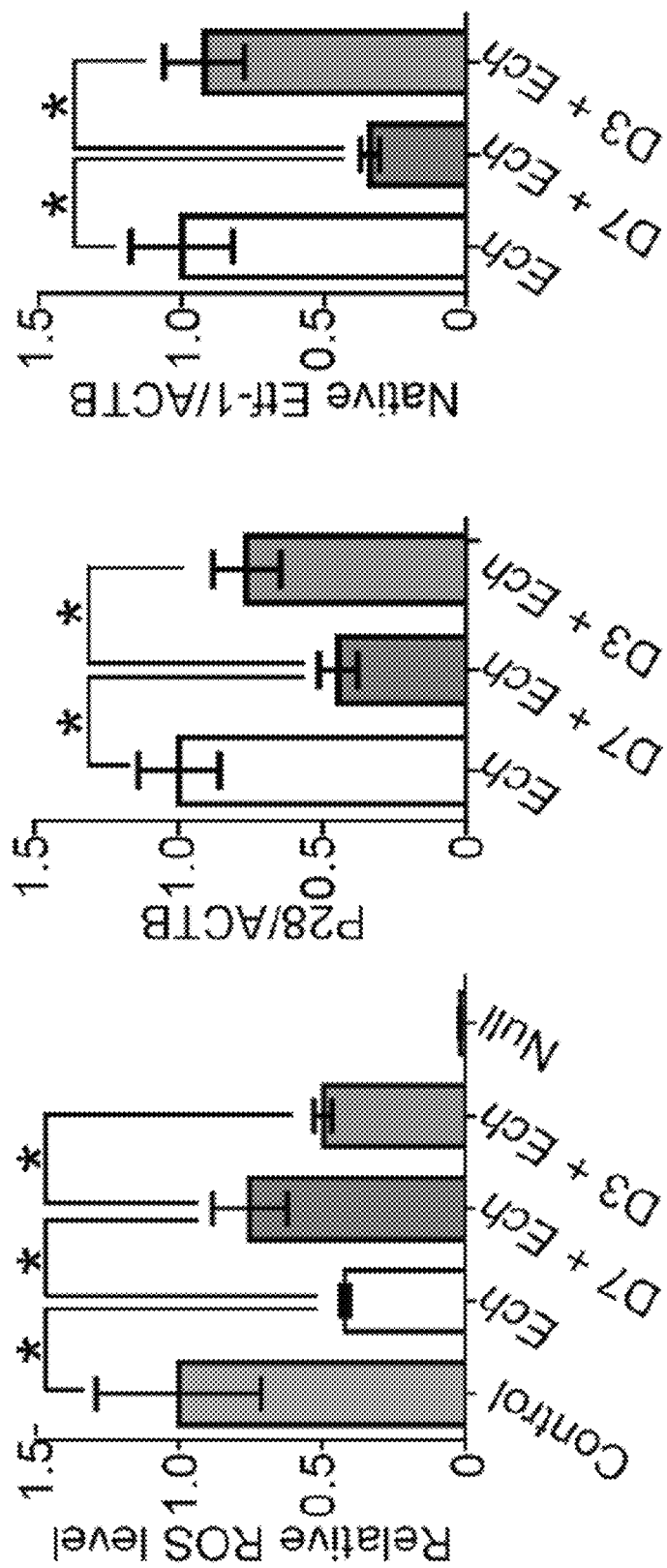

D7 abrogates *E. chaffeensis*-induced increase in MnSOD and reduction in ROS and inhibits infection. The MnSOD protein level is greater and ROS levels are lower in *E. chaffeensis*-infected cells than are those in uninfected cells. Ectopically expressed D7, but not D3, abrogated the increase in MnSOD in *E. chaffeensis*-infected cells (FIGS. 8A and 8B) and abrogated the reduction in intracellular ROS levels in *E. chaffeensis*-infected cells (FIG. 8C). Most importantly, D7 (but not D3) also inhibited *E. chaffeensis* infection of host cells based on the expression of *E. chaffeensis* P28/OMP-1F (major outer membrane proteins) as determined by western blot analysis (FIGS. 8A and 8D). Etf-1 protein itself was decreased (FIG. 8E), most likely as a result of the inhibition of *E. chaffeensis* infection.

Figure 9D:
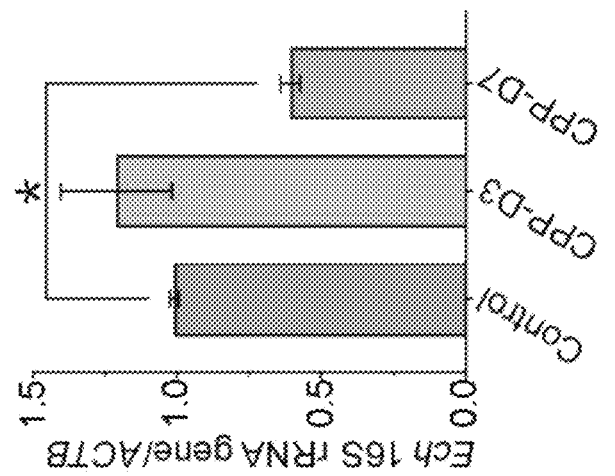
FIGS. 9A to 9D show intracellular delivery of CPP-D7 abrogates Etf-1 inhibition of host cell apoptosis and inhibits E. chaffeensis infection.
Figure 9C:
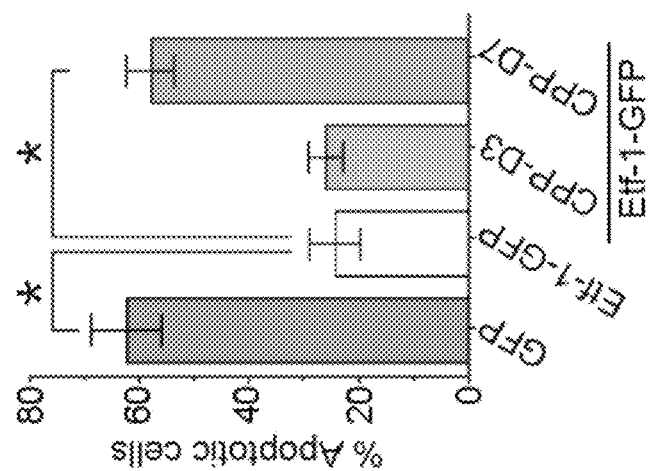
Figure 9A:
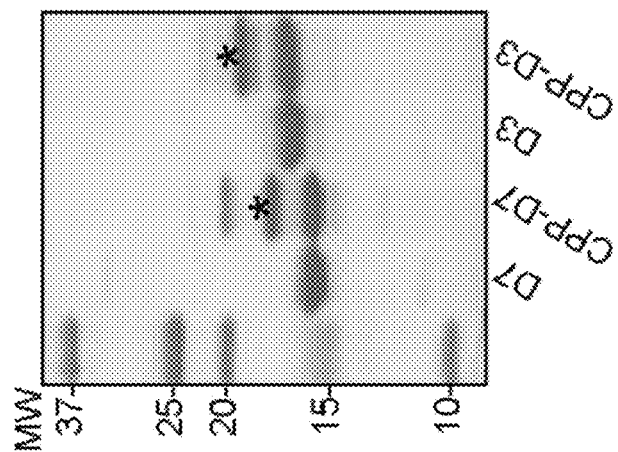
Figure 9B:
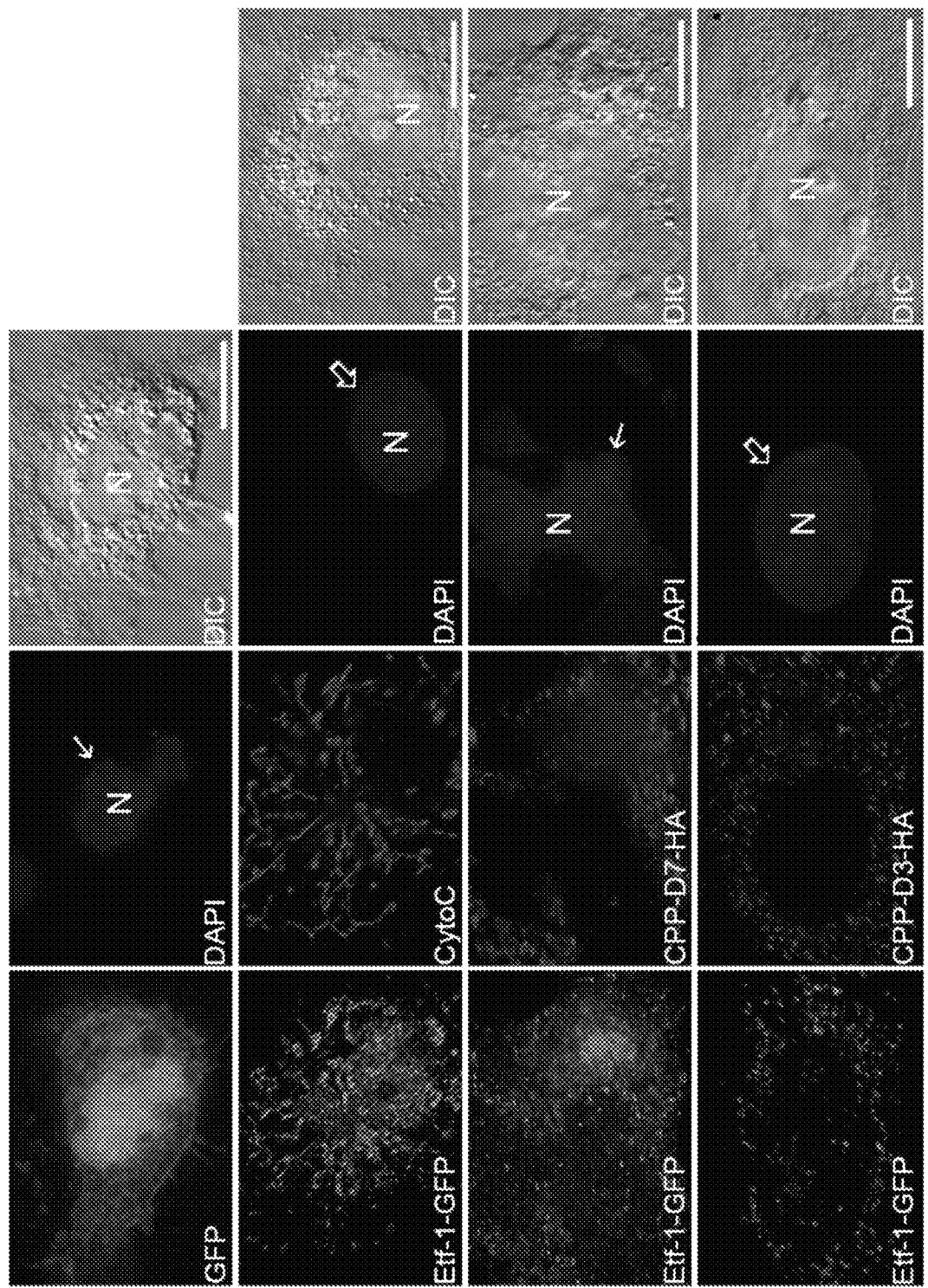
Figure 15A:
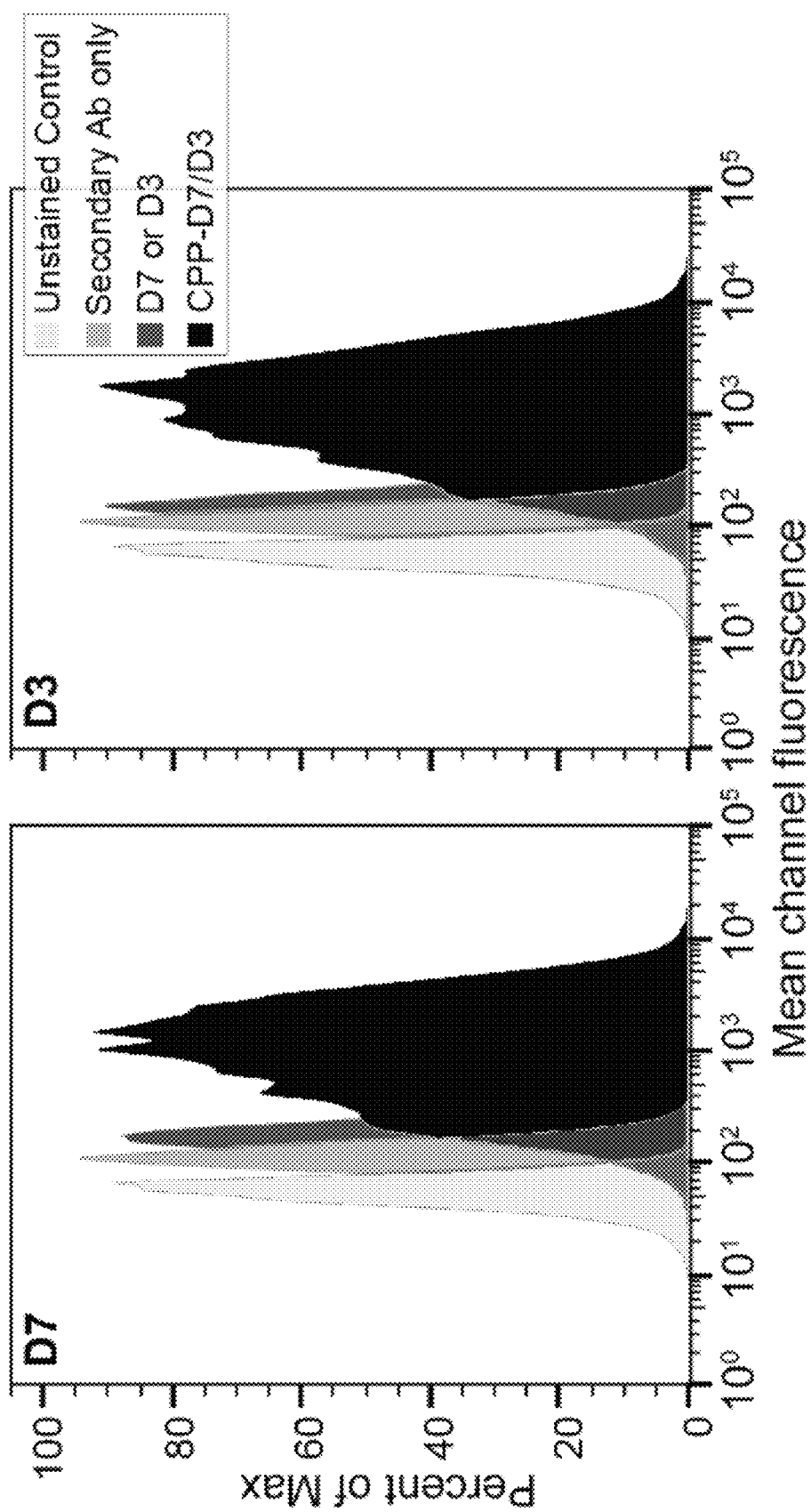
FIGS. 15A and 15B show CPP-Nbs have high intracellular uptake efficiency without any cytotoxicity.
Figure 15B:
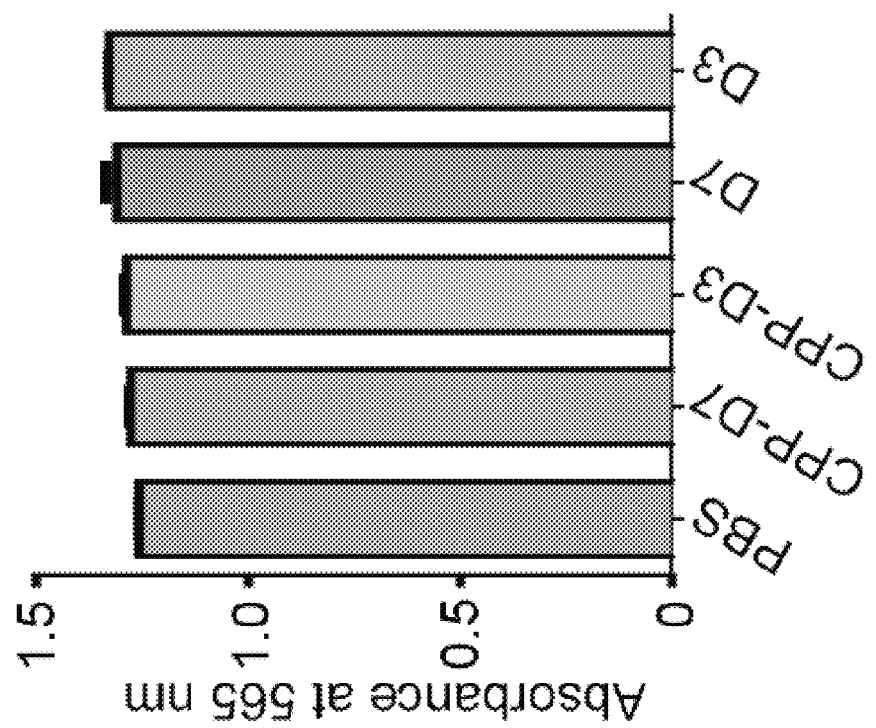

Intracellular delivery of CPP-D7 abrogates Etf-1 inhibition of host cell apoptosis and inhibits *E. chaffeensis* infection. Whereas transfection with plasmids encoding Nb is useful for in vitro analyses, in vivo application of Nb requires a different intracellular Nb delivery method the cyclic CPP12—cyclo(FfϕRrRrQ), where ϕ is L-2-naphthylalanine, f is D-phenylalanine, and r is D-arginine (SEQ ID NO:34), was therefore used for D7 and D3 conjugation. D7 and D3 were purified to >95% purity for CPP conjugation (FIG. 9A). D7 and D3 were specifically labeled with CPP at their N-terminal amine with ~40% labeling efficiency (FIG. 9A). The CPP-Nbs were effectively taken up by almost 100% of RF/6A cells based on flow cytometry (FIG. 15A). There was no cytotoxicity of CPP-Nb-treated cells as determined by the MTT (3-(4,5-dimethylthiazol-2-yl)-2,5 diphenyitetrazolium bromide) assay (FIG. 15B). CPP-D7 abrogated apoptosis inhibition induced by Etf-1-GFP, to a level similar to that of GFP-transfected control cells (FIGS. 9B and 9C), but CPP-D3 did not. When *E. chaffeensis*-infected THP-1 cells were treated with CPP-Nbs, bacterial infection was significantly reduced by CPP-D7 but not by CPP-D3 (FIG. 9D), similar to the effects of ectopically expressed Nbs (FIGS. 8A and D).

Figure 10:
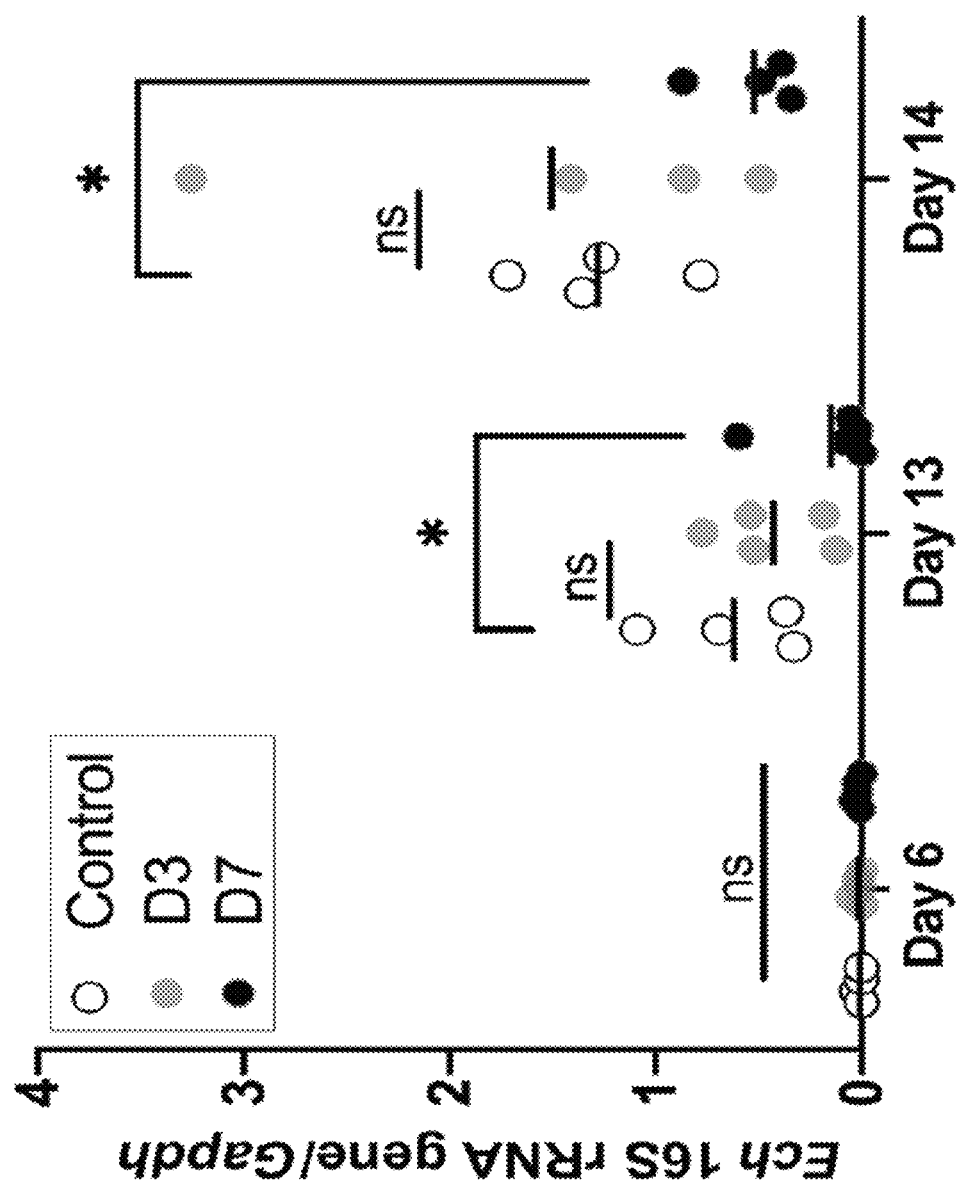
FIG. 10 shows CPP-conjugated D7, but not D3, reduces E. chaffeensis Wakulla infection in SCID mice. Three groups of five SCID mice were ip inoculated with E. chaffeensis Wakulla-infected DH82 cells that were pre-incubated with CPP-D7, CPP-D3, or PBS, respectively, for 12 h. For the following 1-2 dpi, mice were ip inoculated with CPP-D7 or CPP-D3 at 20 µg/gram body weight/d or with PBS. Infection with Ehrlichia was determined by qPCR of the blood samples collected on day 6, 13, and 14 using the E. chaffeensis (Ech) 16S rRNA gene and normalized with mouse Gapdh. The scatter plot shows the normalized Ehrlichia levels in individual mice, with the horizontal bar representing the mean value. *P<0.05, by one-way ANOVA; ns, not significant.
Figure 11A:
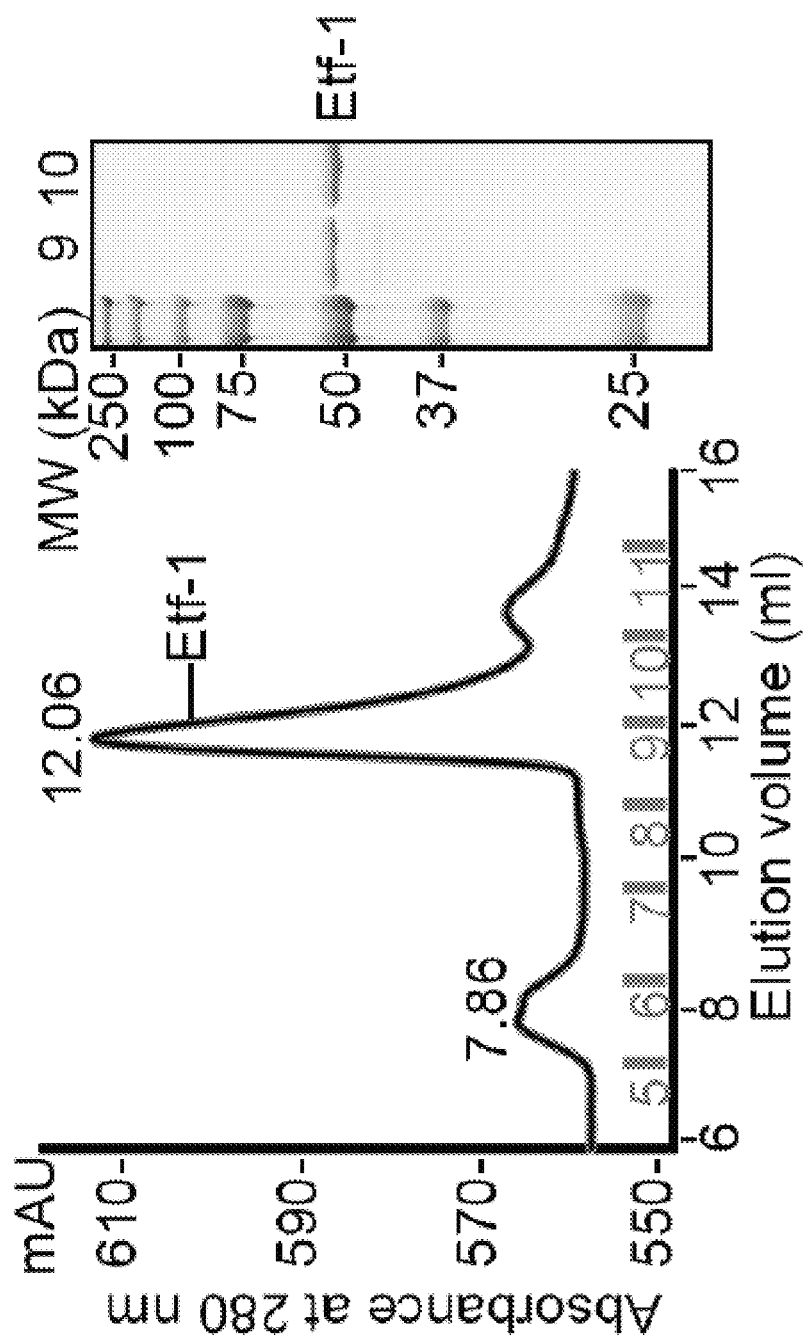
FIGS. 11A to 11C show llama immunization with rEtf-1.
Figure 11B:
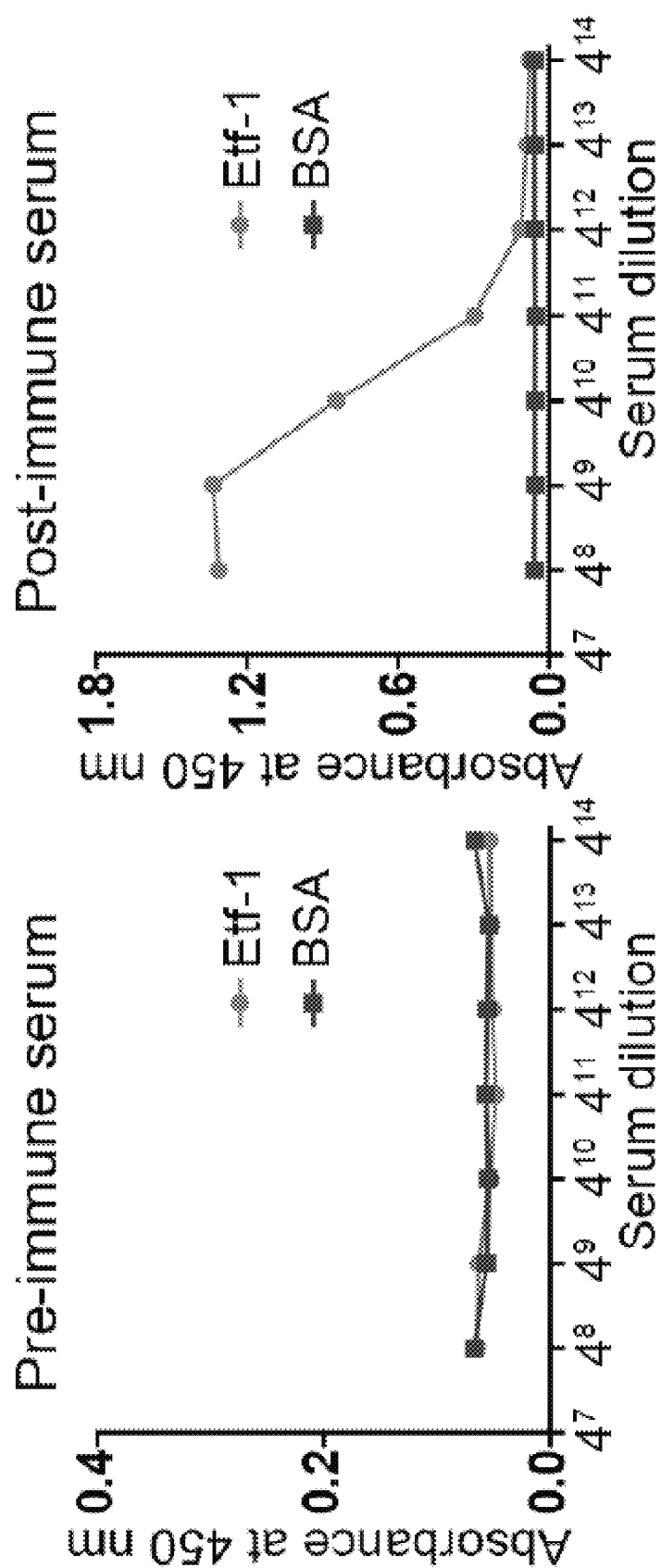
Figure 11C:
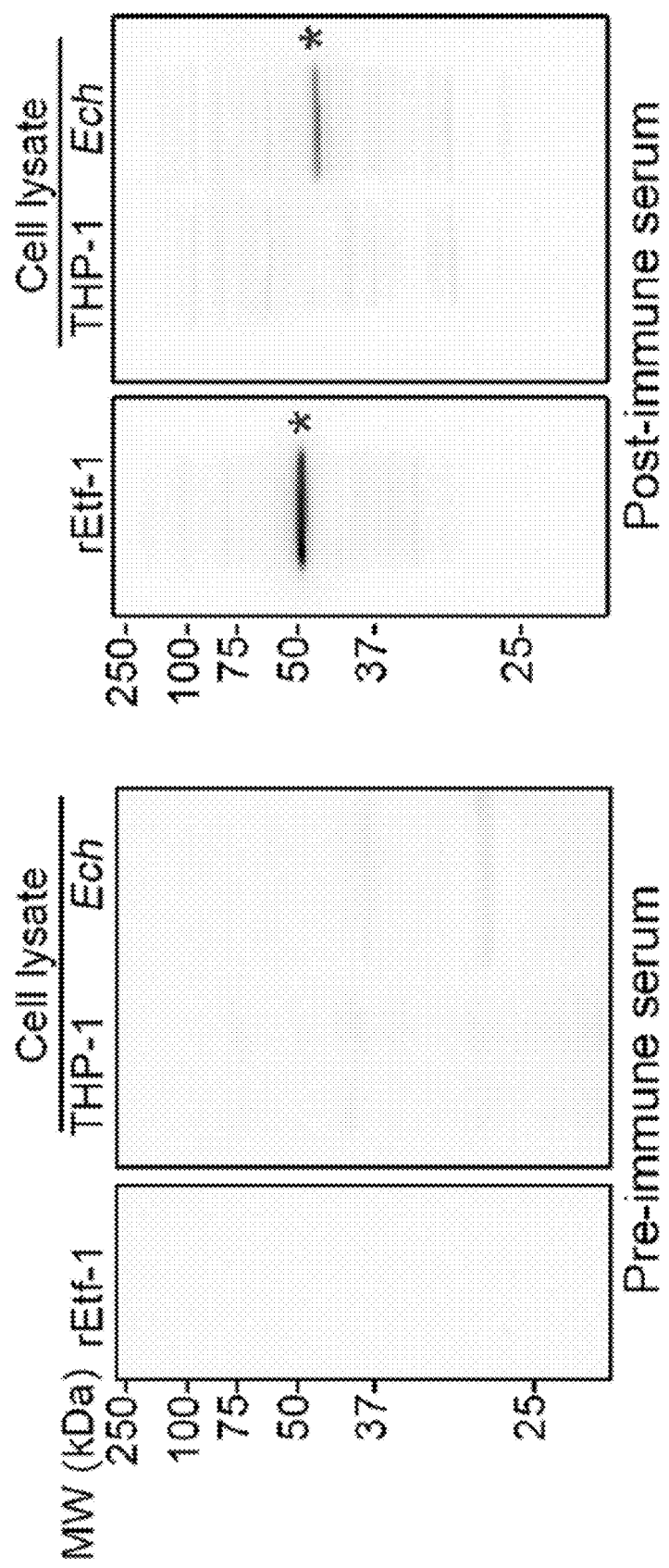
Figures 12A, 12B:
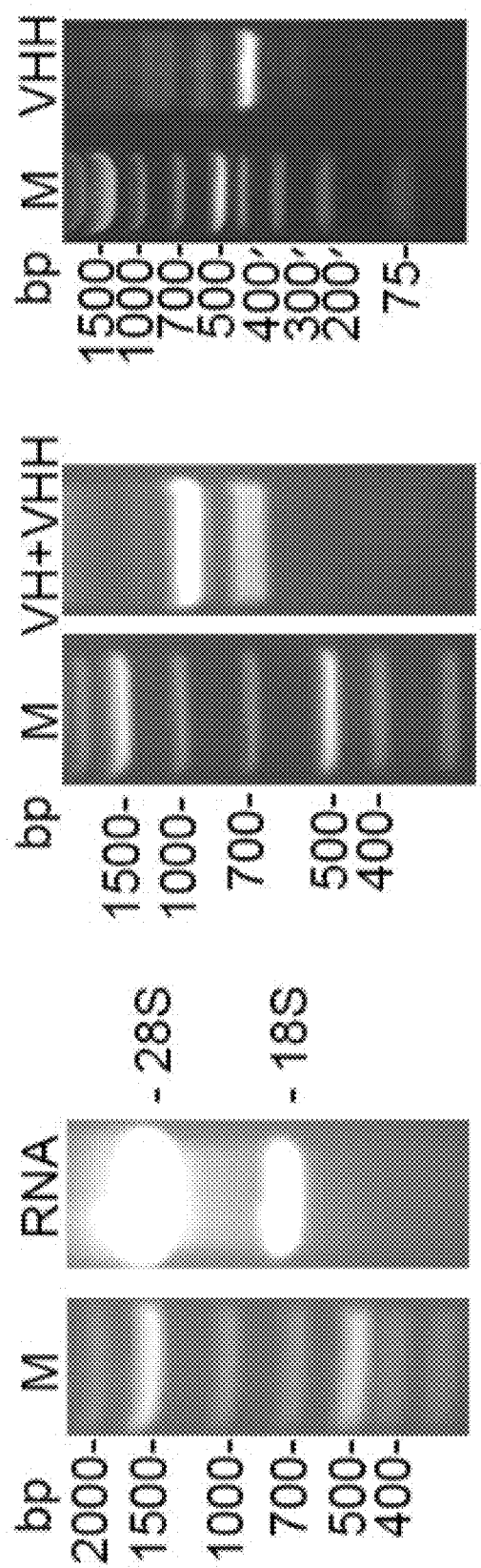
FIGS. 12A to 12D show cloning of anti-Etf-1 Nbs from the llama immune library.
Figure 12C:
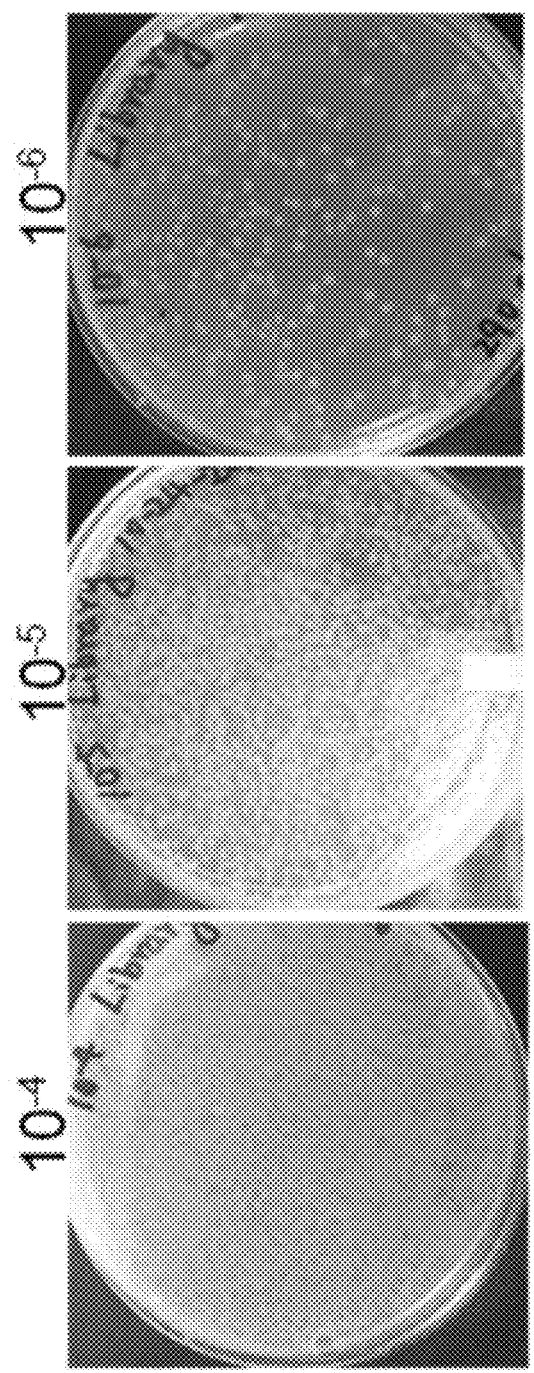
Figure 12D:
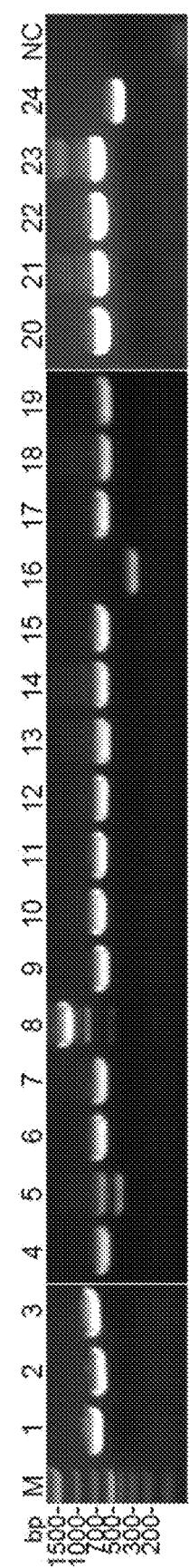

CPP-D7 reduces *E. chaffeensis* infection in severe-combined immunodeficiency (SCID) mice. Immunocompetent mice clear *E. chaffeensis* Arkansas infection within 2 weeks and do not develop clinical signs. Consequently, SCID mice have been used to investigate *E. chaffeensis* infection and pathogenesis. When SCID mice are inoculated with one of three distinct *E. chaffeensis* strains, the order of the severity of clinical signs and the bacterial burden detected in the mice is Wakulla>Liberty>Arkansas, and the Wakulla strain rapidly multiplies in the blood >2,000 fold from day 5-15 and kills mice in <15 days (39). Etf-1 amino acid sequences are identical between the *E. chaffeensis* Arkansas and Wakulla strains. Thus, analyzing the Wakulla strain in a SCID mouse infection model allowed for investigation of the effects of CPP-D7 on *Ehrlichia* infection and pathogenesis in the absence of adapted immune responses. Mice were intraperitoneally (ip) inoculated with *E. chaffeensis* Wakulla-infected DH82 cells preincubated with CPP-D7, CPP-D3, or the phosphate-buffered saline (PBS) for 12 h, and mice were ip inoculated with CPP-D7, CPP-NbD3, or PBS once per day on 1 and 2 day post-infection (dpi). Whereas there was no significand difference in *E. chaffeensis* in the blood at 6 dpi among three groups of mice, subsequent bacterial proliferation at 13 and 14 dpi was significantly inhibited in CPP-D7-inoculated SCID mice as compared with mice inoculated with CPP-D3 or PBS (FIG. 10). The result indicates inhibitory effects of CPP-D7 on virulent Wakulla strain in culture and subsequent ip inoculation of mice was sustained almost two weeks. These results further support in vitro results presented in FIG. 9, that concludes CPP-mediated intracellular Nb delivery is effective in inhibiting *E. chaffeensis* infection.

Discussion

In the present study, anti-Etf-1 Nbs were developed and it was shown that Nbs can be delivered intracellularly and that a particular Nb, D7, blocks mitochondrial localization of Etf-1. The mechanism by which intracellular D7 blocks Etf-1 localization to mitochondria is currently unknown. Although the critical mitochondrial localization signal in the N terminus of Etf-1 was determined, this was not the D7 binding site. Gel filtration chromatography revealed the stability of the Etf-1-D7 complex in solution, suggesting that D7 binding caused steric hindrance and/or misfolding of Etf-1 to prevent Etf-1 from being targeted to mitochondria. Although D3 binds Etf-1 with a similar affinity based on OpenSPR, the greatly reduced stability of the Etf-1-D3 complex in solution may not have been able to prevent Etf-1 from being targeted to mitochondria. Furthermore, Etf-1(25-380) truncation and Etf-1(21-380/K23A) mutant of Etf-1 completely abolished mitochondrial localization, and failed to inhibit etoposide-induced apoptosis, indicating that the mitochondrial localization of Etf-1 is essential for its inhibition of mitochondria-mediated apoptosis. Future analysis of the structure of the Etf-1-D7 complex would facilitate refining the D7 structure for stronger affinity and inhibition by mutating the binding site amino acids.

Etf-1 is critical for *E. chaffeensis* infection, because knockdown of Etf-1 by Etf-1 antisense peptide nucleic acid transfection of *E. chaffeensis* inhibits its ability to infect cells, and this inhibition is trans-complemented by intracellular expression of Etf-1. Ectopically expressed Etf-1 in mammalian cells inhibits cellular apoptosis, which allows sufficient time for *E. chaffeensis* to replicate. However, it is unclear whether mitochondrial localization of Etf-1 is required for this inhibition. By using NbD7, the present study demonstrated that mitochondrial localization of Etf-1 is indeed required for host cell apoptosis inhibition and effective *E. chaffeensis* infection. Both *E. chaffeensis* infection and Etf-1 ectopic expression upregulate mitochondrial MnSOD at the protein level and reduce intracellular ROS derived from mitochondrial and *E. chaffeensis* metabolism, which likely benefits *E. chaffeensis* intracellular survival as well as the survival of the infected host cell. Based on results with D7, this ROS inhibition requires mitochondrial localization of Etf-1. Molecular mechanisms of upregulation of MnSOD by Etf-1 localized in the mitochondria remain to be studied. Nonetheless, intracellularly delivered Nbs are an effective research tool for dissecting complex mechanisms of the pathogen-host interaction that occur inside host cells.

Intracellular antibodies could be developed that block bacterial virulence factors/mechanisms, host cell receptors/partners, and/or signaling pathways. Indeed, intracellular delivery of conventional antibodies against Etf-1 by the Chariot protein transfection system, or transfection of Nbs against human heterogeneous nuclear ribonucleoprotein K (hnRNP-K) can block *E. chaffeensis* infection of human cells. However, one of the critical steps for therapeutic application of intracellular Nbs is effective and safe in vivo delivery of Nbs. To overcome this universal difficulty, a new approach was used that relies on CPP, which was never tried for Nbs. Furthermore, a newer synthetic cyclic CPP was used, CPP12, which is over six times more effective than the prototype cyclic CPP cFϕPR4. By covalently linking individual Nb molecules with CPP12, the effective penetration of CPP12-Nb into almost 100% of cells by simple co-incubation for 12 h at 37° C. was demonstrated, without any cytotoxic effects. Inhibition of apoptosis and *E. chaffeensis* infection were more effective with CPP delivery of the Nb than with transfection, indicating the feasibility of this mode of intracellular Nb delivery. Indeed, CPP-D7 showed significant protection of SCID mice from the highly virulent strain Wakulla without the help of the adaptive immune system, supporting the potential therapeutic potential of CPP-Nbs for intracellular infections and other cellular ailments.

Another important function of Etf-1 is to induce Rab5-regulated autophagy and recruit Etf-1-positive early autophagosomes (amphisomes) to *Ehrlichia*-replicating inclusions, which provides the necessary nutrients for intracellular growth of *E. chaffeensis*.

Etf-1 homologs are found in every sequenced member of the genera *Ehrlichia* and *Anaplasma*, all of which are human and/or animal pathogens (Table 4). In fact, *Anaplasma* translocated substrate 1 (Ats-1) is an *A. phagocytophilum* T4SS substrate that targets host cell (neutrophil) mitochondria in an N-terminal sequence-dependent manner and prevents apoptosis in *A. phagocytophilum*-infected human neutrophils. Ats-1 also induces host cell autophagy to deliver host cytosolic catabolites to *Anaplasma*-containing inclusions for bacterial growth. Ats-1 and Etf-1 have 21% identity at the amino acid level. Thus, this approach of developing T4SS-blocking Nbs is likely to be applicable to broader members of the *Ehrlichia* and *Anaplasma* genera. Taken together, these findings support the feasibility of therapeutic use of intracellular Nbs for blocking intracellular infection.

TABLE 4

Etf-1 homologs in members of the genera *Ehrlichia* and *Anaplasma*

| Species | NCBI accession number | Similarity (% aa) | E-Value |
|---|---|---|---|
| *Ehrlichia chaffeensis*[1] | WP_011452831.1, | 100 | |
| *E. muris* subsp. *muris* AS145 | WP_024071892.1 | 79 | $1E^{-166}$ |
| *E. muris* subsp. *eauclairensis* Wisconsin | WP_045804476.1 | 76 | $1E^{-130}$ |
| *Ehrlichia sp.* HF | WP_044195177.1 | 77 | $2E^{-155}$ |
| *E. minasensis* UFMG-EV | WP_045170612.1 | 75 | $1E^{-159}$ |
| *E. canis* Jake | WP_102574816.1 | 74 | $7E^{-157}$ |
| *E. ruminantium* Welgevonden | WP_065433648.1 | 63 | $4E^{-100}$ |
| *Anaplasma phagocytophilum*[2] | ABD43383.2 | 100 | |
| *A. platys* Mili1 | WP_169193309.1 | 52 | $1E^{-56}$ |
| *A. centrale* Israel | WP_012880860.1 | 57 | $4E^{-36}$ |
| *A. ovis* Halbei | WP_075138831.1 | 55 | $1E^{-31}$ |
| *A. marginale* Florida | WP_010269731.1 | 56 | $3E^{-31}$ |

[1]*E. chaffeensis* Arkansas Etf-1 protein (WP_011452831.1, 380 aa) was used to perform a BLASTP search against the NCBI RefSeq protein database among representative *Ehrlichia* species.
[2]*Anaplasma phagocytophilum* encodes Ats-1 protein (ABD43383.2, 376 aa), which is 41% similar to *E. chaffeensis* Arkansas Etf-1 protein (E-value: $6E^{-13}$) and was used to perform a BLASTP search against the NCBI RefSeq protein database among representative *Anaplasma* species.

Materials and Methods

Ethics Statement. All animal experiments were performed in accordance with the Ohio State University Institutional Animal Care and Use Committee guidelines and approved e-protocol. The university program has full continued accreditation by the Association for Assessment and Accreditation of Laboratory Animal Care International under 000028, dated 9 Jun. 2000, and has Public Health Services assurance renewal A3261-01, dated 6 Feb. 2019 through 28 Feb. 2023. The program is licensed by the USDA, number 31-R-014, and is in full compliance with Animal Welfare Regulations.

Antibodies. Antibodies used were affinity-purified rabbit IgG against the C-terminal 250 aa of Etf-1 (residues 152-264); rabbit anti-*E. chaffeensis* recombinant major outer membrane proteins P28; mouse monoclonal anti-HA (BioLegend, San Diego, Calif.); mouse monoclonal anti-GFP, anti-MnSOD, and anti-cytochrome c (Santa Cruz Biotechnology, Dallas, Tex.); rabbit monoclonal anti-HA (Cell Signaling Technology, Danvers, Mass.); rabbit anti-actin (Sigma-Aldrich, Saint Louis, Mo.); Alexa Fluor (AF) 488- and AF555-conjugated goat anti-rabbit IgG and anti-mouse IgG (Life Technologies, Eugene, Oreg.); horseradish peroxidase (HRP)-conjugated goat anti-llama IgG (Bethyl Laboratories, Montgomery, Tex.); and HRP-conjugated goat anti-mouse IgG and HRP-conjugated goat anti-rabbit IgG (KPL, Gaithersburg, Md.).

Plasmid construction. For screening of anti-Etf-1 Nbs and OpenSPR analysis, full-length Etf-1 with an N-terminal 6× His-tag followed by a TEV protease cleavage site and C-terminal Avi-tag was ligated into pET33b(+) vector to create His-TEV-Etf-1-Avi fusion protein. For far-western blotting, truncated Etf-1 plasmids were constructed based on His-TEV-Etf-1-Avi. For mitochondrial localization analysis, truncated and/or mutated Etf-1-GFP was constructed from codon-optimized full-length Etf-1-GFP. For Nbs expression in mammalian cells, each full-length Nb was cloned into pEGFP-C1 vector by replacing EGFP with a C-terminal HA-tag. The primers used for cloning are listed in Table 5.

TABLE 5

Primer sequences for cloning truncated and mutated Etf-1 and Nbs[1]

| Residues | Primer sequence (5'-3') |
|---|---|

Cloning truncations of Etf-1 into pET33b(+) for expression in *E. coli* BL21(DE3)

| | |
|---|---|
| 1-380 | F: GGAATTC<u>CATATG</u>GAAAACCTGTATTTTCAGGGCATGCTTACTTTCTTAAAG (SEQ ID NO: 87)<br>R: CGC<u>GGATCC</u>TTATTCATGCCATTCAATTTTCTGCGCTTCAAAAATATCGTTCAGGCCTCTTGCATGTAC (SEQ ID NO: 88) |
| 26-380 | F: GGAATTC<u>CATATG</u>GAAAACCTGTATTTTCAGGGCCATCAAGAAAGCGTAGGT (SEQ ID NO: 89)<br>R: CGC<u>GGATCC</u>TTATTCATGCCATTCAATTTTCTGCGCTTCAAAAATATCGTTCA GGCCTCTTGCATGTAC (SEQ ID NO: 90) |
| 51-380 | F: GGAATTC<u>CATATG</u>GAAAACCTGTATTTTCAGGGCAAACACTTTGACTTAAGA (SEQ ID NO: 91)<br>R: CGC<u>GGATCC</u>TTATTCATGCCATTCAATTTTCTGCGCTTCAAAAATATCGTTCAGGCCTCTTGCATGTAC (SEQ ID NO: 92) |
| 80-380 | F: GGAATTC<u>CATATG</u>GAAAACCTGTATTTTCAGGGCGAAGTAGCTCTGAAAGTA (SEQ ID NO: 93)<br>R: CGC<u>GGATCC</u>TTATTCATGCCATTCAATTTTCTGCGCTTCAAAAATATCGTTCAGGCCTCTTGCATGTAC (SEQ ID NO: 94) |

TABLE 5-continued

Primer sequences for cloning truncated and mutated Etf-1 and Nbs[1]

| Residues | Primer sequence (5'-3') |
|---|---|
| 113-380 | F: GGAATTC<u>CATATG</u>GAAAACCTGTATTTTCAGGGCACTAAAAAAGATACCTTA (SEQ ID NO: 95)<br>R: CGC<u>GGATCC</u>TTATTCATGCCATTCAATTTTCTGCGCTTCAAAAATATCGTTCAGGCCTCTTGCATGTAC (SEQ ID NO: 96) |

Cloning truncations and point-mutations of codon-optimized Etf-1 into pEGFP-N1 for expression in mammalian cells

| Residues | Primer sequence (5'-3') |
|---|---|
| 1-380 | F: AGT<u>GCTAGC</u>CGCCACCATGGTGCTGACCTTCCTGAAG (SEQ ID NO: 97)<br>R: CAA<u>GAATTC</u>GTCTGGCATGCACCTTTCC (SEQ ID NO: 98) |
| 1-306 | F: AGT<u>GCTAGC</u>CGCCACCATGGTGCTGACCTTCCTGA (SEQ ID NO: 99)<br>R: CAA<u>GAATTC</u>GGGTCCGAGAATAAGGCATA (SEQ ID NO: 100) |
| ΔCoil1[2] | Etf-1-Opt-F: AGT<u>GCTAGC</u>CGCCACCATGGTGCTGACCTTCCTGAAG (SEQ ID NO: 101)<br>ΔCoil1-R: CCGGGAGTGCTGTTCACTGTGAACTCCTGGGTGGCTGACA (SEQ ID NO: 102);<br>ΔCoil1-F: TGTCAGCCACCCAGGAGTTCACAGTGAACAGCACTCCCGG (SEQ ID NO: 103)<br>Etf-1-Opt-R: CAA<u>GAATTC</u>GTCTGGCATGCACCTTTCC (SEQ ID NO: 104) |
| 1-380 (K6, 7A) | F: AGT<u>GCTAGC</u>CGCCACCATGGTGCTGACCTTCCTG*GCCGCT*GGCGCCAACG (SEQ ID NO: 105)<br>R: CAA<u>GAATTC</u>GTCTGGCATGCACCTTTCC (SEQ ID NO: 106) |
| 21-380 | F: AGT<u>GCTAGC</u>CGCCACCATGGTGACCACAAGCAAGCTGCCTC (SEQ ID NO: 107)<br>R: CAA<u>GAATTC</u>GTCTGGCATGCACCTTTCC (SEQ ID NO: 108) |
| 21-380 (K23A) | F: AGT<u>GCTAGC</u>CGCCACCATGGTGACCACAAGC*GC*TCTGCCTC (SEQ ID NO: 109)<br>R: CAA<u>GAATTC</u>GTCTGGCATGCACCTTTCC (SEQ ID NO: 110) |
| 23-380 | F: AGT<u>GCTAGC</u>CGCCACCATGGTGAAGCTGCCTCACCAGGAGTC (SEQ ID NO: 111)<br>R: CAA<u>GAATTC</u>GTCTGGCATGCACCTTTCC (SEQ ID NO: 112) |
| 25-380 | F: AGTGCTAGCCGCCACCATGGTGCCTCACCAGGAGTCCGTG (SEQ ID NO: 113)<br>R: CAA<u>GAATTC</u>GTCTGGCATGCACCTTTCC (SEQ ID NO: 114) |

Cloning anti-Etf-1 Nbs into pEG-FP-C1 for expression in mammalian cells

| Residues | Primer sequence (5'-3') |
|---|---|
| Full length | F: CTAGCTAGCGCTACCGGTCGCCACCATGGCCCAGGTGCAGCTGCAG (SEQ ID NO: 115)<br>R: CCG<u>GAATTC</u>TTATCAGGAACCGTAGTCCGGAAC (SEQ ID NO: 116) |

[1]F, forward primer; R, reverse primer; underlined, restriction enzyme sites; bold, Kozak sequences for mammalian cell expression; bold and italicized, point mutations.
[2]The first-step PCR amplification used primer pairs Etf-1-Opt-F/ΔCoil-1R and ΔCoil-1F/Etf-1-Opt-R, and both first-step PCR products were combined and further amplified by the second-step PCR using primer pairs Etf-1-Opt-F and Etf-1-Opt-R.

Recombinant protein expression, purification, and biotinylation. Avi-tagged full-length recombinant Etf-1 protein (rEtf-1) and truncated rEtf-1 proteins (primers shown in Table 5) were expressed in *E. coli* BL21(DE3) (New England Biolabs, Ipswich, Mass.) and purified by affinity chromatography using HisPur Cobalt resin (Thermo Scientific, Rockford, Ill.) as described. The proteins were further purified by size exclusion chromatography on an AKTA express (GE Healthcare, Piscataway, N.J.) with a Superdex 200 Increase 10/300 GL column (GE Healthcare). For biotinylation, rEtf-1 was separated in Tris buffer (10 mM Tris, pH 8.0; 10 mM NaCl; 0.05% CHAPS; 0.05% sodium deoxycholate [NaDoc]) and concentrated to 2.2 mg/ml and was then biotinylated at the C-terminal Avi-tag using BirA Biotin-Protein Ligase Kit (Avidity, Aurora, Colo.). The reaction mixture was subjected to size exclusion chromatography with a Superdex 200 Increase 10/300 GL column to remove BirA and D-biotin and then underwent a buffer exchange to PBS (8 mM $Na_2HPO_4$, 1.47 mM $KH_2PO_4$, 2.67 mM KCl, 137.9 mM NaCl, pH 7.4) containing 0.05% CHAPS and 0.05% NaDoc. The biotinylation of rEtf-1 was verified by western blotting, and the labeled protein was then used for ELISA, panning, and OpenSPR analyses.

Llama immunization and analysis of serum conversion. For llama immunization, full-length Etf-1 with an N-terminal 6× His-tag was purified by affinity chromatography using HisPur Cobalt resin followed by size exclusion chromatography on an AKTA express with a Superdex 200 Increase 10/300 GL column in HEPES buffer (20 mM HEPES, pH 7.2; 150 mM NaCl). Freshly prepared Etf-1 protein (1 mg Etf-1 in 2 ml buffer) was mixed gently with 2 ml of GERBU adjuvant (GERBU Biotechnik, San Diego, Calif.) to form an emulsion, and then polymyxin B (Sigma-Aldrich) was added to a final concentration of 20 μg/ml. A 3-year-old castrated male llama was injected subcutaneously with the emulsion at two bilaterally symmetrical sites at the base of the neck near the lymph node; this was repeated two additional times with 2-week intervals between injections. Prior to the first immunization, 20 ml of blood was collected in a Venosafe serum gel tube (BD, Franklin Lakes, N.J.) and clotted for 2 h at room temperature (RT); the supernatant was then recovered after centrifugation (pre-immune serum). This process was repeated at 3 d after the third immunization (post-immune serum).

An ELISA was performed as described. Briefly, a MaxiSorp 96-well plate (Thermo Fisher Scientific) was coated with 4 μg/ml of NeutrAvidin (Thermo Fisher Scientific) followed by 3 μg/ml of biotinylated rEtf-1 in PBST (PBS containing 0.05% Tween 20). BSA was biotin-labeled with EZ-Link Sulfo-NHS-Biotin kit (Thermo Fisher Scientific) and used as a negative control. The wells were first blocked with 5% skim milk (Difco, Franklin Lakes, N.J.) in PBST and then were incubated with four-fold serially diluted serum samples starting from a 1:64 dilution in PBST containing 0.1% skim milk for 1 h and then with 1:10,000 HRP-conjugated goat anti-llama IgG. The absorbance was measured by a SpectraMax PLUS384 spectrophotometer (Molecular Devices, Sunnyvale, Calif.) following the addition of $H_2O_2$ and TMB substrate (Thermo Fisher Scientific). To verify antibody recognition of rEtf-1 and native *E. chaffeensis* Etf-1, western blotting analyses were performed.

Nb library construction and isolation of Etf-1-binding Nbs. The Nb library was constructed. Briefly, 5 d after the third immunization, 400 ml of blood was collected from the jugular vein in a Venosafe hematology citrate phosphate dextrose-coated blood collection bag (Fenwal, Lake Zurich, Ill.), and lymphocytes were separated immediately using Ficoll-Paque Plus (GE Healthcare). Total RNA was extracted using RNeasy Plus Mini kit (QIAGEN, Valencia, Calif.), and the first-strand cDNA was synthesized from 50 μg of total RNA using SuperScript III Reverse Transcriptase (Invitrogen, Carlsbad, Calif.). The variable domains of all immunoglobulin heavy chains were PCR amplified using two gene-specific primers, CALL001 and CALL002, with KOD Hot Start DNA Polymerase (TOYOBO, New York, N.Y.). The 700-bp PCR products were gel purified and further PCR amplified using Nb-For and Nb-Back primers with Eco91I and PstI sites. The final 400-bp PCR products encoding Nb sequences were ligated into pMECS phagemid vector following digestion with PstI/Eco91I restriction enzymes (with the addition of XbaI restriction enzyme to reduce vector self-ligation) and transformed into the *E. coli* TG1 strain (Lucigen, Middleton, Wis.) using a Gene Pulser Xcell electroporation system (Bio-Rad, Hercules, Calif.). Colonies were titrated and analyzed by colony PCR using MP57 and GIII primers to determine the total and functional library sizes.

Nbs were expressed on the surface of rescued recombinant VCSM13 phages after the TG1 cells of the immune library were infected with VCSM13 helper phage (Agilent, Santa Clara, Calif.). Phages with specificity for Etf-1 were enriched by one round of panning: Phages ($10^{11}$ phages/well) were added to either denatured (by boiling for 10 min) or non-denatured biotinylated rEtf-1 that had been coated on microtiter plates (405 ng/well) and bound phages were eluted with trypsin (Thermo Fisher Scientific). The eluate was transferred to separate microcentrifuge tubes prefilled with 5 μl of a 4 mg/ml AEBSF (Thermo Fisher Scientific) solution to inhibit protease activity and was used to infect freshly cultured exponentially growing TG1 cells. The enrichment of phage particles carrying the Etf-1-specific Nbs was calculated by comparing the number of phages eluted from rEtf-1-coated wells vs. negative control wells. After panning, 368 individual clones eluted either from denatured rEtf-1 or non-denatured rEtf-1 were screened by standard ELISA procedures using mouse anti-HA at a 1:1,000 dilution and HRP-conjugated goat anti-mouse IgG at a 1:7,500 dilution.

Plasmids of the positive clones were purified from TG1 cells, transformed into DH5α cells, and sequenced. The CDR3 amino acid sequences of 107 and 65 Nbs bound to non-denatured and denatured rEtf-1, respectively, were aligned using the MegAlign program with the ClustalW algorithm of Lasergene DNASTAR software (DNASTAR, Madison, Wis.). A phylogenetic tree based on the alignment of 24 distinct CDR3 amino acid sequences was obtained using the MegAlign program.

Expression and purification of anti-Etf-1 Nbs. Plasmids encoding anti-Etf-1 Nbs were purified from TG1 cells and transformed into WK6 cells, a non-suppressor strain (supE⁻) of *E. coli* (ATCC). Nbs, which contain the periplasmic localization sequence pelB signal peptide at their N terminus, were expressed and purified from the periplasm. The supernatant containing the Nbs, which contain a C-terminal HA-tag followed by a 6× His-tag, was affinity purified with the cobalt resin followed by size exclusion chromatography on an AKTA express using a Superdex 75 Increase 10/300 GL column (GE Healthcare) for OpenSPR and far-western blot analysis.

Characterization of D7 and D3 binding to rEtf-1 by FPLC and OpenSPR. Binding of D7 and D3 with rEtf-1 was qualitatively assessed by mixing the purified rEtf-1 with excess D7 or D3 proteins, separating the mixture with a Superdex 200 Increase 10/300 GL gel filtration column in PBS running buffer (PBS containing 0.05% CHAPS and 0.05% NaDoc), and analyzing each fraction for the presence rEtf-1 and D7 or D3 by Western blotting. The affinity binding constant was measured by OpenSPR (Nicoya, Kitchener, ON, Canada). After immobilization of biotinylated rEtf-1 to a streptavidin sensor chip (Nicoya), dilutions of D7 and D3 in PBST running buffer were slowly flowed over the sensor chip at a rate of 20 μl/min with a contact time of 270 s and dissociation time of 330 s. Binding kinetics were obtained using TraceDrawer software (Nicoya).

CPP conjugation of D7 and D3. CPP12 was synthesized and purified by high-performance liquid chromatography (HPLC). FPLC-purified D7 and D3 with >95% purity in PBS at 3 mg/ml were adjusted to pH 6.2 with 1 M MES buffer (pH 5.5). Proteins were incubated with 8 molar equivalents of CPP12 for 1 h at RT on an end-to-end rotator, and then freshly prepared 10 mM NaBH₃CN solution was added to the mixture. Reactions were continued at 4° C. for 48 h and 72 h for D7 and D3, respectively. Buffer containing the CPP12 and D7 or D3 conjugates was exchanged to PBS, and excess CPP12 was removed by FPLC through a HiTrap desalting column (GE Healthcare). CPP-D7 and CPP-D3 were concentrated to 3.6 mg/ml (0.22 mM) and 3.7 mg/ml (0.24 mM), respectively, for subsequent experiments.

Analysis of mitochondrial localization of Eff-1 and apoptosis assay. For transfection of mammalian cells, plasmids were transformed into *E. coli* strain DH5a (Invitrogen) and purified using the Endo-Free Plasmid Purification kit (QIAGEN, or OMEGA, Norcross, Ga.).

To examine the cellular distribution of truncated and mutated Etf-1-GFP, plasmids were transfected into RF/6A cells using Fugene HD (Promega, Madison, Wis.). For apoptosis assays, RF/6A cells were transfected with full length, truncated, or mutated Etf-1-GFP, or co-transfected with Etf-1-GFP and D7-HA or D3-HA plasmids by electroporation at 100 V and 1000 μF using the Gene Pulser Xcell System and were then seeded onto coverslips at $1.3 \times 10^5$ cells/well in a 12-well plate. To determine the ability of CPP-Nbs to inhibit Etf-1-induced apoptosis, RF/6A cells transfected with Etf-1-GFP at 12 hpt were treated with 10 μM CPP-D7 or CPP-D3 in AMEM with 1% FBS for 12 h. At 24 hpt, cells were washed to remove uninternalized CPP-Nbs and changed to AMEM with 10% FBS. The cells were then treated with 100 μM etoposide (Sigma-Aldrich) for 4 h.

At 2 day post-transfection (dpt), cells were fixed with 4% paraformaldehyde in PBS at RT for 20 min. The cells were then labeled with primary antibodies (mouse anti-cytochrome c, rabbit anti-Etf-1, mouse anti-GFP, and/or rabbit anti-HA) diluted 1:50 in PGS (PBS with 0.1% gelatin and 0.1% saponin) for 2 h at RT, followed by AF488- or AF555-conjugated goat anti-mouse IgG and/or anti-rabbit IgG diluted 1:100 in PGS at RT for 1 h. Nuclei were stained with 300 nM 4',6-diamidino-2-phenylindole (DAPI), and coverslips were mounted and sealed with nail polish. Fluorescence images and DIC images were captured with a DeltaVision deconvolution microscope (Applied Precision, Issaquah, Wash.). Mitochondria exist as distinct filaments in RF/6A cells; therefore, when GFP-tagged Etf-1 or Etf-1 mutants showed filamentous distribution and colocalized with cytochrome c, these cells were scored as positively localized to mitochondria. When GFP-tagged Etf-1 or Etf-1 mutants were expressed in punctate or diffuse patterns, and did not colocalize with cytochrome c, these cells were scored as no colocalization with mitochondria. To determine the effects of Nbs on the localization of Etf-1 to mitochondria, only RF/6A cells expressing both Etf-1-GFP and D7- or D3-HA were selected.

Far-western blot analysis. Purified full-length rEtf-1 and various truncated rEtf-1 proteins and BSA were run on SDS-polyacrylamide gels and transferred to PVDF membranes using a semi-dry blotter (WEP, Seattle, Wash.). Proteins on the membranes were denatured with 6 M guanidine-HCl in a basic buffer (20 mM Tris, pH 7.6; 100 mM NaCl; 0.5 mM EDTA; 10% glycerol; 0.1% Tween-20; 2% skim milk; 1 mM DTT), followed by renaturing in the basic buffer containing serially diluted guanidine-HCl. The membrane was blocked with 5% skim milk in PBST at RT for 1 h and then was incubated with 5 ml of 2 µg/ml NbD7-HA-His or NbD3-HA-His overnight at 4° C. Membranes were probed with mouse anti-HA (1:2,000 dilution) followed by HRP-conjugated goat anti-mouse IgG (1:1,000 dilution). ECL western blotting substrate (Thermo Scientific) was used for chemiluminescence detection, and images were captured by an Amersham Imager 680 (GE Healthcare).

E. chaffeensis and cell culture. E. chaffeensis Arkansas strain was cultured in THP-1 cells (ATCC, Manassas, Va.) in RPMI 1640 medium (Corning, Manassas, Va.) supplemented with 8% fetal bovine serum (FBS; Atlanta Biologicals, Flowery Branch, Ga.) at 37° C. under 5% $CO_2$ in a humidified atmosphere. E. chaffeensis Wakulla strain was propagated in DH82 cells (46) in Dulbecco's Modified Eagle's Medium (DMEM, Corning) with 8% FBS as described (39, 47). RF/6A cells (ATCC) were cultured in Advanced Minimum Essential Medium (AMEM; Gibco, Grand Island, N.Y.) with 10% FBS. HEK293 cells (ATCC) were cultured in DMEM with 5% FBS. HEK293T cells (ATCC) were cultured in DMEM with 10% FBS. All culture media were supplemented with an additional 2 mM L-glutamine (Gibco).

ROS assay with H2DCFDA and western blot analysis. HEK293 cells were seeded in a 96-well flat- and clear-bottom black plate (Tecan, Morrisville, N.C.) at $1 \times 10^4$ cells/well. HEK293 cells were transfected with D7-HA or D3-HA using Fugene HD and then were infected by E. chaffeensis (~50 multiplicity of infection [MOI]) at 1 dpt or were co-transfected with plasmids encoding Etf-1-HA and D7- or D3-HA. At 2 dpi (3 dpt) or at 2 dpt for the co-transfection experiments, the amount of ROS in whole cells was detected by using the fluorescent dye $H_2DCFDA$ (Invitrogen). Briefly, cells were washed with PBS and then incubated with 200 µl of 10 µM $H_2DCFDA$ in pre-warmed PBS for 30 min at 37° C. under 5% $CO_2$. The cells were washed once with PBS, and the fluorescence intensity of DCF (corresponding to the ROS level) was measured with an Infinite 200 PRO Microplate Reader (Tecan) at excitation and emission wavelengths of 492 nm and 520 nm, respectively.

For western blot analysis, $2 \times 10^6$ HEK293 cells were transfected and infected with E. chaffeensis as described above for 2 d. Cell lysates were subjected to western blotting using primary antibodies including rabbit anti-recombinant P28 (diluted 1:2,000), rabbit anti-Etf-1 (1:2,000), mouse anti-MnSOD (1:1,000), rabbit anti-actin (1:2,000), and mouse anti-HA (1:1,000) to detect Nbs, followed by HRP-conjugated secondary antibodies (1:2,000). Images were captured by the Amersham Imager 680, and band densities were quantitated by ImageQuantTL (GE Healthcare). As the rabbit anti-recombinant P28 antisera (36) recognized both native P28 and OMP-1F expressed by E. chaffeensis (37), band densities of both proteins were used in the quantitation to determine E. chaffeensis infection levels.

Analysis of CPP12-Nbs on E. chaffeensis infection and quantitative PCR (qPCR). THP-1 cells were seeded at $2 \times 10^5$ cells/well in a 12-well plate and infected with host cell-free E. chaffeensis at 20 MOI. At 2 hpi, cells were treated with 10 µM CPP-D3/D7 or with an equal volume of PBS (control) in 1 ml RPMI 1640 medium with 1% FBS. After a 12-h incubation, cells were washed to remove uninternalized CPP-Nbs and cultured in fresh RPMI 1640 medium with 8% FBS for 2 d. DNA was extracted from each culture, and qPCR analysis was performed in an MX3000P qPCR instrument (Stratagene, San Diego, Calif.) using SYBR Green Real-Time PCR Master Mix (Thermo Fisher Scientific). Fivefold serial dilutions of the control group was used to generate a standard curve to calculate the relative copy numbers of E. chaffeensis 16S rRNA and human actin genes using the MX3000P software from Stratagene.

Infection of SCID mice with E. chaffeensis Wakulla and their treatment with CPP-conjugated Nbs. E. chaffeensis Wakulla-infected DH82 cells at ~30% infectivity were centrifuged and resuspended at $1 \times 10^5$ cells in 0.5 ml of DMEM containing 1% FBS. The cells were incubated with CPP12-conjugated Nbs (~50% conjugation efficiency, 80 µg CPP12-D3 or -D7 in 30 µl PBS) or a PBS only control at 37° C. for 12 h. Cells were then mixed with 0.47 mg of CPP-Nbs or an equal volume of PBS and injected with a 26-gauge needle into the peritoneal cavity of a 4-week-old SCID ICR mouse (obtained from Taconic, Tarrytown, N.Y.). Five mice were used for each group. At 1 and 2 dpi, each mouse was inoculated intraperitoneally with ~0.47 mg of CPP-Nb diluted in 500 µl of PBS (equivalent to 0.02 mg CPP-Nb per gram body weight with an average mouse body weight of 23 g) or with PBS alone. Mice were monitored daily for body weight and clinical signs (squinty eyes, anorexia, and inactivity) of infection with E. chaffeensis. In addition, blood samples were collected from the sublingual sinus on days 0, 6, and 13 post-infection. One mouse in each group died on 13 dpi during blood collection. All remaining mice were euthanized on 14 dpi. DNA was isolated from the blood samples using Chelex 100 Resin (Bio-Rad, Hercules, Calif.) or QIAamp DNA Blood Mini kit (Qiagen), and qPCR analysis was performed by using primers targeting the E. chaffeensis 16S rRNA gene and mouse Gapdh.

Flow cytometry. HEK293T cells were cultured in 24-well plates ($2.5 \times 10^5$ cells/well) for 24 h and incubated for 12 h with 10 µM CPP-D7, CPP-D3, D7, D3, or an equivalent volume of PBS in DMEM medium with 1% FBS. Cells were washed to remove unbound CPP-Nbs or Nbs, fixed with 4% paraformaldehyde for 10 min. Internalized HA-tagged Nbs were labeled with monoclonal rabbit anti-HA (1:1.600 dilution in PGS), followed by AF555-conjugated goat anti-rabbit IgG) 1:200 dilution in PGS) at RT for 1 h each. Cells were analyzed on an Attune NxT acoustic focusing cytometer (Life Technologies) using the YL1 channel (excitation, 561 nm; emission, 585 nm). Data were analyzed by FlowJo software (Becton Dickinson, San Jose, Calif.) to visualize differences in relative percentages of cell populations among groups.

MTT assay. RF/6A cells were cultured in 96-well plates at 5,000 cells/well for 6 h and incubated for 12 h with 10 µM CPP-D7, CPP-D3, D7, D3, or an equivalent volume of PBS in AMEM medium containing 1% FBS and 2 mM l-glutamine. Cells were washed with PBS to remove unbound CPP-Nbs or Nbs, and cultured in AMEM medium with 10% FBS and 2 mM l-glutamine for an additional 24 h. MTT (Roche, Mannheim, Germany) solution was added to each well (10 µl/well) and incubated for 4 h at 37° C. The formazan crystals were solubilized by the addition of 100 µl of solubilization buffer (Roche) to each well, and the plates were incubated overnight at 37° C. Absorbance at 565 nm was determined using a SpectraMax PLUS384 spectrophotometer (Molecular Devices).

Statistical analysis. All statistical analyses were performed with a one-way ANOVA using Prism 8 software (GraphPad, San Diego, Calif.). A post hoc test was then used to determine significant differences between different treatments. $P<0.05$ was considered to reflect a statistically significant difference.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising a nanobody, wherein the nanobody comprises CDR1, CDR2, and CDR3 sequences, wherein the CDR1 sequence of the $V_H$ domain comprises the amino acid sequence GGTLSSYT (SEQ ID NO:30), the CDR2 sequence of the $V_H$ domain comprises the amino acid sequence VARVNGRI (SEQ ID NO:31), and the CDR3 sequence of the $V_H$ domain comprises the amino acid sequence AAQEFGYTGGISRAISDYDY (SEQ ID NO:32).

2. The composition of claim 1, wherein the nanobody comprises the amino acid sequence SEQ ID NO:33.

3. The composition of claim 1, wherein the nanobody is conjugated to a cell permeabilization peptide (CPP).

4. The composition of claim 3, wherein the CPP comprises the amino acid sequence cyclo(FfφRrRrQ) (SEQ ID NO:34), where φ is L-2-naphthylalanine, f is D-phenylalanine, and r is D-arginine.

5. An isolated nucleic acid encoding the nanobody of claim 1.

6. A pharmaceutical composition comprising nanobody of claim 3 in a pharmaceutically acceptable carrier.

7. A method for treating Human monocytic ehrlichiosis (HME) in a subject, comprising administering to the subject a therapeutically effective amount of the pharmaceutical composition of claim 6.

* * * * *

```
                         SEQUENCE LISTING

<160> NUMBER OF SEQ ID NOS: 116

<210> SEQ ID NO 1
<211> LENGTH: 36
<212> TYPE: PRT
<213> ORGANISM: Artificial Sequence
<220> FEATURE:
<223> OTHER INFORMATION: Synthetic Construct

<400> SEQUENCE: 1

Asp Asp Thr Val Val Tyr Tyr Cys Ala Ala Asp Phe Lys Asp Tyr Tyr
1               5                   10                  15

Asp Leu Ala Pro Arg Gly Phe Asp Tyr Trp Gly Gln Gly Thr Gln Val
            20                  25                  30

Thr Val Ser Ser
        35

<210> SEQ ID NO 2
<211> LENGTH: 41
<212> TYPE: PRT
<213> ORGANISM: Artificial Sequence
<220> FEATURE:
<223> OTHER INFORMATION: Synthetic Construct

<400> SEQUENCE: 2

Glu Asp Thr Ala Val Tyr Tyr Cys Ala Ala Asp Arg Tyr Tyr Tyr Cys
1               5                   10                  15

Ser Asp Ser Gly Pro Gly Gly Pro Ile Tyr Glu Tyr Asp Phe Arg Gly
            20                  25                  30

Gln Gly Thr Gln Val Thr Val Ser Ser
        35                  40

<210> SEQ ID NO 3
<211> LENGTH: 38
<212> TYPE: PRT
<213> ORGANISM: Artificial Sequence
<220> FEATURE:
<223> OTHER INFORMATION: Synthetic Construct

<400> SEQUENCE: 3

Glu Asp Thr Ala Val Tyr Tyr Cys Ala Ala Ala Pro Phe Arg Leu Gly
1               5                   10                  15

Arg Arg Thr Trp Ser Pro Asp Asp Phe Asp Ser Trp Gly Arg Gly Thr
            20                  25                  30
```

Gln Val Thr Val Ser Ser
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic Construct

<400> SEQUENCE: 4

Glu Asp Thr Ala Val Tyr Tyr Cys Ala Val Leu Arg Asp Gly Ala Ser
1               5                   10                  15

Asp His Arg Arg Gln Ser Asp Tyr Ser Ile Trp Gly Gln Gly Thr Gln
            20                  25                  30

Val Thr Val Ser Ser
        35

<210> SEQ ID NO 5
<211> LENGTH: 37
<212> TYPE: PRT
<213> ORGANISM: Artificial Sequence
<220> FEATURE:
<223> OTHER INFORMATION: Synthetic Construct

<400> SEQUENCE: 5

Glu Asp Thr Ala Val Tyr Tyr Cys Ala Leu Leu Arg Asp Gly Ala Ser
1               5                   10                  15

Asp His Arg Arg Gln Ser Asp Tyr Ser Ile Trp Gly Gln Gly Thr Gln
            20                  25                  30

Val Thr Val Ser Ser
        35

<210> SEQ ID NO 6
<211> LENGTH: 37
<212> TYPE: PRT
<213> ORGANISM: Artificial Sequence
<220> FEATURE:
<223> OTHER INFORMATION: Synthetic Construct

<400> SEQUENCE: 6

Glu Asp Thr Ala Val Tyr His Cys Ala Ala Leu Arg Asp Gly Ala Ser
1               5                   10                  15

Asp His Thr Arg Glu Ser Asp Tyr Asn Ile Trp Gly Gln Gly Thr Gln
            20                  25                  30

Val Thr Val Ser Ser
        35

<210> SEQ ID NO 7
<211> LENGTH: 29
<212> TYPE: PRT
<213> ORGANISM: Artificial Sequence
<220> FEATURE:
<223> OTHER INFORMATION: Synthetic Construct

<400> SEQUENCE: 7

Glu Asp Thr Ala Val Tyr Tyr Cys Asn Ala Arg Gly Ser Ser Trp Gln
1               5                   10                  15

Glu Glu Tyr Trp Gly Gln Gly Thr Gln Val Thr Ser Ser
            20                  25

<210> SEQ ID NO 8
<211> LENGTH: 39

```
<212> TYPE: PRT
<213> ORGANISM: Artificial Sequence
<220> FEATURE:
<223> OTHER INFORMATION: Synthetic Construct

<400> SEQUENCE: 8

Glu Asp Thr Ala Val Tyr Tyr Cys Ala Ala Arg Glu Phe Gly Tyr Gly
1               5                   10                  15

Gly Gly Val Ser Arg Phe Ile Asp Asp Tyr Asp Tyr Trp Gly Gln Gly
            20                  25                  30

Thr Gln Val Thr Val Ser Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct

<400> SEQUENCE: 9

Glu Asp Thr Ala Val Tyr Tyr Cys Ala Ala Arg Glu Phe Gly Tyr Thr
1               5                   10                  15

Gly Gly Val Ser Gln Phe Ile Ser Asp Tyr Asp Tyr Trp Gly Gln Gly
            20                  25                  30

Thr Gly Val Thr Val Ser Ser
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct

<400> SEQUENCE: 10

Glu Asp Thr Ala Val Tyr Tyr Cys Ala Ala Arg Glu Phe Gly Tyr Thr
1               5                   10                  15

Gly Gly Val Ser Arg Phe Ile Ser Asp Tyr Asp Tyr Trp Gly Gln Gly
            20                  25                  30

Thr Gln Val Thr Val Ser Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct

<400> SEQUENCE: 11

Glu Asp Thr Ala Val Tyr Tyr Cys Ala Ala Gln Glu Phe Gly Tyr Thr
1               5                   10                  15

Ala Gly Ile Ser Arg Phe Ile Ser Asp Tyr Asp Tyr Trp Gly Gln Gly
            20                  25                  30

Thr Gln Val Thr Val Ser Ser
        35

<210> SEQ ID NO 12
<211> LENGTH: 39
<212> TYPE: PRT
<213> ORGANISM: Artificial Sequence
<220> FEATURE:
```

<223> OTHER INFORMATION: Synthetic Construct

<400> SEQUENCE: 12

Glu Asp Thr Ala Val Tyr Tyr Cys Ala Ala Gln Glu Phe Gly Tyr Thr
1               5                   10                  15

Ala Gly Val Ser Arg Phe Ile Ser Asp Tyr Asp Tyr Trp Gly Gln Gly
            20                  25                  30

Thr Gln Val Thr Val Ser Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Construct

<400> SEQUENCE: 13

Glu Asp Thr Ala Val Tyr Tyr Cys Ala Ala Arg Glu Phe Gly Tyr Thr
1               5                   10                  15

Gly Gly Val Ser Arg Phe Ile Ser Asp Tyr Asp Tyr Trp Gly Gln Gly
            20                  25                  30

Thr Gln Val Thr Val Ser Ser
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct

<400> SEQUENCE: 14

Glu Asp Thr Ala Val Tyr Tyr Val Ala Ala Gln Glu Phe Gly Tyr Thr
1               5                   10                  15

Gly Gly Ile Ser Arg Ala Ile Ser Asp Tyr Asp Tyr Trp Gly Gln Gly
            20                  25                  30

Thr Gln Val Thr Val Ser Ser
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic Construct

<400> SEQUENCE: 15

Glu Asp Thr Ala Val Tyr Tyr Cys Ala Ala Gln Glu Phe Gly Tyr Thr
1               5                   10                  15

Gly Gly Ile Ser Gln Phe Ile Ser Asp Tyr Asp Tyr Trp Gly Gln Gly
            20                  25                  30

Thr Gln Val Thr Val Ser Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic Construct

<400> SEQUENCE: 16

Glu Asp Thr Ala Val Tyr Tyr Cys Ala Ala Gln Glu Phe Gly Tyr Thr
1               5                   10                  15

Gly Gly Ile Ser Arg Ala Ile Ser Asp Tyr Asp Tyr Trp Gly Gln Gly
                20                  25                  30

Thr Gln Val Thr Val Ser Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic Construct

<400> SEQUENCE: 17

Glu Asp Thr Ala Val Tyr Tyr Cys Ala Gly Gln Glu Phe Gly Tyr Thr
1               5                   10                  15

Gly Gly Ile Ser Arg Phe Ile Ser Asp Tyr Asp Tyr Trp Gly Gln Gly
                20                  25                  30

Thr Gln Val Thr Val Ser Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Construct

<400> SEQUENCE: 18

Glu Asp Thr Ala Val Tyr Tyr Cys Ala Ala Gln Glu Phe Gly Tyr Thr
1               5                   10                  15

Gly Gly Ile Ser Arg Phe Ile Ser Asp Tyr Asp Tyr Trp Gly Gln Gly
                20                  25                  30

Thr Gln Val Thr Val Ser Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct

<400> SEQUENCE: 19

Glu Asp Thr Ala Val Tyr Tyr Cys Ala Ala Gln Glu Phe Gly Tyr Thr
1               5                   10                  15

Gly Gly Ile Ser Arg Phe Ile Ser Asp Tyr Asp Tyr Trp Gly Gln Gly
                20                  25                  30

Thr Gln Val Thr Val Ser Ser
        35

<210> SEQ ID NO 20
<211> LENGTH: 35
<212> TYPE: PRT
<213> ORGANISM: Artificial Sequence
<220> FEATURE:
<223> OTHER INFORMATION: Synthetic Construct

<400> SEQUENCE: 20

Glu Asp Thr Ala Val Tyr Tyr Cys Ala Ala Ser Thr Pro Pro Ile Arg
1               5                   10                  15

-continued

Thr Ile Pro Asn Thr Tyr Asp Tyr Trp Gly Gln Gly Thr Gln Val Thr
            20                  25                  30

Val Ser Ser
        35

<210> SEQ ID NO 21
<211> LENGTH: 35
<212> TYPE: PRT
<213> ORGANISM: Artificial Sequence
<220> FEATURE:
<223> OTHER INFORMATION: Synthetic Construct

<400> SEQUENCE: 21

Glu Asp Thr Ser Val Tyr Tyr Cys Ala Val Lys Thr Asn Gly Asn Leu
1               5                   10                  15

Tyr Tyr Ala Ser Ala Tyr Asp Tyr Trp Gly Gln Gly Thr Gln Val Thr
            20                  25                  30

Val Ser Ser
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic Construct

<400> SEQUENCE: 22

Glu Asp Thr Ser Val Tyr Tyr Cys Ala Ala Arg Thr Asn Gly Asn Leu
1               5                   10                  15

Tyr Tyr Ala Ser Val Tyr Asp Tyr Trp Gly Gln Gly Thr Gln Val Thr
            20                  25                  30

Val Ser Ser
        35

<210> SEQ ID NO 23
<211> LENGTH: 35
<212> TYPE: PRT
<213> ORGANISM: Artificial Sequence
<220> FEATURE:
<223> OTHER INFORMATION: Synthetic Construct

<400> SEQUENCE: 23

Glu Asp Thr Ser Val Tyr Tyr Cys Ala Ala Arg Thr Asn Gly Asn Leu
1               5                   10                  15

Tyr Tyr Ala Ser Ala Tyr Glu Tyr Trp Gly Gln Gly Thr Gln Val Thr
            20                  25                  30

Val Ser Ser
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic Construct

<400> SEQUENCE: 24

Glu Asp Thr Ser Val Tyr Tyr Cys Ala Ala Arg Thr Asn Gly Asn Leu
1               5                   10                  15

Tyr Tyr Ala Ser Ala Tyr Asp Tyr Trp Gly Gln Gly Thr Gln Val Thr
            20                  25                  30

Val Ser Ser
        35

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Met Leu Thr Phe Leu Lys Lys Gly Ala Asn Val Val Ile Lys Ala Ala
1               5                   10                  15

Ile Thr Pro Thr Thr Ser Lys Leu Pro
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic Construct

<400> SEQUENCE: 26

Met Leu Thr Phe Leu Ala Ala Gly Ala Asn Val Val Ile Lys Ala Ala
1               5                   10                  15

Ile Thr Pro Thr Thr Ser Lys Leu Pro
            20                  25

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Thr Ser Lys Leu Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Thr Ser Ala Leu Pro
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic Construct

<400> SEQUENCE: 29

Ser Lys Leu Pro
1

<210> SEQ ID NO 30
<211> LENGTH: 8
<212> TYPE: PRT

<213> ORGANISM: Artificial Sequence
<220> FEATURE:
<223> OTHER INFORMATION: Synthetic Construct

<400> SEQUENCE: 30

Gly Gly Thr Leu Ser Ser Tyr Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Val Ala Arg Val Asn Gly Arg Ile
1               5

<210> SEQ ID NO 32
<211> LENGTH: 20
<212> TYPE: PRT
<213> ORGANISM: Artificial Sequence
<220> FEATURE:
<223> OTHER INFORMATION: Synthetic Construct

<400> SEQUENCE: 32

Ala Ala Gln Glu Phe Gly Tyr Thr Gly Gly Ile Ser Arg Ala Ile Ser
1               5                   10                  15

Asp Tyr Asp Tyr
            20

<210> SEQ ID NO 33
<211> LENGTH: 127
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Gln Glu Ser Gly Gly Gly Leu Val Gln Ala Gly Gly
1               5                   10                  15

Ser Leu Arg Leu Ser Cys Thr Ala Ser Gly Gly Thr Leu Ser Ser Tyr
            20                  25                  30

Thr Met Gly Trp Phe Arg Gln Ala Pro Gly Lys Glu Arg Asp Phe Val
        35                  40                  45

Ala Thr Val Ala Arg Val Asn Gly Arg Ile Tyr Ala Asp Ser Val
    50                  55                  60

Lys Gly Arg Phe Ile Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gln Glu Phe Gly Tyr Thr Gly Gly Ile Ser Arg Ala Ile Ser
                100                 105                 110

Asp Tyr Asp Tyr Trp Gly Gln Gly Thr Gln Val Thr Val Ser Ser
            115                 120                 125

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

```
<220> FEATURE:
<221> NAME/KEY: SITE
<222> LOCATION: (2)..(2)
<223> OTHER INFORMATION: Xaa is D-phenylalanine
<220> FEATURE:
<221> NAME/KEY: SITE
<222> LOCATION: (3)..(3)
<223> OTHER INFORMATION: Xaa is 2-naphthylalanine
<220> FEATURE:
<221> NAME/KEY: SITE
<222> LOCATION: (5)..(5)
<223> OTHER INFORMATION: Xaa is D-arginine
<220> FEATURE:
<221> NAME/KEY: SITE
<222> LOCATION: (7)..(7)
<223> OTHER INFORMATION: Xaa is D-arginine

<400> SEQUENCE: 34

Phe Xaa Xaa Arg Xaa Arg Xaa Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: (1)..(1)
<223> OTHER INFORMATION: Xaa is D-phenylalanine
<220> FEATURE:
<221> NAME/KEY: SITE
<222> LOCATION: (2)..(2)
<223> OTHER INFORMATION: Xaa is 2-naphthylalanine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: Xaa is D-arginine

<400> SEQUENCE: 35

Xaa Xaa Arg Xaa Arg Xaa Gln
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (2)..(2)
<223> OTHER INFORMATION: Xaa is 2-naphthylalanine

<400> SEQUENCE: 36

Phe Xaa Arg Arg Arg Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (2)..(2)
<223> OTHER INFORMATION: Xaa is 2-naphthylalanine
```

<400> SEQUENCE: 37

Phe Xaa Arg Arg Arg Gln
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is phenylalanine with a tert-butanoyl
      substituent

<400> SEQUENCE: 38

Xaa Arg Arg Arg Arg Gln
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      hexanoyl substituent

<400> SEQUENCE: 39

Xaa Arg Arg Arg Arg Gln
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with an
      octanoyl substituent

<400> SEQUENCE: 40

Xaa Arg Arg Arg Arg Gln
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      decanoyl substituent

<400> SEQUENCE: 41

Xaa Arg Arg Arg Arg Gln
1               5

```
<210> SEQ ID NO 42
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      pyrenoyl substituent

<400> SEQUENCE: 42

Xaa Arg Arg Arg Arg Gln
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      3,3-diphenoyl substituent

<400> SEQUENCE: 43

Xaa Arg Arg Arg Arg Gln
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      fluorenylmethyloxycarbonoyl substituent

<400> SEQUENCE: 44

Xaa Arg Arg Arg Arg Gln
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      1-pyrenylbutanoyl substituent

<400> SEQUENCE: 45

Xaa Arg Arg Arg Arg Gln
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: site
<222> LOCATION: (1)..(1)
<223> OTHER INFORMATION: Xaa is 2,3-diaminopropionic acid with a
      decanoyl substituent
<220> FEATURE:
<221> NAME/KEY: site
<222> LOCATION: (3)..(3)
<223> OTHER INFORMATION: Xaa is D-arginine
<220> FEATURE:
<221> NAME/KEY: site
<222> LOCATION: (5)..(5)
<223> OTHER INFORMATION: Xaa is D-arginine

<400> SEQUENCE: 46

Xaa Arg Xaa Arg Xaa Gln
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      decanoyl substituent
<220> FEATURE:
<221> NAME/KEY: site
<222> LOCATION: (2)..(2)
<223> OTHER INFORMATION: Xaa is D-arginine
<220> FEATURE:
<221> NAME/KEY: site
<222> LOCATION: (4)..(4)
<223> OTHER INFORMATION: Xaa is D-arginine

<400> SEQUENCE: 47

Xaa Xaa Arg Xaa Arg Gln
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: (1)..(1)
<223> OTHER INFORMATION: Xaa is 2,3-diaminopropionic acid with a
      decanoyl substituent

<400> SEQUENCE: 48

Xaa Ala Arg Arg Arg Gln
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      decanoyl substituent

<400> SEQUENCE: 49

Xaa Arg Arg Arg Ala Gln
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      decanoyl substituent

<400> SEQUENCE: 50

Xaa Arg Arg Arg Arg Arg Gln
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is lysine with a decanoyl substituent

<400> SEQUENCE: 51

Xaa Arg Arg Arg Arg Gln
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is 2,3-diaminopropionic acid with a
      decanoyl substituent

<400> SEQUENCE: 52

Xaa Arg Arg Arg Gln
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is ornithine with a decanoyl substituent

<400> SEQUENCE: 53

Xaa Arg Arg Arg Arg Gln
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: site
<222> LOCATION: (1)..(1)
<223> OTHER INFORMATION: Xaa is lysine with a decanoyl substituent
<220> FEATURE:
<221> NAME/KEY: site
<222> LOCATION: (3)..(3)
<223> OTHER INFORMATION: Xaa is D-arginine
<220> FEATURE:
<221> NAME/KEY: site
<222> LOCATION: (5)..(5)
<223> OTHER INFORMATION: Xaa is D-arginine

<400> SEQUENCE: 54

Xaa Arg Xaa Arg Xaa Gln
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is lysine with a decanoyl substituent
<220> FEATURE:
<221> NAME/KEY: site
<222> LOCATION: (2)..(2)
<223> OTHER INFORMATION: Xaa is D-arginine
<220> FEATURE:
<221> NAME/KEY: site
<222> LOCATION: (4)..(4)
<223> OTHER INFORMATION: Xaa is D-arginine

<400> SEQUENCE: 55

Xaa Xaa Arg Xaa Arg Gln
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is asparagine with a decynoyl substituent

<400> SEQUENCE: 56

Xaa Arg Arg Arg Arg Gln
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is asparagine with a decynoyl substituent
<220> FEATURE:
<221> NAME/KEY: site
<222> LOCATION: (3)..(3)
<223> OTHER INFORMATION: Xaa is D-arginine
<220> FEATURE:
<221> NAME/KEY: site
<222> LOCATION: (5)..(5)
<223> OTHER INFORMATION: Xaa is D-arginine
```

```
<400> SEQUENCE: 57

Xaa Arg Xaa Arg Xaa Gln
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is glutamate with a decynoyl substituent
<220> FEATURE:
<221> NAME/KEY: site
<222> LOCATION: (3)..(3)
<223> OTHER INFORMATION: Xaa is D-arginine
<220> FEATURE:
<221> NAME/KEY: site
<222> LOCATION: (5)..(5)
<223> OTHER INFORMATION: Xaa is D-arginine

<400> SEQUENCE: 58

Xaa Arg Xaa Arg Xaa Gln
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is asparagine with a decynoyl substituent
<220> FEATURE:
<221> NAME/KEY: site
<222> LOCATION: (2)..(2)
<223> OTHER INFORMATION: Xaa is D-arginine
<220> FEATURE:
<221> NAME/KEY: site
<222> LOCATION: (4)..(4)
<223> OTHER INFORMATION: Xaa is D-arginine

<400> SEQUENCE: 59

Xaa Xaa Arg Xaa Arg Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is glutamate with a decynoyl substituent
<220> FEATURE:
<221> NAME/KEY: site
<222> LOCATION: (2)..(2)
<223> OTHER INFORMATION: Xaa is D-arginine
<220> FEATURE:
<221> NAME/KEY: site
<222> LOCATION: (4)..(4)
<223> OTHER INFORMATION: Xaa is D-arginine

<400> SEQUENCE: 60

Xaa Xaa Arg Xaa Arg Gln
1               5
```

```
<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Ile Arg Arg Gly Ile Ser Arg Lys
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

Lys Arg Lys Arg Ala Val
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Pro Lys Pro Lys Arg Gln Thr Lys Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct

<400> SEQUENCE: 64

Arg Arg Arg Arg His Cys Asn Arg
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Construct

<400> SEQUENCE: 65

Ile Pro Asp Pro Thr Gly Gln Ser
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic Construct

<400> SEQUENCE: 66

Ile Lys Arg Glu Arg Glu Asn Asp
1               5
```

<210> SEQ ID NO 67
<211> LENGTH: 17
<212> TYPE: PRT
<213> ORGANISM: Artificial Sequence
<220> FEATURE:
<223> OTHER INFORMATION: Synthetic Construct

<400> SEQUENCE: 67

Lys Lys Leu Gln Glu Gln Glu Lys Gln Gln Lys Val Glu Phe Arg Lys
1               5                   10                  15

Arg

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gly Pro Asn Lys Lys Lys Arg Lys Leu
1               5

<210> SEQ ID NO 69
<211> LENGTH: 19
<212> TYPE: PRT
<213> ORGANISM: Artificial Sequence
<220> FEATURE:
<223> OTHER INFORMATION: Synthetic Construct

<400> SEQUENCE: 69

Arg Arg Arg Arg Ala Ser Ala Pro Ile Ser Gln Trp Ser Ser Ser Arg
1               5                   10                  15

Arg Ser Arg

<210> SEQ ID NO 70
<211> LENGTH: 18
<212> TYPE: PRT
<213> ORGANISM: Artificial Sequence
<220> FEATURE:
<223> OTHER INFORMATION: Synthetic Construct

<400> SEQUENCE: 70

Lys Leu Ala Leu Lys Leu Ala Leu Lys Ala Leu Lys Ala Ala Leu Lys
1               5                   10                  15

Leu Ala

<210> SEQ ID NO 71
<211> LENGTH: 13
<212> TYPE: PRT
<213> ORGANISM: Artificial Sequence
<220> FEATURE:
<223> OTHER INFORMATION: Synthetic Construct

<400> SEQUENCE: 71

Phe Leu Pro Leu Ile Gly Arg Val Leu Ser Gly Ile Leu
1               5                   10

<210> SEQ ID NO 72
<211> LENGTH: 26
<212> TYPE: PRT
<213> ORGANISM: Artificial Sequence
<220> FEATURE:
<223> OTHER INFORMATION: Synthetic Construct

```
<400> SEQUENCE: 72

Cys Val Gln Trp Ser Leu Leu Arg Gly Tyr Gln Pro Cys Val Gln
1               5                   10                  15

Trp Ser Leu Leu Arg Gly Tyr Gln Pro Cys
            20                  25

<210> SEQ ID NO 73
<211> LENGTH: 32
<212> TYPE: PRT
<213> ORGANISM: Artificial Sequence
<220> FEATURE:
<223> OTHER INFORMATION: Synthetic Construct

<400> SEQUENCE: 73

Arg Lys Lys Arg Lys Gly Ser Gly Ser Arg Lys Lys Arg Lys Gly Ser
1               5                   10                  15

Gly Ser Arg Lys Lys Arg Lys Gly Ser Gly Ser Arg Lys Lys Arg Lys
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Synthetic Construct

<400> SEQUENCE: 74

Cys Val Gln Trp Ser Leu Leu Arg Gly Tyr Gln Pro Cys Gly Ser Gly
1               5                   10                  15

Ser Cys Val Gln Trp Ser Leu Leu Arg Gly Tyr Gln Pro Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Synthetic Construct

<400> SEQUENCE: 75

Lys Lys Arg Arg Arg Gly Ser Gly Ser Lys Lys Arg Arg Arg Gly Ser
1               5                   10                  15

Gly Ser Lys Lys Arg Arg Arg Gly Ser Gly Ser Lys Lys Arg Arg Arg
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Synthetic Construct

<400> SEQUENCE: 76

Arg Lys Lys Arg Arg Gly Ser Gly Ser Arg Lys Lys Arg Arg Gly Ser
1               5                   10                  15

Gly Ser Arg Lys Lys Arg Arg Gly Ser Gly Ser Arg Lys Lys Arg Arg
            20                  25                  30

<210> SEQ ID NO 77
<211> LENGTH: 17
<212> TYPE: PRT
<213> ORGANISM: Artificial Sequence
<220> FEATURE:
<223> OTHER INFORMATION: Synthetic Construct
```

-continued

<400> SEQUENCE: 77

Arg Gln Ile Lys Ile Trp Phe Gln Asn Arg Arg Met Lys Trp Lys Lys
1               5                   10                  15

Cys

<210> SEQ ID NO 78
<211> LENGTH: 28
<212> TYPE: PRT
<213> ORGANISM: Artificial Sequence
<220> FEATURE:
<223> OTHER INFORMATION: Synthetic Construct

<400> SEQUENCE: 78

Gly Arg Lys Arg Lys Arg Ser Gly Arg Lys Arg Lys Arg Ser Gly Arg
1               5                   10                  15

Lys Arg Lys Arg Ser Gly Arg Lys Arg Lys Arg Ser
            20                  25

<210> SEQ ID NO 79
<211> LENGTH: 28
<212> TYPE: PRT
<213> ORGANISM: Artificial Sequence
<220> FEATURE:
<223> OTHER INFORMATION: Synthetic Construct

<400> SEQUENCE: 79

Pro Arg Lys Lys Arg Gly Arg Pro Arg Lys Lys Arg Gly Arg Pro Arg
1               5                   10                  15

Lys Lys Arg Gly Arg Pro Arg Lys Lys Arg Gly Arg
            20                  25

<210> SEQ ID NO 80
<211> LENGTH: 13
<212> TYPE: PRT
<213> ORGANISM: Artificial Sequence
<220> FEATURE:
<223> OTHER INFORMATION: Synthetic Construct

<400> SEQUENCE: 80

Cys Val Gln Trp Ser Leu Leu Arg Gly Tyr Gln Pro Cys
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: site
<222> LOCATION: (1)..(1)
<223> OTHER INFORMATION: Xaa is Arg or Lys
<220> FEATURE:
<221> NAME/KEY: site
<222> LOCATION: (3)..(3)
<223> OTHER INFORMATION: Xaa is Arg or Lys
<220> FEATURE:
<221> NAME/KEY: site
<222> LOCATION: (5)..(5)
<223> OTHER INFORMATION: Xaa is Arg or Lys

<400> SEQUENCE: 81

Xaa Lys Xaa Arg Xaa Gly Ser Gly Ser
1               5

```
<210> SEQ ID NO 82
<211> LENGTH: 6
<212> TYPE: PRT
<213> ORGANISM: Artificial Sequence
<220> FEATURE:
<223> OTHER INFORMATION: Synthetic Construct

<400> SEQUENCE: 82

His His His His His His
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Arg Lys Lys Arg Arg Gln Arg Arg Arg
1               5

<210> SEQ ID NO 84
<211> LENGTH: 12
<212> TYPE: PRT
<213> ORGANISM: Artificial Sequence
<220> FEATURE:
<223> OTHER INFORMATION: Synthetic Construct

<400> SEQUENCE: 84

Arg Gln Ala Arg Arg Asn Arg Arg Arg Arg Trp Arg
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

Pro Lys Lys Lys Arg Lys Val
1               5

<210> SEQ ID NO 86
<211> LENGTH: 12
<212> TYPE: PRT
<213> ORGANISM: Artificial Sequence
<220> FEATURE:
<223> OTHER INFORMATION: Synthetic Construct

<400> SEQUENCE: 86

His His His His His His His His His His His His
1               5                   10

<210> SEQ ID NO 87
<211> LENGTH: 52
<212> TYPE: DNA
<213> ORGANISM: Artificial Sequence
<220> FEATURE:
<223> OTHER INFORMATION: Synthetic Construct

<400> SEQUENCE: 87
ggaattccat atggaaaacc tgtattttca gggcatgctt actttcttaa ag        52

<210> SEQ ID NO 88
<211> LENGTH: 69
```

<212> TYPE: DNA
<213> ORGANISM: Artificial Sequence
<220> FEATURE:
<223> OTHER INFORMATION: Synthetic Construct

<400> SEQUENCE: 88
cgcggatcct tattcatgcc attcaatttt ctgcgcttca aaaatatcgt tcaggcctct    60
tgcatgtac                                                            69

<210> SEQ ID NO 89
<211> LENGTH: 52
<212> TYPE: DNA
<213> ORGANISM: Artificial Sequence
<220> FEATURE:
<223> OTHER INFORMATION: Synthetic Construct

<400> SEQUENCE: 89
ggaattccat atggaaaacc tgtattttca gggccatcaa gaaagcgtag gt            52

<210> SEQ ID NO 90
<211> LENGTH: 53
<212> TYPE: DNA
<213> ORGANISM: Artificial Sequence
<220> FEATURE:
<223> OTHER INFORMATION: Synthetic Construct

<400> SEQUENCE: 90
cgcggatcct tattcatgcc attcaatttt ctgcgcttca aaaatatcgt tca           53

<210> SEQ ID NO 91
<211> LENGTH: 52
<212> TYPE: DNA
<213> ORGANISM: Artificial Sequence
<220> FEATURE:
<223> OTHER INFORMATION: Synthetic Construct

<400> SEQUENCE: 91
ggaattccat atggaaaacc tgtattttca gggcaaacac tttgacttaa ga            52

<210> SEQ ID NO 92
<211> LENGTH: 69
<212> TYPE: DNA
<213> ORGANISM: Artificial Sequence
<220> FEATURE:
<223> OTHER INFORMATION: Synthetic Construct

<400> SEQUENCE: 92
cgcggatcct tattcatgcc attcaatttt ctgcgcttca aaaatatcgt tcaggcctct    60
tgcatgtac                                                            69

<210> SEQ ID NO 93
<211> LENGTH: 52
<212> TYPE: DNA
<213> ORGANISM: Artificial Sequence
<220> FEATURE:
<223> OTHER INFORMATION: Synthetic Construct

<400> SEQUENCE: 93
ggaattccat atggaaaacc tgtattttca gggcgaagta gctctgaaag ta            52

<210> SEQ ID NO 94
<211> LENGTH: 69
<212> TYPE: DNA
<213> ORGANISM: Artificial Sequence
<220> FEATURE:

<223> OTHER INFORMATION: Synthetic Construct

<400> SEQUENCE: 94
cgcggatcct tattcatgcc attcaatttt ctgcgcttca aaaatatcgt tcaggcctct    60
tgcatgtac    69

<210> SEQ ID NO 95
<211> LENGTH: 52
<212> TYPE: DNA
<213> ORGANISM: Artificial Sequence
<220> FEATURE:
<223> OTHER INFORMATION: Synthetic Construct

<400> SEQUENCE: 95
ggaattccat atggaaaacc tgtattttca gggcactaaa aaagatacct ta    52

<210> SEQ ID NO 96
<211> LENGTH: 69
<212> TYPE: DNA
<213> ORGANISM: Artificial Sequence
<220> FEATURE:
<223> OTHER INFORMATION: Synthetic Construct

<400> SEQUENCE: 96
cgcggatcct tattcatgcc attcaatttt ctgcgcttca aaaatatcgt tcaggcctct    60
tgcatgtac    69

<210> SEQ ID NO 97
<211> LENGTH: 37
<212> TYPE: DNA
<213> ORGANISM: Artificial Sequence
<220> FEATURE:
<223> OTHER INFORMATION: Synthetic Construct

<400> SEQUENCE: 97
agtgctagcc gccaccatgg tgctgacctt cctgaag    37

<210> SEQ ID NO 98
<211> LENGTH: 28
<212> TYPE: DNA
<213> ORGANISM: Artificial Sequence
<220> FEATURE:
<223> OTHER INFORMATION: Synthetic Construct

<400> SEQUENCE: 98
caagaattcg tctggcatgc acctttcc    28

<210> SEQ ID NO 99
<211> LENGTH: 35
<212> TYPE: DNA
<213> ORGANISM: Artificial Sequence
<220> FEATURE:
<223> OTHER INFORMATION: Synthetic Construct

<400> SEQUENCE: 99
agtgctagcc gccaccatgg tgctgacctt cctga    35

<210> SEQ ID NO 100
<211> LENGTH: 29
<212> TYPE: DNA
<213> ORGANISM: Artificial Sequence
<220> FEATURE:
<223> OTHER INFORMATION: Synthetic Construct

<400> SEQUENCE: 100
caagaattcg ggtccgagaa taaggcata        29

<210> SEQ ID NO 101
<211> LENGTH: 37
<212> TYPE: DNA
<213> ORGANISM: Artificial Sequence
<220> FEATURE:
<223> OTHER INFORMATION: Synthetic Construct

<400> SEQUENCE: 101
agtgctagcc gccaccatgg tgctgacctt cctgaag        37

<210> SEQ ID NO 102
<211> LENGTH: 40
<212> TYPE: DNA
<213> ORGANISM: Artificial Sequence
<220> FEATURE:
<223> OTHER INFORMATION: Synthetic Construct

<400> SEQUENCE: 102
ccgggagtgc tgttcactgt gaactcctgg gtggctgaca        40

<210> SEQ ID NO 103
<211> LENGTH: 40
<212> TYPE: DNA
<213> ORGANISM: Artificial Sequence
<220> FEATURE:
<223> OTHER INFORMATION: Synthetic Construct

<400> SEQUENCE: 103
tgtcagccac ccaggagttc acagtgaaca gcactcccgg        40

<210> SEQ ID NO 104
<211> LENGTH: 28
<212> TYPE: DNA
<213> ORGANISM: Artificial Sequence
<220> FEATURE:
<223> OTHER INFORMATION: Synthetic Construct

<400> SEQUENCE: 104
caagaattcg tctggcatgc acctttcc        28

<210> SEQ ID NO 105
<211> LENGTH: 50
<212> TYPE: DNA
<213> ORGANISM: Artificial Sequence
<220> FEATURE:
<223> OTHER INFORMATION: Synthetic Construct

<400> SEQUENCE: 105
agtgctagcc gccaccatgg tgctgacctt cctggccgct ggcgccaacg        50

<210> SEQ ID NO 106
<211> LENGTH: 28
<212> TYPE: DNA
<213> ORGANISM: Artificial Sequence
<220> FEATURE:
<223> OTHER INFORMATION: Synthetic Construct

<400> SEQUENCE: 106
caagaattcg tctggcatgc acctttcc        28

<210> SEQ ID NO 107
<211> LENGTH: 41
<212> TYPE: DNA

```
<213> ORGANISM: Artificial Sequence
<220> FEATURE:
<223> OTHER INFORMATION: Synthetic Construct

<400> SEQUENCE: 107
agtgctagcc gccaccatgg tgaccacaag caagctgcct c                 41

<210> SEQ ID NO 108
<211> LENGTH: 28
<212> TYPE: DNA
<213> ORGANISM: Artificial Sequence
<220> FEATURE:
<223> OTHER INFORMATION: Synthetic Construct

<400> SEQUENCE: 108
caagaattcg tctggcatgc acctttcc                               28

<210> SEQ ID NO 109
<211> LENGTH: 41
<212> TYPE: DNA
<213> ORGANISM: Artificial Sequence
<220> FEATURE:
<223> OTHER INFORMATION: Synthetic Construct

<400> SEQUENCE: 109
agtgctagcc gccaccatgg tgaccacaag cgctctgcct c                 41

<210> SEQ ID NO 110
<211> LENGTH: 28
<212> TYPE: DNA
<213> ORGANISM: Artificial Sequence
<220> FEATURE:
<223> OTHER INFORMATION: Synthetic Construct

<400> SEQUENCE: 110
caagaattcg tctggcatgc acctttcc                               28

<210> SEQ ID NO 111
<211> LENGTH: 42
<212> TYPE: DNA
<213> ORGANISM: Artificial Sequence
<220> FEATURE:
<223> OTHER INFORMATION: Synthetic Construct

<400> SEQUENCE: 111
agtgctagcc gccaccatgg tgaagctgcc tcaccaggag tc                42

<210> SEQ ID NO 112
<211> LENGTH: 28
<212> TYPE: DNA
<213> ORGANISM: Artificial Sequence
<220> FEATURE:
<223> OTHER INFORMATION: Synthetic Construct

<400> SEQUENCE: 112
caagaattcg tctggcatgc acctttcc                               28

<210> SEQ ID NO 113
<211> LENGTH: 40
<212> TYPE: DNA
<213> ORGANISM: Artificial Sequence
<220> FEATURE:
<223> OTHER INFORMATION: Synthetic Construct

<400> SEQUENCE: 113
agtgctagcc gccaccatgg tgcctcacca ggagtccgtg                  40
```

```
<210> SEQ ID NO 114
<211> LENGTH: 28
<212> TYPE: DNA
<213> ORGANISM: Artificial Sequence
<220> FEATURE:
<223> OTHER INFORMATION: Synthetic Construct

<400> SEQUENCE: 114
caagaattcg tctggcatgc acctttcc                                          28

<210> SEQ ID NO 115
<211> LENGTH: 46
<212> TYPE: DNA
<213> ORGANISM: Artificial Sequence
<220> FEATURE:
<223> OTHER INFORMATION: Synthetic Construct

<400> SEQUENCE: 115
ctagctagcg ctaccggtcg ccaccatggc ccaggtgcag ctgcag                      46

<210> SEQ ID NO 116
<211> LENGTH: 33
<212> TYPE: DNA
<213> ORGANISM: Artificial Sequence
<220> FEATURE:
<223> OTHER INFORMATION: Synthetic Construct

<400> SEQUENCE: 116
ccggaattct tatcaggaac cgtagtccgg aac                                    33
```